US006500669B1

(12) United States Patent
Essigmann et al.

(10) Patent No.: US 6,500,669 B1
(45) Date of Patent: *Dec. 31, 2002

(54) PROGRAMMABLE GENOTOXIC AGENTS AND USES THEREFOR

(75) Inventors: John M. Essigmann, Cambridge, MA (US); Robert G. Croy, Belmont, MA (US); Kevin J. Yarema, Albany (CA); Marshall Morningstar, San Diego, MD (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/103,671

(22) Filed: Jun. 23, 1998

Related U.S. Application Data

(63) Continuation-in-part of application No. 08/434,664, filed on May 4, 1995, now Pat. No. 5,879,917, which is a continuation-in-part of application No. 08/239,428, filed on May 4, 1994, now Pat. No. 5,882,941.

(51) Int. Cl.[7] ...................... C12N 15/01; C07D 209/04; C07J 53/00

(52) U.S. Cl. ........................ 435/441; 548/510; 552/502
(58) Field of Search .............................. 435/440, 441; 548/510; 552/502

(56) References Cited

U.S. PATENT DOCUMENTS

| 3,299,104 A | 1/1967 | Fex et al. |
| 5,354,745 A | 10/1994 | Tamura et al. |
| 5,879,917 A | * 3/1999 | Essigmann et al. ......... 435/440 |

FOREIGN PATENT DOCUMENTS

| CA | 1 265 811 | 2/1990 |
| EP | 0 208 446 | 6/1986 |
| WO | WO91/08743 | 12/1990 |
| WO | WO 92/14843 | 3/1992 |

OTHER PUBLICATIONS von Angerer et al. Platinum complexes with a selective action on estrogen receptor–positive mammary tumors. Anti–Cancer Drug Design vol. 4 pp. 21–35, 1989.*
Karl et al. Ring–substituted [1,2–Bis(4–hydroxyphenyl)ethylenediamine]dichloroplatinum(II) complexes: Compounds with a selective effect on the hormone–dependent mammary carcinoma. J. Med. Chem. vol. 31 pp. 72–83, 1988.*
Nobori et al. (1994), Deletions of the Cyclin–Dependent Kinase–4 Inhibitor Gene in Multiple Human Cancers,: 368 *Nature* 753–756.
Xiong et al. (1993), "Subunit Rearrangement of the Cyclin–Dependent Kinases is Associated with Cellular Transformation," 7 *Genes & Dev.*, 1572–1583.
Keyomarsi et al. (1993), "Redundant Cyclin Overexpression and Gene Amplification in Breast Cancer Cells," 90 *Proc. Nat'l. Acad. Sci., USA* 1112–1116.
Stephen et al. (1992), "Mutant Conformation of p53," 225 *J. Mol. Biol.* 577–583.
Hollstein et al. (1991), "p53 Mutations in Human Cancers," 253 *Science* 49–53.
Marx (1990), "Genetic Defect Identified in Rare Cancer Syndrome," 250 *Science* 1209.
Malkin et al. (1990), "Germ Line p53 Mutations in a Familial Syndrome of Breast Cancer, Sarcomas, and Other Neoplasms," 250 *Science* 1233–1238.
Vogelstein (1990), "A Deadly Inheritance," 348 *Nature* 681–682.
Srivastava et al. (1990), "Germ–Line Transmission of a Mutated p53 Gene in a Cancer–prone Family with Li–Fraumeni Syndrome," 348 *Nature* 747–749.
Gannon et al. (1990), "Activating Mutations in p53 Produce a Common Conformational Effect. A Monoclonal Antibody Specific For The Mutant Form," 9 *EMBO J.* 5:1595–1602.
Muntzing et al. (1972), "Lipofuscin in Malignant and Non-–Malignant Human Prostatic Tissue," 77 *Z. Krebsforsch* 166–170.
Niculescu–Duvaz et al. (1966), "Potential Anticancer Agents II Urethan Type Nitrogen Mustards of Some Natural Sex Hormones," 10 *J. Med. Chem.* 172–174.
Holley et al. (1992), "Targeting of Tumor Cells and DNA by a Chlorambucil–Spermicide Conjugate," 52 *Cancer Res.* 4190–4195.
Kosano et al. (1992), "Growth–Inhibitory Action of An Estrogen–Chloramucil Conjugate (KM2210) in Human Breast Cancer Cell Line MCF–7: Its Relationship to Reduction of Estrogen Receptor and Transforming Growth Factor–a Section," 52 *Cancer Res.* 1187–1191.
Otto et al. (1991), "Dissociation of Estrogenic and Cytotoxic Properties of an Estrogen Receptor–Binding Platinum Complex in Human Breast Cancer Cell Lines," 51 *Cancer Res.* 3217–3223.

(List continued on next page.)

*Primary Examiner*—John S. Brusca
(74) *Attorney, Agent, or Firm*—Testa Hurwitz & Thibeault LLP

(57) ABSTRACT

The compositions and methods disclosed herein provide heterobifunctional programmable genotoxic compounds that can be designed to kill selected cells present in a heterogenous cell population. The present compounds comprise a first agent that inflicts damage on cellular DNA, and a second agent that attracts a macromolecular cell component such as a protein, which in turn shields genomic lesions from repair. Unrepaired lesions therefore persist in the cellular genome and contribute to the death of selected cells. In contrast, lesions formed in nonselected cells, which lack the cell component, are unshielded and thus are repaired. As a result, compounds described herein are less toxic to nonselected cells. Compounds of this invention can be designed to cause the selective killing of transformed cells, viral–infected cells and the like.

36 Claims, 18 Drawing Sheets

OTHER PUBLICATIONS

Knebel and von Angerer (1991), "2–Phenylindole–Linked [2–(Aminoalkyl) pyridine] dichloroplatinum(II): Complexes With A Selective Action on Estrogen Receptor Positive Mammary Tumors," 34 *J. Med. Chem.* 7:2145–2152.

von Angerer et al. (1984), "2Phenylindoles—Relationship Between Structure, Estrogen Receptor Affinity, and Mammary Tumor Inhibiting Activity in the Rat," 27 *J. Med. Chem.* 1439–1447.

Georgiadis et al. (1987), "Synthesis and Biological Studies Steroidal cis–Platinum(II) Complexes," 138 *Inorg. Chim. Acta* 249–252.

Wakeling and Bowler (1988), "Novel Antioestrogens Without Partial Agonist Activity," 31 *J. Steroid Biochem.* No. 4B:645–653.

Jones et al. (1984) "Antiestrogens 2. Structure–Activity Studies in a Series of 3–Aroyl–2–arylbenzo[b]thiophene Derivatives Leading to [6–Hydroxy–2–(4–hydroxyphenyl)benzol[b]thien–3–yl][4–[2–(1–piperidinyl)ethoxy]–phenyl]methanone Hydrochloride (LY156768), a Remarkably Effective Estrogen Antagonist With Only Minimal Intrinsic Estrogenicity," 27 *J. Med. Chem.* 1057–1066.

Leclercq et al. (1983), "Guide–Lines in the Design of New Antiestrogens and Cytotoxic–Linked Estrogens For The Treatment of Breast Cancer," 19 *J. Steroid Biochem.* 75–85.

Katzenellenbogen et al. (1980), "The Chemistry of Estrogens and Antiestrogens: Relationships Between Structure, Receptor Binding, and Biological Activity," *Estrogens in the Environment* (Mclachlan, ed.) 33–51.

Jordan et al. (1980), "Structural Derivatives of Tamifoxen and Oestradiol 3–methyl Ether as Potential Alkylating Anti-oestrogens," 17 *Eur. J. Cancer* 193–201.

Redeuilh et al. (1980), "Properties of Biospecific Absorbents Obtained by Immobilization of Oestradiol 7 Derivatives, For Purification of Calf–Uterine Cytosol Oestradiol Receptor," 106 *Eur. J. Biochem.* 481–493.

Jones et al. (1993), "Preferential Binding of the Xeroderma Pigmentosum Group A Complementing Protein to Damaged DNA," 32 *Biochem.* 12096–12104.

Batist et al. (1989), "Enhanced DNA Cross–Link Removal: The Apparent Mechanism of Resistance in a Clinically Relevant Melphalan–Resistant Human Breast Cancer Cell Line," 39 *Mol. Pharmacol.* 224–230.

Devchand et al. (1993), "Uracil–DNA Glycosylase As A Probe For Protein–DNA Interactions," 21 *Nucl. Acids Res.* 15:3437–3443.

Sibghat–Ullah and Sancar (1990), "Substrate Overlap and Functional Competition Between Human Nucleotide Excision Repair and *Escherichia coli* Photolyase and (A)BC Excision Nuclease," 29 *Biochem.* 5711–5718.

Lippard (1994), "Structural and Biological Consequences of Platinum Anticancer Drug Binding to DNA," Chapter 4 of Proceedings of The Robert A. Welch Foundation 37th Conference on Chemical Research, 40 Years of the DNA Double Helix, Oct. 25–26, 1993, The Westin Oaks Hotel, Houston, Texas (1994).

Bruhn et al. (1993), "Isolation and Characterization of cDNA Clones Encoding the Drosophila Homolog of the HMG–Box SSRP Family That Recognized Specific DNA Structures," 21 *Nucl. Acids Res.* 1643–1646.

Bradley et al. (1993), "Mutagenicity and Genotoxicity of the Major DNA Adduct of the Anti–Tumor Druge cis–Diamminedichloroplatinum(II)," 32 *Biochem.* 982–988.

Brown et al. (1993), "Ixrl, a Yeast Protein That Binds to Platinated DNA and Confers Sensitivity to Cisplatin," 261 *Science* 603–605.

Weir et al. (1993), "Structure of the HMG Box Motif in the B–Domain of HMG1," 12 *EMBO J.* 4:1311–1319.

Pil et al. (1993), "High–Mobility Group 1 Protein Mediates DNA Bending as Determined by Ring Closures," 90 *Proc. Nat'l. Acad. Sci. USA* 9465–9469.

Dabholkar et al. (1992), "Determinants of Cisplatin Sensitivity in Non–Malignant Non–Drug Selected Human T Cells," 274 *Mut. Res.* 45–56.

Treiber et al. (1992), "An Ultraviolet Light–Damaged DNA Recognition Protein Absent in Xeroderma Pigmentosum Group E Cells Binds Selectively to Pyrimidine (6–4) Pyrimidome Photoproducts," 20 *Nucl. Acids Res.* 21:5805–5810.

Szymkowski et al. (1992), "An Intrastrand d(GpG) Platinum Crosslink in Duplex M13 DNA is Refractory to Repair by Human Cell Extracts," 89 *Proc. Nat'l. Acad. Sci. USA* 10772–10776.

Zhen et al. (1992), "Increased Gene–Specific Repair of Cisplatin Interstrand Cross–Links in Cisplatin–Resistant Human Ovarian Cancer Cell Lines," 12 *Mol. Cell. Biol.* 9:3689–3698.

Hughes et al. (1992), "Purification of Nuclear Proteins That Bind to Cisplatin–Damaged DNA," 267 *J. Biol. Chem.* 13520–13527.

Pil et al. (1992), "Specific Binding of Chromosomal Protein HMG 1 to DNA Damaged by the Anticancer Drug Cisplatin," 256 *Science* 234–237.

Bruhn et al. (1992), "Isolation and Characterization of Human cDNA Clones Encoding a High Mobility Group Box Protein That Recognizes Structural Distortions to DNA Caused by Binding of the Anticancer Agent Cisplatin," 89 *Proc. Nat'l. Acad. Sci. USA* 2307–2311.

Donahue et al. (1991), "A Protein From Mammalian Cells That Recognizes Platinated DNA," *Platinum and Other Metal Coord. Compounds in Cancer Chemotherapy*, 241–251.

Jones et al. (1991), "Gene–Specific Formation and Repair of Cisplatin Intrastrand Adducts and Interstrand Cross–Links in Chinese Hamster Ovary Cells," 266 *J. Biol. Chem.* 11:7101–7107.

Sorenson et al. (1990), "Analysis of Events Associated With Cell Cycle Arrest at G2 Phase and Cell Death Induced by Cisplatin," 82 *J. Natl. Cancer Inst.* 9:749–755.

Donahue et al. (1990), "Characterization of a DNA Damage–Recognition Protein From Mammalian Cells That Binds Specifically to Intrastrand d(GpG) and d(ApG) DNA Adducts of the Anticancer Drug Cisplatin," 29 *Biochem.* 5872–5880.

Bruhn et al. (1990), "Biological Processing of DNA Modified By Platinum Compounds," 38 *Prog. in Org. Chem: Bioorg. Chem.* 477–516.

Dijt et al. (1988), "Formation and Repair of Cisplatin–Induced Adducts to DNA in Cultured Normal and Repair–Deficient Human Fibroblasts," 48 *Cancer Res.* 6058–6062.

Chu et al. (1988), "Xeroderma Pigmentosum Group E Cells Lack a Nuclear Factor That Binds to Damaged DNA," 242 *Science* 564–567.

Fichtinger–Schepman et al. (1987), "cis–Diamminedichloroplatinum(II)–Induced DNA Adducts in Peripheral Leukocytes From Seven Cancer Patients Quantitative Immunochemical Detection of the Adduct Induction and Removal After a Single Dose of cis–Diamminedichloroplatinum(II)," 47 *Cancer Res.* 3000–3004.

Ciccarelli et al. (1985), "In Vivo Effects of cis– and trans–diamminedichloroplatinum(II) on SV40 Chromosomes: Differential Repair, DNA–Protein Crosslinking and Inhibition of Replication," 24 *Biochem.* 7533–7540.

Jones et al. (1985), "Cis–Diamminedichloroplatinum(II)–Induced Acute Renal Failure in the Rate," 52 *Laboratory Invest.* 4:363–374.

Pinto et al. (1985), "Sequence–Dependent Termination of in vitro DNA Synthesis by cis–and trans–diamminedichloroplatinum(II)," 82 *Proc. Nat'l. Acad. Sci. USA* 4616–4619.

Hoy et al. (1985), "Defective DNA Cross–Link Removal in Chinese Hamster Cell Mutants Hypersensitive to Bifunctional Alkylating Agents," 45 *Cancer Res.* 1737–1743.

Loehrer et al. (1984), "Cisplatin," 100 *Ann.Int. Med.* 704–713.

Ishida et al. (1982), "Susceptibility of Fanconi's Anemia Lymphoblasts to DNA–Cross–Linking and Alkylating Agents," 42 *Cancer Res.* 4000–4006.

Zwelling et al. (1981), "DNA Cross–Linking As An Indicator Of Sensitive and Resistant of Mouse L1210 Leukemia to cis–diamminedichloroplatinum(II) and L–phenylalanine Mustard," 41 *Cancer Res.* 640–649.

Bianchi et al. (1992), "The DNA Binding Sit of HMG1 Protein is Composed of Two Similar Segments (HMG Boxes), Both of Which Have Counterparts in Other Eukaryotic Regulatory Proteins," 11 *EMBO J.* 3:1055–1063.

Lilley (1992), "HMG has DNA Wrapped Up," 357 *Nature* 282–283.

Bustin et al. (1990), "Structural Features of the HMG Chromosomal Proteins and Their Genes," 1049 *Biochim & Biophys. Acta* 231–243.

King et al. (1993), "The SRY High–Mobility–Group Box Recognizes DNA by Partial Intercalation in the Minor Groove: A Topological Mechanism of Sequence Specificity," 90 *Proc. Nat'l. Acad. Sci. USA* 11990–11994.

Ferrari et al. (1992), "SRY, Like HMG 1, Recognizes Sharp Angles in DNA," 11 *EMBO J.* 12:4497–4506.

Giese et al. (1992), "The HMG Domain of Lymphoid Enhancer Factor 1 Bends DNA and Facilitate Assembly of Functional Nucleoprotein Structures," 69 *Cell* 185–195.

Giese et al. (1991), "DNA–Binding Properties of the HMG Domain of the Lymphoid–Specific Transcriptional Regulator LEF–1," 5 *Genes & Dev.* 2567–2578.

Putnam et al. (1992), "Cooperative Binding of the Xenopus RNA Polymerase I Transcription Factor xUBF to Repetitive Ribosomal Gene Enhancers," 12 *Mol. & Cellular Biology* 11:4970–4980.

Jantzen et al. (1992), "Multiple Domains of the RNA Polymerase I Activator hUBF Interact With the TATA–Binding Protein Complex hSL1 to Mediate Transcription," 6 *Genes & Dev.* 1950–1963.

Jantzen et al. (1990), "Nucleolar Transcription Factor hUBF Contains a DNA–Binding Motif With Homology to HMG Proteins," 344 *Nature* 830–836.

Bell et al. (1988), "Functional Cooperativity Between Transcription Factors UBF1 and SL1 Mediates Human Ribosomal RNA Synthesis," 241 *Science* 1192–1197.

Chan et al. (1991), "Human Autoantibody to RNA Polymerase I Transcription Factor hUBF. Molecular Identity of Nucleolus Organizer Region Autoantigen NOR–90 and Ribosomal RNA Transcription Upstream Binding Factor," 174 *J. Exp. Med.* 1239–1244.

Cho et al. (1993), "An Unnatural Biopolymer," 261 *Science* 1303–1305.

Clusel et al. (1993), "Ex Vivo Regulation of Specific Gene Expression By Nanomolar Concentration of Double–Stranded Dumbbell Oligonucleotides," 21 *Nucl. Acids Res.* 21:3405–3411.

Chu et al. (1992), "The Stability of Different Forms of Double–Stranded Decoy DNA in Serum and Nuclear Extracts," 20 *Nucl. Acids Res.* 21:5857–5858.

Riordan et al. (1991), "Oligonucleotide–Based Therapeutics," 350 *Nature* 442–443.

Bielinska et al. (1990), "Regulation of Gene Expression With Double–Stranded Phosphorothioate Oligonucleotides," 250 *Science* 997–1000.

Lorsch et al. (1994), "In Vitro Selection of RNA Aptamers Specific For Cyanocobalamin," *Biochem.* 973–982.

Sassanfar et al. (1993), "An RNA Motif That Binds ATP," 364 *Science* 550–552.

Tuerk et al. (1993), "In Vitro Evolution of Functional Nucleic Acids: High Affinity RNA Ligands of HIV–1 Proteins," 137 *Gene* 33–39.

Schneider et al. (1993), "Selective Enrichment of RNA Species For Tight Binding to *E. Coli* rho Factor," 7 *FASEB J.* 201–207.

Burke et al. (1993), "In Vitro Selection and Evolution of RNA: Applications For Catalytic RNA, Molecular Recognition and Drug Discovery," 7 *FASEB J.* 106–112.

Schneider et al. (1992), "Selection of High Affinity RNA Ligands to the Bacteriophage R17 Coat Protein," 228 *J. Mol. Biol.* 862–869.

Szostak (1992), "In Vitro Genetics," 17 *Trends in Biol. Sci.* 89–93.

Famulok et al. (1992), "In Vitro Selection of Specific Ligand–Binding Nucleic Acids," 31 *Angew. Chem. Int. Ed. Engl.* 979–988.

Bock et al. (1992), "Selection of Single–Stranded DNA Molecules That Bind and Inhibit Human Thrombin," 355 *Nature* 564–566.

Ellington et al. (1992), "Selection In Vitro of Single–Stranded DNA Molecules That Fold Into Specific Ligand–Binding Structures," 355 *Nature* 850–852.

Ellington et al. (1990), "In Vitro Selection of RNA Molecules That Bind Specific Ligands," 346 *Nature* 818–822.

Abelson, John (1990), "Directed Evolution of Nucleic Acids by Independent Replication and Selection," 249 *Science* 488–489.

Tuerk et al. (1990), "Systematic Evolution of Ligands by Exponential Enrichment: RNA Ligands to Bacteriophage T4 DNA Polymerase," 249 *Science* 505–510.

Fodor et al. (1991), "Light–Directed, Spatially Addressable Parallel Chemical Synthesis," 251 *Science* 767–773.

Scott et al. (1990), "Searching for Peptide Ligands With An Epitope Library," 249 *Science* 386–390.

Geysen et al. (1984), "Use of Peptide Synthesis to Probe Viral Antigens for Epitopes to a Resolution of a Single Amino Acid," 81 *Proc. Nat'l. Acad. Sci. USA* 3998–4002.

Ohlmeyer et al. (1993), "Complex Synthetic Chemical Libraries Indexed With Molecular Tags," 90 *Proc. Nat'l. Acad. Sci. USA* 10922–10926.

Needels et al. (1993), "Generation and Screening of an Oligonucleotide Encoded Synthetic Peptide Library," 90 *Proc. Nat'l. Acad. Sci. USA* 10700–10704.

Comess et al. (1992), "Replication Inhibition and Translesion Synthesis on Templates Containing Site–Specifically Placed cis–Diamminedichloroplatinum(II) DNA Adducts," 31 *Biochemistry* 3975–3990.

Treiber et al. (1994), "Cisplatin–DNA Adducts Are Molecular Decoys For The Ribosomal RNA Transcription Factor hUBF (human upstream binding factor)," 91 *Proc. Natl. Acad. Sci. USA* 5672–5676.

Gallego et al. (1985), "Monoclonal Antibody–Drug Conjugates: A New Approach For Cancer Therapy," 21 *Drugs of Today* 11:511–521.

Yang et al. (1988), "Doxorubicin Conjugated With A Monoclonal Antibody Directed To A Human Melanoma–Associated Proteoglycan Suppresses The Growth of Established Tumor Xenografts In Nude Mice," 85 *Proc. Natl. Acad. Sci. USA* 1189–1193.

Roth, et al., "Synthesis of Novel Androgen–Linked Phosphoramide Mustard Prodrugs and Growth–Inhibitory Activity in Human Breast Cancer Cells," (1995) *Anti–Cancer Drug Design*, 10:655–66.

Jordan, et al., "Structure–Activity Relationship of Estrogens," (1985) *Environmental Health Perspectives*, 61: 97–110.

Lam, et al., "Estrogen Receptor–Binding Affinity and Cytotoxic Activity of Three New Estrogen–Nitrosourea Conjugates in Human Breast Cancer Cell Lines in Vitro," (1987) *Cancer Treatment Reports*, 71:901–06.

McA'Nulty, et al., "The HMG–Domain Protein Ixr1 Blocks Excision Repair of Cisplatin–DNA Adducts in Yeast," (1996) *Mutation Research*, 362:75–86.

Pomper, Martin, et al. "11β–Methoxy–, 11β–Ehtyl– and 17α–Ethynyl–Substituted 16α–Fluoroestradiols: Receptor––Based Imaging Agents with Enhanced Uptake Efficiency and Selectivity,"*J. Med. Chem.* 1990, 33, 3143–3155.

Salman, Mohammad, et al. "A Progesterone Receptor Affinity Chromatography Reagent: 17α–Hexynyl Nortestosterone Sepharose," *J. steroid Biochem*, vol. 26, No. 3, pp. 383–391, 1987.

Napolitano, Elio, et al. "11β Substituted Estradiol Derivatives, Potential High Affinity Carbon–11–Labeled Probes for the Estrogen Receptor: A Structure–Affinity Relationship Study," *J. Med. Chem.*, 1995, 38, 429–434.

Bindal, Rajeshwar, et al. "11β–Chloromethyl–[$^3$H]estradiol–17β: A Very High Affinity, Reversible Ligand for the Estrogen Receptor," *J. steroid Biochem.*, vol. 28, No. 4, pp. 361–370, 1987.

* cited by examiner

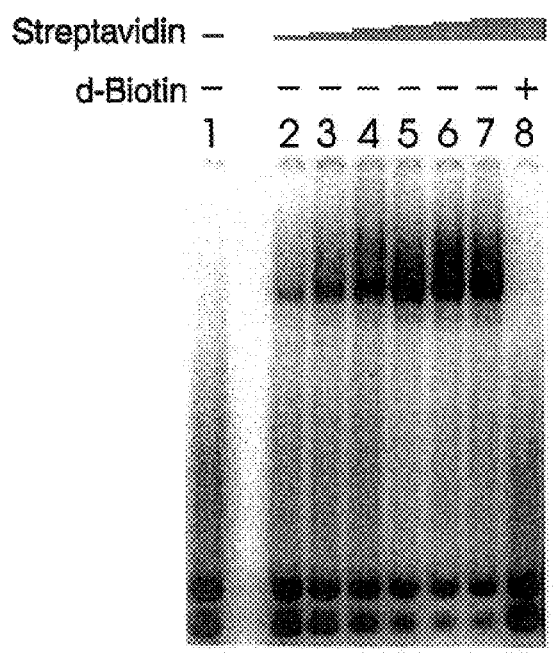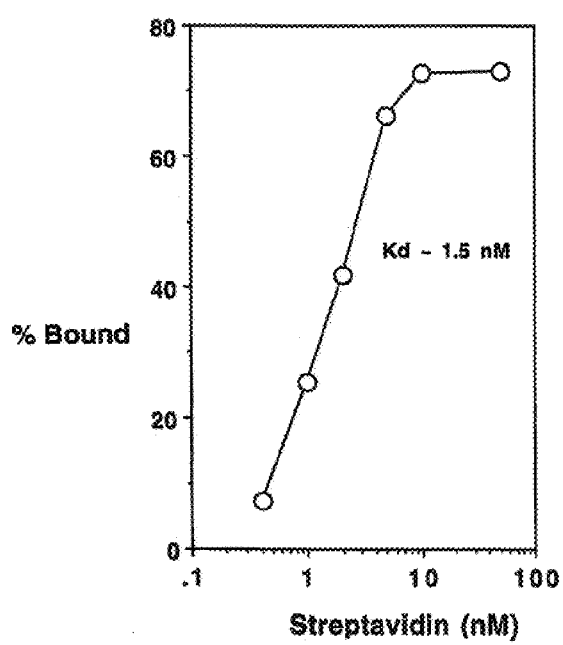
FIG. 6A
FIG. 6B

SEQUENCE LISTING

```
<160> NUMBER OF SEQ ID NOS: 4

<210> SEQ ID NO 1
<211> LENGTH: 10
<212> TYPE: PRT
<213> ORGANISM: Artificial
<220> FEATURE:
<223> OTHER INFORMATION: EP240-Cys peptide

<400> SEQUENCE: 1
```

```
Thr Phe Arg His Ser Val Val Val Pro Cys
1               5                   10

<210> SEQ ID NO 2
<211> LENGTH: 10
<212> TYPE: PRT
<213> ORGANISM: Artificial
<220> FEATURE:
<223> OTHER INFORMATION: EP240S-Cys peptide

<400> SEQUENCE: 2

Thr Phe Val His Val Ser Arg Val Pro Cys
1               5                   10

<210> SEQ ID NO 3
<211> LENGTH: 26
<212> TYPE: DNA
<213> ORGANISM: Artificial
<220> FEATURE:
<223> OTHER INFORMATION: hUBF binding DNA sequence

<400> SEQUENCE: 3
cagtctcctt ctggtctctt ctcagt                                        26

<210> SEQ ID NO 4
<211> LENGTH: 17
<212> TYPE: DNA
<213> ORGANISM: Artificial
<220> FEATURE:
<223> OTHER INFORMATION: U17 probe

<400> SEQUENCE: 4
cggccgtacg ugcgccg                                                  17
```

PROGRAMMABLE GENOTOXIC AGENTS AND USES THEREFOR

RELATED APPLICATIONS

This application is a Continuation-in-Part of co-pending U.S. patent application Ser. No. 08/434,664, filed May 4, 1995, now U.S. Pat. No. 5,879,917, which is a Continuation-in-Part of Ser. No. 08/239,428 filed May 4, 1994, now U.S. Pat. No. 5,882,941.

GOVERNMENT SUPPORT

Work described herein was supported by Federal Grant No. 5R35-CA52127, awarded by the National Institutes of Health. The Government has certain rights in the invention.

FIELD OF THE INVENTION

The present invention relates generally to compounds and methods for the selective destruction of cells in a heterogenous cell population. The compounds feature, in pertinent part, a genotoxic agent that damages cellular DNA.

BACKGROUND OF THE INVENTION

Frequently, a need arises in biological investigations and clinical or veterinary practice for selectively killing a subpopulation of cells in a heterogenous cell population. For example, to attain a strain or culture of cells having desirable characteristics, available in vitro techniques can be applied for selectively killing a subpopulation of cells in a heterogenous cell population that comprises cells that possess a desired characteristic. In this manner, cells that have undesirable characteristics can be eliminated from the population. Hybridoma cell lines producing desired monoclonal antibodies and stable genetic transfectant cell lines expressing the products of heterologous cloned genes are customarily established in this manner. See generally, Sambrook et al., *Molecular Cloning: A Laboratory Manual* (2d ed. 1989). A mixed population of cells comprising the desired hybridoma or transfectant is maintained in culture for a period of time in the presence of one or more genotoxic drugs, such as aminopterin or methotrexate. The desired cells are resistant to the genotoxic effects of the drug employed. In contrast, other cells in the population are susceptible to the drug and fail to survive. These techniques rest on the creation of cells having a defined phenotype that confers resistance to a particular, preselected genotoxic drug. Thus, although significant advances in biology and biotechnology have been achieved through the use of these techniques, limits remain to their flexibility.

Another general context in which practitioners desire to kill cells selectively involves heterogenous cell populations comprising cells of two or more phylogenetically different species of organisms. Here, it may be desirable to destroy selectively the cells of one species while preserving viability of another. In this manner, a desired species can be enriched in the population or an offensive species, such as an infectious agent, can be removed. Here again, the desired objective is often accomplished by treating the cell population with a drug, such as an antibiotic, antiviral, antifungal or antiparasitic drug, to which the undesired species is susceptible. Cells of the undesired species succumb to the effects of the drug and die. Conversely, the desired species (e.g., a human or other host animal) must have the capacity to resist the chosen drug. Although a wide choice of drugs useful for such purposes has historically been available, recent reports have documented the appearance of drug resistance in undesirable species. For example, resistant strains of the organisms responsible for septic wound infections, hospital-acquired infections, tuberculosis, malaria, dysentery and a host of other contagious diseases have arisen in recent years. *Harrison's Principles of Internal Medicine,* Part 5 Infectious Diseases, Ch. 78, 79, and 83–88 (12th ed. 1991). The emergence of such strains greatly complicates the treatment of infection, and limits choices available to the practitioner.

The need to manage or alleviate cancer provides yet another general setting in which practitioners require means for selectively killing cells in a heterogenous cell population. Here, the population comprises normal and neoplastic (malignant or transformed) cells in an individual's tissues. Cancer arises when a normal cell undergoes neoplastic transformation and becomes a malignant cell. Transformed (malignant) cells escape normal physiologic controls specifying cell phenotype and restraining cell proliferation. Transformed cells in an individual's body thus proliferate, forming a tumor (also referred to as a neoplasm). When a neoplasm is found, the clinical objective is to destroy malignant cells selectively while mitigating any harm caused to normal cells in the individual undergoing treatment. Currently, three major approaches are followed for the clinical management of cancer in humans and other animals. Surgical resection of solid tumors, malignant nodules and or entire organs may be appropriate for certain types of neoplasia. For other types, e.g., those manifested as soluble (ascites) tumors, hematopoeitic malignancies such as leukemia, or where metastasis of a primary tumor to another site in the body is suspected, radiation or chemotherapy may be appropriate. Either of these techniques is also commonly used as an adjunct to surgery. *Harrison's Principles of Internal Medicine,* Part 11 Hematology and Oncology, Ch. 296, 297 and 300–308 (12th ed. 1989).

Chemotherapy is based on the use of drugs that are selectively toxic to cancer cells. Id. at Ch. 301. Several general classes of chemotherapeutic drugs have been developed, including drugs that interfere with nucleic acid synthesis, protein synthesis, and other vital metabolic processes. These are generally referred to as antimetabolite drugs. Treatment regimes typically attempt to ensure inactivation of a particular pathway in cancer cell metabolism by coadministering two or more suitable antimetabolite drugs. Other classes of chemotherapeutic drugs inflict damage on cellular DNA. Drugs of these classes are generally referred to as genotoxic. The repair of damage to cellular DNA is an important biological process carried out by a cell's enzymatic DNA repair machinery. Unrepaired lesions in a cell's genome can impede DNA replication or impair the replication fidelity of newly synthesized DNA. Thus, genotoxic drugs are generally considered more toxic to actively dividing cells that engage in DNA synthesis than to quiescent, nondividing cells. In many body tissues, normal cells are quiescent and divide infrequently. Thus, greater time between rounds of cell division is afforded for the repair of damage to cellular DNA in normal cells. In this manner, practitioners can achieve some selectivity for the killing of cancer cells. Many treatment regimes reflect attempts to improve selectivity for cancer cells by coadministering chemotherapeutic drugs belonging to two or more of these general classes.

In some tissues, however, normal cells divide continuously. Thus, skin, hair follicles, buccal mucosa and other tissues of the gut lining, sperm and blood-forming tissues of the bone marrow remain vulnerable to the action of genotoxic drugs. These and other classes of chemotherapeutic drugs can also cause severe adverse side effects in drug-sensitive organs, such as the liver and kidneys. These and other adverse side effects seriously constrain the dosage levels and lengths of treatment regimens that can be prescribed for individuals in need of cancer chemotherapy. Id. at Ch. 301. See also Loehrer and Einhorn (1984), 100 Ann. Int. Med. 704–714 and Jones et al. (1985), 52 Lab. Invest. 363–374. Such constraints can predjudice the effectiveness of clinical treatment. For example, the drug or drug combination administered must contact and affect cancer cells at times appropriate to impair cell survival. Genotoxic drugs are most effective for killing cancer cells that are actively dividing when chemotherapeutic treatment is applied. Conversely, such drugs are relatively ineffective for the treatment of slow growing neoplasms. Carcinoma cells of the breast, lung and colorectal tissues, for example, typically double as slowly as once every 100 days. Id. at Table 301-1. Such slowly growing neoplasms present difficult chemotherapeutic targets.

Moreover, as with the emergence of resistant strains of pathogenic organisms, transformed cells can undergo further phenotypic changes that increase their resistance to chemotherapeutic drugs. Cancer cells can acquire resistance to genotoxic drugs through diminished uptake or other changes in drug metabolism, such as those that occur upon drug-induced gene amplification or expression of a cellular gene for multiple drug resistance (MDR). Id. at Ch. 301. Resistance to genotoxic drugs can also be acquired by activation or enhanced expression of enzymes in the cancer cell's enzymatic DNA repair machinery. Therapies that employ combinations of drugs, or drugs and radiation, attempt to overcome these limitations. The pharmacokinetic profile of each chemotherapeutic drug in such a combinatorial regime, however, will differ. In particular, permeability of neoplastic tissue for each drug will be different. Thus, it can be difficult to achieve genotoxically effective concentrations of multiple chemotherapeutic drugs in target tissues.

Needs remain for drugs that can selectively destroy cells in a heterogenous cell population. Particular needs remain for drugs, including genotoxic drugs, that can selectively destroy cells of a pathogenic or undesired organism while preserving relatively unimpaired the viability of cells of a host or desired organism. Still more poignant needs remain for chemotherapeutic drugs, including genotoxic drugs, that can selectively destroy neoplastic or virally infected cells yet not significantly impair the viability of normal healthy cells in the body of an individual afflicted with cancer or a viral disease.

SUMMARY OF THE INVENTION

It is an object of this invention to provide a heterobifunctional compound that is genotoxic to selected cells in a heterogenous cell population. It is an object of this invention to provide a heterobifunctional compound that inflicts genomic lesions on selected cells in a heterogenous cell population. It is an object of this invention to provide a heterobifunctional compound that inflicts genomic lesions and impairs cellular repair of said lesions in selected cells in a heterogenous cell population. It is an object of this invention to provide a genotoxic agent or drug that can be "programmed" to destroy selected cells that are phenotypically distinguishable from nonselected cells in a heterogenous cell population. Another object of this invention is to expand the range of chemotherapeutic drugs available for the treatment of infectious and neoplastic diseases. Yet another object of this invention is to expand the range of infectious and neoplastic diseases that are susceptible to chemotherapy. These and other objects, along with advantages and features of the invention disclosed herein, will be apparent from the description, drawings and claims that follow.

In one aspect, the invention features a cell membrane permeant heterobifunctional compound suitable for destroying selected cells in a heterogenous cell population. The selected cells possess a cell component, such as a protein, that is absent or is present at significantly diminished levels in other, nonselected cells of the heterogenous cell population. Preferably, the cell component is intracellular. Most preferably, it is located within the cell nucleus or is naturally translocated to the nucleus from another intracellular site. In preferred embodiments, the cell component is a diffusible macromolecule having a molecular weight of at least about 25 kDa, more preferably at least about 40 kDa and still more preferably at least about 80 kDa. The present heterobifunctional compound is actively or passively transported across cell membranes, or diffuses through cell membranes. Thus, it can internalize within cells. It comprises a first agent that binds to cellular DNA to form a genomic lesion. The genomic lesion can be formed at a random or site-specific locus in cellular DNA. In certain embodiments, the first agent damages cellular DNA by forming one or more covalent bonds with nucleotide bases, the sugar-phosphate DNA backbone, or both. In other embodiments, the genomic lesion is formed by intercalation of the first agent into cellular DNA. Optionally, the first agent is a precursor that is converted into a DNA-reactive intermediate spontaneously or by exposure to physiological conditions, a cellular or secreted enzyme, product or byproduct of cellular metabolism, ionizing or nonionizing radiation, light energy, or the like. The genomic lesion so formed by interaction of the first agent with cellular DNA is potentially repairable by the cell's enzymatic DNA repair machinery.

The first agent is linked to a second agent that binds to the cell component that is preferentially present in selected cells of the population. In some embodiments, the first and second agents are linked by a covalent bond. In other embodiments, the first and second agents are linked indirectly by covalent bonds to an organic linker. In still other embodiments, the first and second agents are linked by noncovalent interactions, such as electrostatic or hydrophobic interactions. Thus, in certain embodiments, the first and second agents become linked upon or following binding of the first agent to cellular DNA. The second agent forms a stable complex with the cell component. That is, the second agent interacts specifically with the cell component. Interaction can be noncovalent or covalent, and is energetically favored under intracellular, e.g., nuclear, conditions. As noted, the cell component is preferably a diffusible macromolecule, such as a protein. Alternatively, it can be a metabolite, ligand or cofactor that is specifically bound by a protein or another diffusible macromolecule present in the cell. In either circumstance, the complex comprises a macromolecular cell component found preferentially in the selected cells. The second agent thus localizes a sterically large cell component in the immediate vicinity of the genomic lesion. Preferably, the cell component is large enough to sterically obscure a segment of adjacent nucleosides extending from the lesion site for at least about five base pairs, more preferably at least about eight base pairs, still more preferably at least about twelve base pairs in both the 5' and 3' directions. As a result, the complex between the cell component and the second agent is effective for shielding or inhibiting repair of the genomic lesion formed by the binding of the first agent to cellular DNA. Formation of a sterically large complex at the lesion site hinders access by the cell's enzymatic DNA repair machinery. As a result, shielded lesions persist in the genome and prejudice DNA replication, the expression of genes relevant to cell survival, and the like. Thus, the heterobifunctional compounds of the present invention are fatal to selected cells of the heterogenous cell population.

In certain embodiments, the second agent interacts specifically with a cell component that is relevant to the survival or proliferation of the selected cells. For example, the second agent can interact with a regulatory protein or enzyme involved in the control of cell proliferation. These include, but are not limited to, oncogene products (e.g., myc, ras, abl, and the like), tumor suppressor gene products (e.g., the nuclear phosphoprotein p53), and proteins that regulate initiation and progress through the cell cycle (e.g., cyclins and cyclin-dependent kinases). Alternatively, the second agent can interact with a transcription factor that controls or modulates the expression of one or more genes that are relevant to metabolic or secretory processes carried out by the selected cell. One such transcription factor is upstream binding factor (UBF), which controls the expression of ribosomal RNA genes and thus is pivotal to the function of the cell's protein synthesis machinery. Second agents that specifically interact with transcription factors preferably mimic or resemble the natural genomic binding site for the particular transcription factor. That is, the transcription factor binds to the second agent with an affinity near (e.g., within about 100-fold) or preferably exceeding its affinity for the natural genomic binding site. Such second agents are referred to herein as "transcription factor decoys". Certain transcription factors, in addition to binding an endogenous genomic binding site, also bind to soluble ligands. Binding of these transcription factors to their cognate ligands modulates binding of the transcription factors to their endogenous genomic binding sites. That is, ligand binding confers or abrogates ability of the transcription factor to bind its cognate genomic site, or enhances or suppresses its ability to do so. Such transcription factors are accordingly referred to herein as ligand-responsive transcription factors. They have sometimes been referred to in the art as intracellular or nuclear receptors for soluble ligands. Second agents that recognize and bind to these transcription factors can mimic an activating or repressing ligand, such as estrogen or an estrogen analog or derivative. Heterobifunctional compounds comprising transcription factor decoys or ligand mimics thus are doubly fatal to the selected cell.

In another aspect, the present invention provides a method for the destruction of selected cells in a heterogenous cell population. The heterogenous cell population can comprise phenotypically distinguishable cells of a single phylogenetic species, or cells of two or more different phylogenetic species. The phylogenetic species can be unicellular or multicellular. The population can comprise cells in culture, cells withdrawn from a multicellular organism (e.g., a blood sample or tissue biopsy), or cells present in tissue or organs of a multicellular organism. It should be understood that the term "multicellular organism" embraces mammals, including humans. The heterogenous cell population can comprise cells of both normal and transformed phenotypes. Thus, the population can comprise neoplastic or malignant cells. In the present method, selected cells of the heterogenous population are killed. "Selected cells" are phenotypically distinguishable from other, nonselected cells in the heterogenous population in that they possess a cell component that is absent or is present at significantly diminished levels in nonselected cells. For example, the cell component is made or accumulates in the selected cells to levels that are about 5-fold in excess of the levels of the same or a similar cell component in nonselected cells. Preferably, the selected cells possess about a 10-fold excess of the cell component. More preferably, the selected cells possess about a 100-fold or higher excess of the cell component. In certain embodiments, the cell component is the expression product of a cellular or viral oncogene. In certain other embodiments, the cell component is the expression product of a mutant tumor suppressor gene. In still other embodiments, the cell component is a regulatory or enzymatic element of a nuclear protein complex that controls initiation of or progress through the cell cycle.

The present method involves contacting the heterogenous cell population with the cell membrane permeant heterobifunctional compound described herein. The population is incubated with the compound for a period of time sufficient for the compound to cross cell membranes and internalize within cells, including the selected cells. The first agent of the compound binds to cellular DNA, inflicting a genomic lesion. As noted above, the genomic lesion is potentially repairable. In selected cells, the second agent of the compound binds to the cell component, forming a complex at the genomic lesion site that sterically hinders access to the lesion by the cell's DNA repair machinery, thereby inhibiting repair or "shielding" the lesion. As a result, genomic lesions persist in the selected cells and contribute to their demise. That is, the present compound is preferentially genotoxic to the selected cells. In contrast, lesions in nonselected cells do not form complexes at the site of the genomic lesion, or form complexes with much lower frequency than in selected cells. Lesions in nonselected cells are therefore predominantly unshielded and remain accessible to the cellular DNA repair machinery. As a result, genomic lesions in nonselected cells are repaired. Lesion repair contributes to the survival of the nonselected cells. That is, the present compounds are relatively less genotoxic to nonselected cells. It is understood herein that the present compounds also may be internalized selectively by selected cells, regardless of whether the intracellular complex indeed is formed at the genomic lesion site. Selective internalization is expected to arise from the influence of intracellular complex formation in selected cells on chemical equilibrium dynamics between extracellular and intracellular levels of the present genotoxic compounds. Thus, the compounds of the present invention can be used to enhance selectively the uptake of DNA damaging first agents by selected cells in a heterogenous cell population. This process further contributes to the demise of selected cells.

As a result of the present method, the heterogenous cell population becomes depleted of selected cells. Embodiments of the present method wherein the selected cell component that is sequestered at the lesion site is a transcription factor are referred to as "transcription factor hijacking". In such embodiments, hijacking or sequestration of the transcription factor by the second agent at sites other than the factor's natural genomic binding site still further contributes to the death of selected cells, by inducing disarray in one or more of the cell's metabolic or secretory functions.

An advantage of the invention described herein is that heterobifunctional compounds can be engineered that are selectively fatal (genotoxic) to a great phenotypic and phylogenetic variety of selected cells. The term, "programmable genotoxic drugs" thus aptly sums up the flexibility and adaptability of the inventive concept disclosed herein.

BRIEF DESCRIPTION OF THE DRAWINGS

The foregoing and other objects, features and advantages of the present invention, as well as the invention itself, will be more fully understood from the following description of preferred embodiments, when read together with the accompanying drawings, in which:

FIG. 6 presents autoradiograph results demonstrating binding of streptavidin to U-17 monoadducted with a heterobifunctional TMP-biotin conjugate. Panel A presents an autoradiograph of the results of a gel mobility shift assay. 3200 cpm (~0.1 nM) of the radiolabeled TMP-biotin lesioned DNA was used in each lane. 0 nM, 0.4 nM, 1 nM, 2 nM, 5 nM, 10 nM, 50 nM and 50 nM of streptavidin were used in lanes 1 to 8 respectively. In lane 8, free d-biotin was also added to the final concentration of 0.4 nM. Panel B is a binding curve created by plotting the percentages of bound probe (Panel A) against streptavidin concentrations.

DETAILED DESCRIPTION OF PREFERRED EMBODIMENTS

Figure 1:
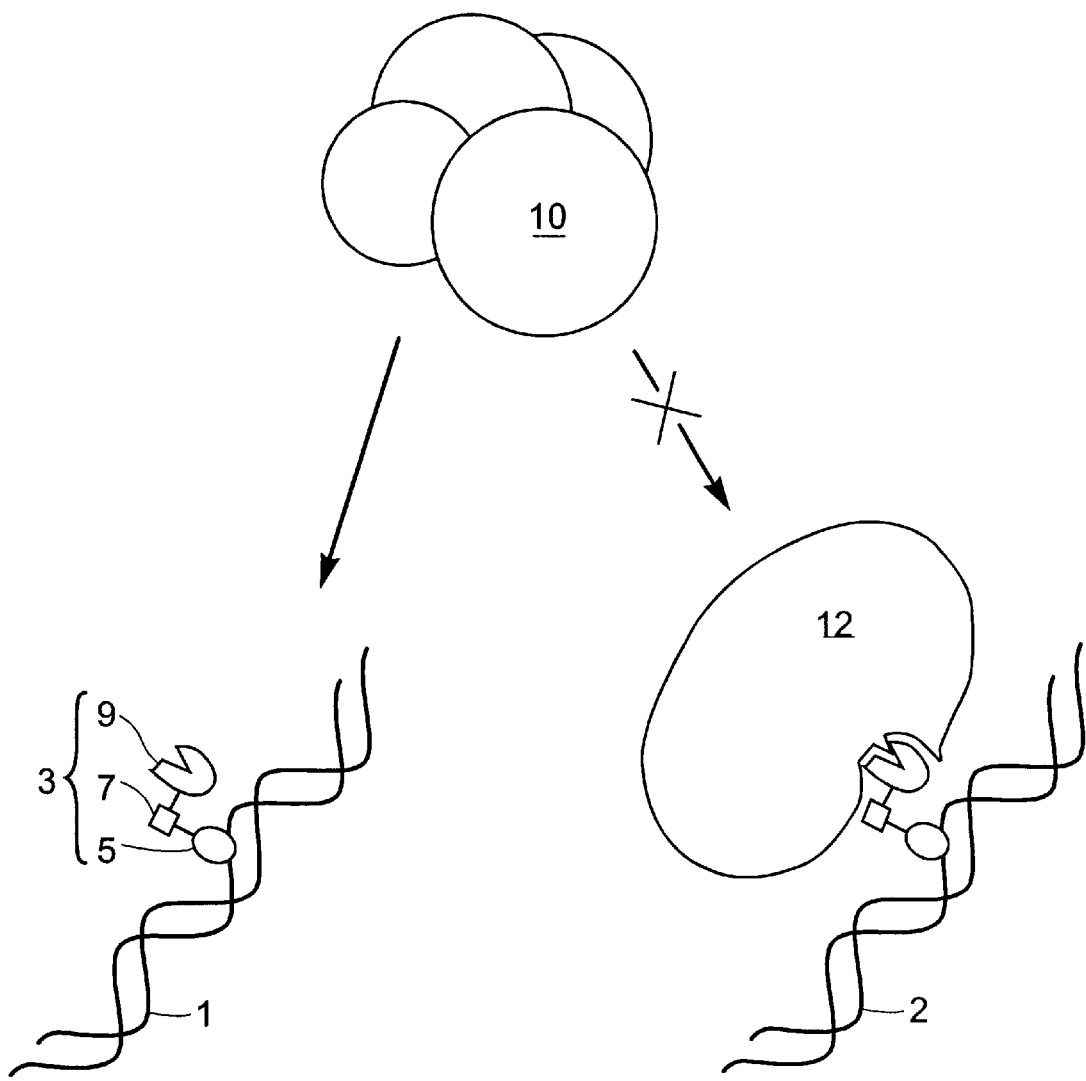
FIG. 1 is a schematic illustration showing basic features of the heterobifunctional programmable genotoxic compounds of the present invention and their anticipated mode of action in mediating steric hinderance of the repair of genomic lesions.

Broadly, the selectively genotoxic compounds disclosed herein comprise a first agent that inflicts genomic lesions on cellular DNA, linked to a second agent that attracts or sequesters, preferably at the genomic lesion site, a sterically large cell component preferentially present in selected cells of a heterogenous cell population. The cell component is sterically large enough to effectively hinder access to the lesion site by elements of the cell's enzymatic DNA repair machinery, thereby shielding the lesion from repair. In preferred embodiments, the cell component is a protein, such as a cell cycle control factor, a transcription factor, an oncogene product or a mutant tumor suppressor gene product, that is normally engaged in the control of one or more genes relevant to the cell's growth or survival, or to secretory processes carried out by the selected cell. FIG. 1 illustrates the basic principle of repair shielding by the heterobifunctional "programmable genotoxic" compounds of the present invention. A heterobifunctional compound 3 of the present invention is shown bound to cellular DNA of a nonselected cell 1 or of a selected cell 2. In each cell, binding of the compound to cellular DNA results in a potentially repairable genomic lesion. The compound 3 comprises a first agent 5 that binds to cellular DNA, linked, optionally by linker 7, to a second agent 9 that binds to a cell component 12 preferentially present in selected cells of a heterogenous cell population comprising selected and non-selected cells. If unrepaired, the genomic lesion contributes to the destruction of cells. Lesion repair is carried out by the cell's enzymatic DNA repair machinery, which includes one or more sterically large repair enzymes 10. In the absence of the cell component 12, repair enzymes 10 access and repair the lesion. However, in selected cells, the cell component 12 binds to the second agent 9, effectively shielding the lesion from repair by presenting a steric obstacle to repair enzyme 10 access.

Genotoxic Agents Useful as First Agents

The present compounds employ as first agent 5, genotoxic drugs that preferably are known in the art and can readily be prepared according to published techniques, or are commercially available. Many of these genotoxic drugs currently are used to treat infections and neoplastic diseases in mammals, e.g., humans. Analogs or derivatives of these drugs readily can be prepared that are suitable for linkage to cell component binding second agent 9 to obtain heterobifunctional genotoxic compound 3 of the present invention. It is anticipated that novel genotoxic drugs also can be developed that will be suitable for use as first agents herein. Compounds comprising such novel first agents are considered to be encompassed by the present invention.

Two general classes of compounds that are suitable for use as first agent 5 are DNA alkylating agents and DNA intercalating agents. Optionally, the first agent can be a precursor that becomes reactive with cellular DNA spontaneously or following exposure to an activating stimulus, such as a cellular or secreted enzyme, cell metabolite or metabolic byproduct, ionizing or nonionizing radiation, light energy, etc. For example, the first agent can be photoactivated. One class of photoactivatable first agents is represented by the drug psoralen, a tricyclic furocoumarin that produces pyrimidine base adducts and crosslinks in cellular DNA. Tricyclic furocoumarin analogs and derivatives of psoralen can also be used as first agents. Thus, for example, trimethylpsoralen (TMP) can be used herein. Psoralens are known to be useful in the photochemotherapeutic treatment of cutaneous diseases such as psoriasis, vitiligo, fungal infections and cutaneous T cell lymphoma. *Harrison's Principles of Internal Medicine,* Part 2 Cardinal Manifestations of Disease, Ch. 60 (12th ed. 1991). Another class of photoactivatable first agents is represented by dacarbazine and includes analogs and derivatives thereof.

Another general class of first agents, members of which can alkylate or intercalate into DNA, includes synthetically and naturally sourced antibiotics. Of particular interest herein are antineoplastic antibiotics, which include but are not limited to the following classes of compounds represented by: amsacrine; actinomycin A, C, D (alternatively known as dactinomycin) or F (alternatively KS4); azaserine; bleomycin; carminomycin (carubicin), daunomycin (daunorubicin), or 14-hydroxydaunomycin (adriamycin or doxorubicin); mitomycin A, B or C; mitoxantrone; plicamycin (mithramycin); and the like. Each class of antineoplastic antibiotics includes analogs and derivatives of the foregoing representative compounds. Antineoplastic antibiotics are known to be useful in the treatment of a variety of neoplasms and viral diseases. Neoplasias currently manageable by the foregoing include leukemias, lymphomas, myelomas, neuroblastomas, neoplasias of bladder, testicular, endometrial, gastric, or lung origin, and others listed in Tables 301-6 and 301-7 of *Harrison's Principles of Internal Medicine,* Part 11 Hematology and Oncology (12th ed. 1991). A given neoplasm is "manageable" by a given drug if treatment with the drug alone or in combination with another drug confers some clinically recognized benefit on the afflicted individual. Optimally, a partial or total remission is achieved. Drugs that contribute to a stabilization of the individual's clinical status or slow the progress of disease, however, are also considered beneficial and are used in the management of neoplasias.

Still another general class of first agents, members of which alkylate DNA, includes the haloethylnitrosoureas, especially the chloroethylnitrosoureas. Representative members of this broad class include carmustine, chlorozotocin, fotemustine, lomustine, nimustine, ranimustine and streptozotocin. Haloethylnitrosourea first agents can be analogs or derivatives of any of the foregoing representative compounds. Neoplasias currently manageable by the foregoing include Hodgkin's, non-Hodgkin's and Burkitt's lymphomas, myelomas, glioblastomas and medulloblastomas, pancreatic islet cell carcinomas, small cell lung carcinomas and the like. Id.

Yet another general class of first agents, members of which alkylate DNA, includes the sulfur and nitrogen mustards. These compounds damage DNA primarily by forming covalent adducts at the N7 atom of guanine. Representative members of this broad class include chlorambucil, cyclophosphamide, ifosfamide, melphalan, mechloroethamine, novembicin, trofosfamide and the like. Nitrogen mustard or sulfur mustard first agents can be analogs or derivatives of any of the foregoing representative compounds. Nitrogen mustards are generally understood to comprise the moiety $N(CH_2H_2X)_2$, wherein X is a halogen, preferably chlorine. In mechloroethamine, X is chlorine, and the moiety is covalently bonded to a methyl ($CH_3$) group. Typically, then, nitrogen mustards such as chorambucil and mephalen have two reactive groups that can form covalent bonds with the N7 atoms of guanine residues. Thus, these drugs can form intrastrand or interstrand DNA crosslinks, and can crosslink DNA to nucleophilic atoms in proteins. Each type of genomic lesion is thought to contribute to the lethal effects of nitrogen mustards. Neoplasias currently manageable by the foregoing include Hodgkin's, non-Hodgkin's, Burkilt's and other lymphomas, leukemias, myelomas, medullomas, neuroblastomas, small cell lung carcinoma, osteogenic sarcoma, neoplasias of breast, endometrial and testicular tissue, and the like. Id. U.S. Pat. No. 3,299,104 (issued Jan. 17, 1967) and Niculescu-Duvaz et al. (1967), *J. Med. Chem.* 172–174, disclose estrogen, progesterone, androgen and steroid conjugates of mechloroethamine. Muntzing and Nilsson (1972), 77 *J. Krebsforch.* 166–170, report histologic studies conducted on cells of patients receiving one such conjugated methochloroethamine compound.

Yet a further general class of first agents, members of which form covalent DNA adducts, includes heavy metal coordination compounds, including platinum compounds. Generally, these heavy metal compounds bind covalently to DNA to form, in pertinent part, cis-1,2-intrastrand dinucleotide adducts. Generally, this class is represented by cis-diamminedichloro-platinum(II) (cisplatin), and includes cis-diammine-(1,1-cyclobutane-dicarboxylato)platinum(II) (carboplatin), cis-diammino-(1,2-cyclohexyl)-dichloroplatinum(II), and cis-(1,2-ethylene-diammine) dichloroplatinum(II), Platinum first agents include analogs or derivatives of any of the foregoing representative compounds. Neoplasias currently manageable by platinum coordination compounds include testicular, endometrial, cervical, gastric, squamous cell, adrenocortical and small cell lung carcinomas along with medulloblastomas and neuroblastomas. trans-Diamminedichloroplatinum (II)

(trans-DDP) is clinically useless owing, it is thought, to the rapid repair of its DNA adducts. The use of trans-DDP as a first agent herein likely would provide a compound with low toxicity in nonselected cells, and high relative toxicity in selected cells.

Other classes of first agents, members of which alkylate DNA, include the ethylenimines and methylmelamines. These classes include altretamine (hexamethylmelamine), triethylenephosphoramide (TEPA), triethylenethiophosphorarnide (ThioTEPA) and triethylenemelamine. Additional classes of DNA alkylating first agents include the alkyl sulfonates, represented by busulfan; the azinidines, represented by benzodepa; and others, represented by, e.g., mitoguazone, mitoxantrone and procarbazine. Each of these classes includes analogs and derivatives of the respective representative compounds.

Oligonucleotides or analogs thereof (e.g., phosphorothioate oligonucleotides, oligonucleotides incorporating $O^6$-methylguanine and/or $O^4$-methylguanine and the like) that interact covalently or noncovalently with specific sequences in the genome of selected cells can also be used as first agents, if it is desired to select one or more predefined genomic targets as the locus of a genomic lesion. Suitable oligonucleotides that intercalate nonclassically into cellular DNA to form triple helices or other complex structures are disclosed in Riordan and Martin (1991), 350 *Nature* 442–443, the teachings of which are incorporated by reference. These compounds are expected to be useful for the management of neoplasias whose growth characteristics are traceable to the aberrant activation of particular genes, such as cyclin genes, oncogenes and mutant tumor suppressor genes.

Each of the foregoing classes of suitable first agents comprises analogs and derivatives of the representative compounds mentioned herein. An analog of a representative compound can be a structurally related compound, optionally a precursor of a representative compound or a derivative of a precursor. For example, trimethylpsoralen (TMP) is an analog of the representative compound psoralen. An analog can also be a known or novel compound bearing substituents that are structurally and/or functionally analogous to those of a representative compound. For example, if a representative compound has a chlorine substituent, an analog can have another halogen substituent (e.g., bromine or fluorine). A known or novel derivative of a representative compound is chemically, physicochemically or metabolically synthesized from a representative compound, and can comprise a greater or lesser number and complexity of substituents than the representative compound. Appropriate substituents to the basic structure of the representative compounds in each class will be known or can be determined through no more than routine experimentation or comparative inspection of the structures of two or more representative members of a particular class. Substitutents suitable for use in the various classes of first agents listed above thus include linear, branched or cyclic alkyl, aryl or mixed alkyl and aryl groups; organic or inorganic acids, bases or neutral moieties. Substituents present in analogs and derivatives of the representative compound can modulate DNA binding activity (e.g., enhance or impair activity), but should not abrogate such activity.

Preferred Classes of Cell Components Bound by Second Agent 9

Turning to second agent 9 of heterobifunctional compound 3, it should be noted that, in all preferred embodiments, the second agent serves to mediate attachment of a cellular macromolecule preferably to the site of genomic damage caused by binding of the first agent 5 to cellular DNA. The bound cellular macromolecule thus preferably sterically shields the lesion from repair. The second agent either binds directly to the cellular macromolecule, or to a ligand, cofactor or metabolite to which the cellular macromolecule in turn binds with high affinity. In either circumstance, the second agent mediates formation of a stable complex between the cellular macromolecule and the heterobifunctional compound. As the complex is stable under intracellular, e.g., nuclear, conditions, it preferably acts as a persistent steric shield, preventing repair of the genomic lesion for a sufficiently long period of time for the lesion to contribute to the demise of selected cells.

In preferred embodiments, the second agent binds directly to a cell component that is a macromolecule, such as a protein, preferentially associated with selected cells in a heterogenous cell population. This protein provides a phenotypic distinction between selected and nonselected cells of the population. It can be a protein of endogenous cellular origin (expressed from the cellular genome), or of viral origin (expressed from the genome of a virus infecting the selected cells). Selected cells are phenotypically distinguished from nonselected cells by the qualitative or quantitative association of the second agent-recognized protein. Thus, nonselected cells lack the protein, or are associated with diminished amounts thereof. The recognized protein can be a phylogenetic species or tissue-type variant of a corresponding protein associated with nonselected cells. It can be a protein, the expression of which is developmentally regulated or dysregulated in selected cells in a manner different from its regulation in nonselected cells. It can also be a mutant of a protein normally associated with nonselected cells. Examples of recognized proteins thus include bacterial, fungal, parasitic and viral intracellular proteins. Other examples include developmental stage specific proteins, including proteins expressed upon dedifferentiation or malignant transformation of nonselected cells into selected cells. Still other examples include proteins preferentially expressed by dividing cells, or proteins that are relevant to the process of cell division (cell cycling). Other examples include proteins that can be induced in selected cells by irradiation or other stimuli to which selected cells respond.

Selected cells with which the second-agent recognized protein is associated, therefore, can be dividing cells, e.g., transformed cells. Preferably, selected cells have at least about a 5-fold excess of the recognized protein, over the amount of the same or a corresponding protein in nonselected cells. More preferably, the excess is at least about 10-fold. Still more preferably, the excess exceeds about 100-fold. Even more preferably, the recognized protein is undetectable in nonselected cells. In many preferred embodiments, the recognized protein is intracellular. For example, the recognized protein is a nuclear protein or is a protein that is normally translocated to the nucleus, e.g., when bound to a transport protein or an activating or suppressing ligand. Preferred classes of second agent-recognized intracellular proteins therefore include but are not limited to cyclins, cyclin dependent kinases, oncogene products, mutant tumor suppressor gene products, and transcription factors.

Oncogenes are genes encoding proteins that are relevant to the process of malignant transformation of a normal cell into a malignant (cancerous) cell. Thus, oncogenes encode proteins relevant to the proliferation and differentiation states of a cell. *Molecular Cell Biology*, Ch. 24 Cancer, 967 and 984–994 (2d ed. 1990). Oncogenes can be found in the cellular genome, or in the genome of a virus infecting the cell. Infection with certain tumorigenic viruses causes the infected cell to undergo malignant transformation. Examples of such viruses include the adenoviruses and papovaviruses (e.g., SV40 and polyoma), retroviruses (e.g., Rous sarcoma virus, mouse mammary tumor virus, human T-cell leukemia virus-1, Epstein-Barr virus, and the papilloma viruses). Id., Ch. 24 Cancer, 967–980. Oncogenes encoding intracellular proteins (e.g., src, yes, fps, abl, met, mos and crk), particularly those encoding nuclear proteins (e.g., erbB, abl, jun, fos, myc, N-myc, myb, ski and rel) are of particular interest herein. Id. at Table 24-1. That is, certain preferred second agents 9 bind to nuclear oncogene products. Oncogenes of both viral and cellular origin have been implicated in the etiology of numerous neoplasias. *Harrison's Principles of Internal Medicine,* Part 1 Biological Basis of Disease, Ch. 10 (12th ed. 1991). These include, but are not limited to Burkitt's lymphoma (Epstein-Barr virus; activation of endogenous myc), chronic myelogenous leukemia (activation of abl), anogenital cancers (papilloma viruses), and pancreatic carcinomas (ras). Id. at Table 10-3.

Tumor suppressor genes are also known as "anti-oncogenes" or "repressive oncogenes" because they encode proteins (gene products) that affirmatively maintain cells in an appropriately differentiated state, and/or restrain cells from embarking on unbridled rounds of proliferation. These desirable properties can be lost upon mutation of a tumor suppressor gene, freeing the cell from normal growth controls. Tumor suppressor gene products are thought to bind either to cellular DNA (and thus may themselves be transcription factors), or to other proteins, e.g., oncogene products. Two examples of tumor suppressor genes are Rb, the retinoblastoma gene (*Molecular Cell Biology,* Ch. 24 Cancer, 996 (2d ed. 1990); *Harrison's Principles of Internal Medicine,* Part 1 Biological Basis of Disease, Ch. 10, 68–69) and the nuclear phosphoprotein p53 (Hollstein et al. (1991), 253 *Science* 49–53). p53 is of particular interest herein, as somatic mutations of p53 have been reported in sporadic and inherited neoplasms of breast, colon, lung, esophagus, liver, brain, blood-forming (myeloid and lymphoid), reticuloendothelial and other tissues (Id.). Indeed, somatic mutations of p53 are thought to play a role in up to one-half of all new malignancies documented yearly in Britain and the United States, making this protein the most frequent target for mutation in human cancers (Vogelstein (1990), 348 *Nature* 681–682; Marx (1990), 250 *Science* 1209). Studies investigating germ-line mutations of p53 in familial Li-Fraumeni syndrome, an inherited susceptibility to cancers associated with p53 mutation, have shown that small deletions, transpositions and point mutations affecting conserved regions of the protein convert p53 from a suppressive growth regulatory protein into a transdominant oncogene, which can bind to and inactivate wildtype p53 (Gannon et al. (1990), 9 *EMBO J.* 1595–1602; Malkin et al. (1990), 250 *Science* 1233–1238; and Srivastava et al. (1990), 348 *Nature* 747–749). Second agents 9 which bind to mutant, but not wildtype, p53 are accordingly preferred in certain embodiments of the present invention. The precise nature and locations of transforming mutations in p53 has been the subject of intense investigation, and is reviewed in Hollstein et al. (1991), 253 *Science* 49–53, the teachings of which are herein incorporated by reference. At least one monoclonal antibody, PAb240, that recognizes mutant but not wildtype p53 has been isolated, and the recognized epitope characterized (Gannon et al. (1990), 9 *EMBO J.* 1595–1603; Stephen and Lane (1992), *J. Mol. Biol.* 577–580; the teachings of both of which are incorporated herein by reference). Second agents 9 that bind the epitope recognized by PAb240 are particularly preferred in certain embodiments of the invention.

Cyclins, cyclin dependent kinases, and cyclin associated proteins together form nuclear complexes that control initiation and progress through the cell cycle. Keyomarsi and Pardee (1993), 90 *Proc. Natl. Acad. Sci. USA* 1112–1116, and Xiong et al. (1993), 7 *Genes and Dev.* 1572–1583, the teachings of each of which are incorporated herein by reference. Cyclins and cyclin dependent kinases are classified, according to the presence therein of conserved amino acid sequence motifs, as members of evolutionarily conserved multigene families that determine and regulate cell proliferation. The particular cyclins and cyclin dependent kinases that are associated in nuclear cell cycle control complexes shift subtly at different stages of the cell cycle (e.g., upon transition from $G_1$ to S or upon transition from $G_2$ to M). Xiong et al. report that expression and association patterns of cyclins and associated proteins are deranged in transformed cells. Thus, as for tumor suppressor gene products, malignant transformation may be associated with the inappropriate display of a cryptic epitope in one or more cyclins, cyclin dependent kinases or cyclin associated proteins. Such a cryptic epitope might prevent normal association between cyclins and cyclin dependent kinases, or might promote inappropriate associations. In certain embodiments, then, second agents 9 of the present heterobiflnctional compounds bind selectively to such cryptic cyclin-related epitopes. Keyomarsi and Pardee report that one cyclin, Cyclin E, is significantly overexpressed in breast carcinoma cells, relative to its expression level in normal breast tissue. Accordingly, the accumulation of cyclin E offers a phenotypic distinction between selected (transformed) and nonselected (normal) cells in breast tissue. In certain embodiments, second agents 9 of the present invention that bind to Cyclin E thus offer the ability to selectively destroy breast carcinoma cells.

Transcription factors are proteins that bind to specific sites in cellular DNA (e.g., specific sequences, structures or a combination thereof) and thereby regulate the expression of one or more genes. Such sites in the cellular DNA are referred to herein as endogenous genomic binding sites. Transcription factors can, by binding to their cognate endogenous genomic binding sites, promote, enhance or repress gene expression. *Molecular Cell Biology,* Ch. 11 Gene Control and Development in Eukaryotes, 400–412 (2d ed. 1990). Transcription factors can be grouped into the following classes, based upon similarities in protein structure in the regions thought to interact with DNA: helix-turn-helix or homeobox proteins; zinc-finger proteins; and amphipathic helical proteins, such as leucine-zipper proteins. Second agents can thus be designed according to the principles set forth herein to bind to one or more structurally similar transcription factors. In some embodiments, second agents mimic soluble modulating ligands that affect the binding of ligand-responsive transcription factors, such as the estrogen receptor, to the factor's endogenous genomic binding site. In other embodiments, second agents mimic the endogenous genomic binding sites. Such binding site mimics are referred to herein as transcription factor decoys or ligand decoys. Binding affinity of a given transcription factor for a decoy is preferably near the affinity of the factor for its endogenous genomic binding site or modulating ligand. That is, binding affinity of the factor for the decoy is within about 100-fold of its affinity for the cognate site or ligand (e.g., if $K_{d(app)}$ for the cognate site is 1 nM, the $K_{d(app)}$ for the decoy is at most about 100 nM). Preferably, affinity of the decoy is within about 10 fold that of the cognate site or ligand. More preferably, affinity of the decoy exceeds that of the cognate site or ligand. Particular transcription factor decoys that mimic the sequences of endogenous genomic binding sites for particular transcription factors are disclosed in Bielinska et al. (1990), 250 *Science* 997–1000, and in Chu and Orgel (1992), 20 *Nucl. Acids Res.* 5857–5858, the teachings of each of which are incorporated herein by reference. The present invention extends these teachings to encompass transcription factor decoys that mimic the structures of endogenous genomic binding sites for transcription factors, including structures that are sequence-independent.

In appropriate embodiments, second agents 9 are employed that are decoys for transcription factors that control the expression of genes relevant to the growth or survival of selected cells, or to metabolic or secretory processes carried out by selected cells. Exposure of selected cells to such compounds results in transcription factor hijacking. That is, a transcription factor bound to the decoy is titrated away from its natural genomic binding site and becomes sequestered at the site of a genomic lesion. Preliminary studies were carried out to confirm that a vital transcription factor could be "hijacked" in this manner and caused to bind to a genomic lesion. These preliminary studies demonstrated that an HMG box transcription factor, upstream binding factor (UBF), binds to cisplatin 1,2-d (GpG) intrastrand crosslinks (G^G) and to its natural genomic binding site with comparable affinities. For these studies, human upstream binding factor (hUBF) was used. hUBF binds to the upstream control element or UCE of the human ribosomal RNA (rRNA) promoter and is an important positive regulator of rRNA transcription (Jantzen et al. (1990), 344 *Nature* 830–836). rRNAs are required elements of the cellular protein synthesis machinery. Thus, hUBF/promoter binding is relevant to the proper functioning of the cell's protein synthesis machinery.

Figure 5:
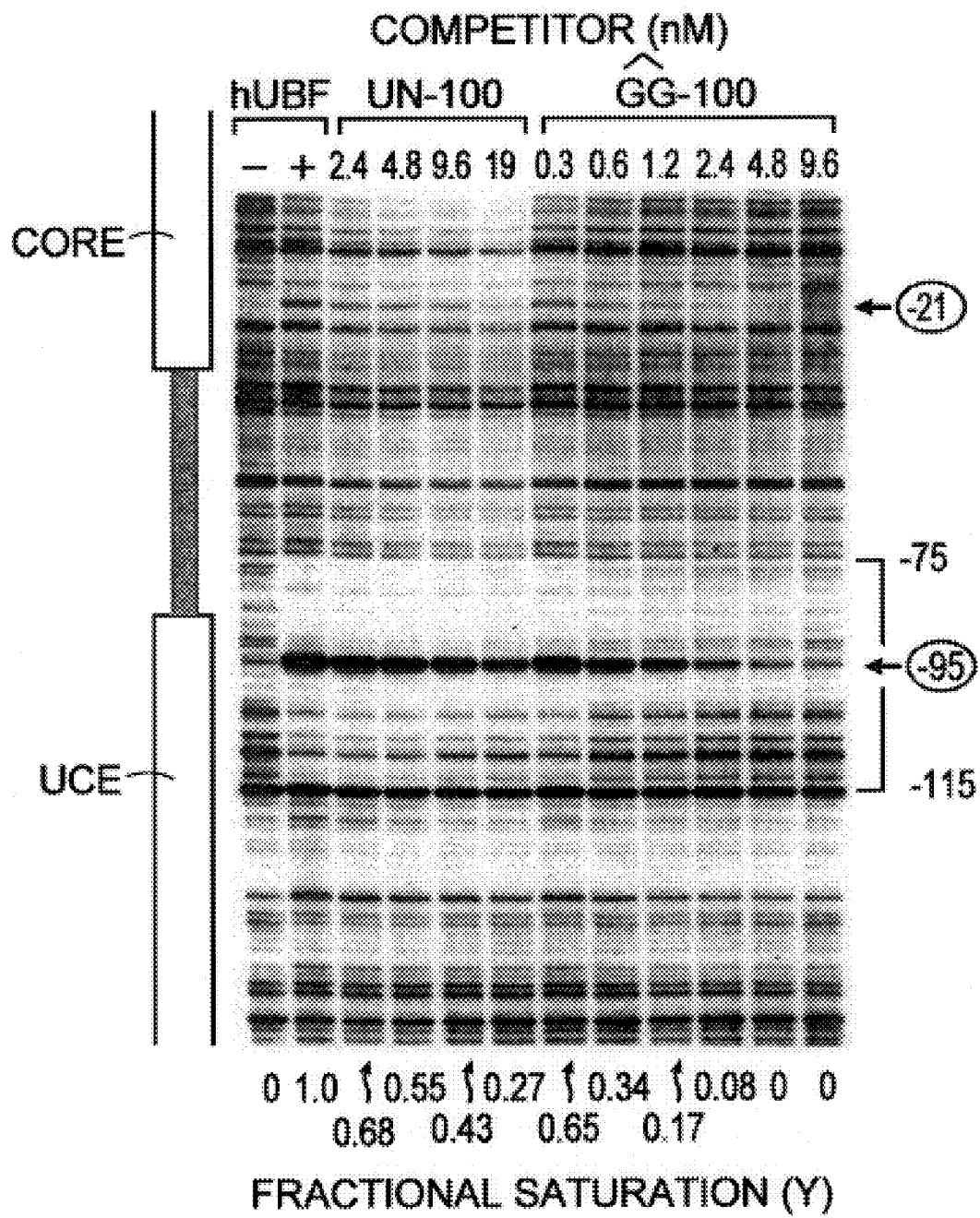
FIG. 5 presents autoradiograph results of additional footprinting studies that revealed similarity in the hUBF-protected regions of this transcription factor's cognate genomic binding site and the cisplatin decoy (compare FIG. 3).

It should be noted that the particular nucleic acid used as an hUBF decoy in the preliminary studies lacked sequence similarity to the sequence of the endogenous genomic binding site for hUBF; thus, transcription factor hijacking was accomplished by structural, rather than sequence-specific, recognition. Southwestern and Western blot analysis yielded results, presented in FIG. 2, showing that in vitro translated hUBF bound to DNA globally modified by cisplatin but failed to recognize unmodified DNA or DNA containing adducts of the genotoxically inactive isomer, trans-DDP. Proteins in crude HeLa cell extracts having molecular weights that correlate to the known sizes of hUBF species displayed a similar binding preference. DNase I footprinting analysis (FIG. 3) of the cisplatin-modified nucleic acid decoy showed that hUBF protected the 14 bp DNA region that symetrically flanks the site of a defined cisplatin G^G adduct (Panel A, Lane 1). These results directly demonstrate that hUBF binding prevented access to the cisplatin lesion site by a sterically large DNA processing enzyme. Competition studies (results presented in FIG. 5) established that the cisplatin decoy efficiently inhibited the formation of [hUBF-promoter] complexes. That is, the structural decoy was shown to be an effective competitive inhibitor of the proper binding of hUBF to its cognate, sequence specific, genomic binding site (the UCE). The affinity of hUBF for G^G was substantial ($K_{d(app)}$=60 pM; see FIG. 3, Panel B). For comparison, the $K_{d(app)}$ of another HMG box protein, HMG1, for the cisplatin G^G adduct has been shown to be 370 nM (Pil and Lippard (1992), 256 *Science* 234–237). FIG. 5 also reveals a significant nonspecific binding component of hUBF for its promoter. This is also observed with other HMG box proteins, including lymphoid enhancer factor-1 (LEF-1), which binds with nominal specificity (20–40 fold) to its putative genomic recognition sequence (Giese et al. (1991), 5 *Genes & Dev.* 2567–2578). Footprinting studies (results presented in FIG. 5) also established similarity between the hUBF protected regions of the cognate genomic binding sequence (the UCE) and the cisplatin decoy. From these results, it can be predicted that the levels of cisplatin that accumulate in cellular DNA in vivo upon treatment of a cancer patient with a cisplatin chemotherapeutic regime are sufficient to titrate hUBF away from the ribosomal RNA promoter.

The above-summarized preliminary studies lend insight into the structural features of hUBF-cisplatin decoy complexes. The cisplatin adduct was approximately centered within the 14 bp protected region (FIG. 3), suggesting that the DNA binding domain(s) is symmetrically placed relative to the adduct. As discussed hereinabove, cisplatin adducts cause structural distortions in duplex DNA. 1,2-Dinucleotide adducts are bent and partially unwound in the area immediately associated with the platinum coordination complex. The resulting angular structure thus has an "elbow" at the lesion site. This elbow appears to remain solvent exposed, even when the lesion is shielded by bound hUBF: the phosphodiester bond immediately 5' to the lesion remained sensitive to DNase I. This result is consistent with binding of hUBF to the minor groove of duplex DNA, on the convex side of the DNA bend. Others have reported similar findings concerning the binding of other HMG box transcription factors, particularly LEF-1 and SRY (the testis determining factor) to their cognate genomic binding sites through minor groove interactions (Giese et al. (1991), 5 *Genes & Dev.* 2567–2578; van de Wetering and Clevers (1992), 11 *EMBO J.* 3039–3044; King and Weiss (1993), 90 *Proc. Natl. Acad. Sci. U.S.A.* 11990–11994).

hUBF, like SRY, exhibits both sequence-specific and structure-specific modes of DNA recognition. The footprinting data suggest that the structure-specific [hUBF-G^G decoy] and sequence-specific [hUBF-UCE] complexes share structural features. In each case, a protected region symmetrically flanks a nuclease sensitive site. DNA bending is the likely common feature of these complexes. Indeed, a hallmark of the HMG domain is its propensity to interact with bent DNA and also to induce bending in linear sequences. SRY, to give one example, efficiently recognizes four way DNA junctions with sharp angles (Ferrari et al. (1992), 11 *EMBO J.* 4497–4506). Furthermore, SRY induces a sharp bend (85°) in a specific DNA sequence upon binding (Giese et al. (1992), 69 *Cell* 185–195). The specific interactions of the HMG domain with bent DNAs may be attributed to its "L" shaped cleft, as reported recently (Weir et al. (1993), 12 *EMBO J.* 1311–1319). hUBF probably also bends DNA, although detailed structural studies have yet to be performed. The DNase I hypersensitive site induced in the UCE upon hUBF binding may indicate DNA bending because DNase I activity is sensitive to structural features of DNA, including the width of the minor groove (Drew and Travers (1984), 37 *Cell* 491–502). The putative bend site is centered within a UCE region that is protected from DNase I; interestingly, the G^G-induced DNA bend is also centered within a DNase I-resistant region. Thus, it appears that the bent and unwound DNA structure induced by G^G mimics a favorable DNA conformation that occurs during the formation of a stable [hUBF-rDNA promoter] complex. A similar model was proposed recently to explain structure-specific recognition by SRY (King and Weiss (1993), 90 *Proc. Natl. Acad. Sci. U.S.A.* 11990–11994).

Results of in vitro competition assays (shown in FIG. 5) further established that the cisplatin decoy interacts with hUBF by substituting for the transcription factor's endogenous genomic binding site (the UCE) in the rDNA promoter. By logical implication, introduction of cisplatin decoys into the cellular milieu is expected to hijack hUBF and induce disarray of cellular processes normally dependent on proper [hUBF-promoter] complexing. In particular, the formation of high affinity [hUBF-decoy] complexes should reduce the amount of hUBF available for promoter binding. The steep relationship between promoter occupancy and nuclear hUBF concentration (FIG. 4) indicates that even a small degree of sequestration of hUBF by cisplatin lesions can significantly impair expression of nucleolar genes encoding rRNAs. Thus, rRNA transcription, and therefore cellular protein synthesis, will be compromised. Furthermore, binding of a sterically large protein, such as hUBF, to cisplatin lesions impedes or inhibits DNA repair. Indeed, studies have shown that, although G^G adducts are excised from cellular DNA in human cells (Fichtinger-Schepman et al. (1987), 47 *Cancer Res.* 3000–3004), this repair process is inefficient (Szymkowski et al. (1992), 89 *Proc. Natl. Acad. Sci. U.S.A.* 10772–10776). Results presented herein showed that the 14 bp region symetrically flanking the G^G lesion in the cisplatin decoy was strongly protected from nuclease cleavage. From this, it is reasonable to predict that this region would also be shielded from components of the enzymatic DNA repair machinery. In further support of this prediction, the XPAC protein, which recognizes damaged DNA and is essential for human nucleotide excision repair, has a relatively low affinity for G^G cisplatin lesions ($K_{d(app)}$>600 nM)(Jones and Wood (1993), 32 *Biochemistry* 12096–12104). XPAC, therefore, should not displace hUBF, which binds much more avidly to cisplatin lesions. hUBF therefore acts as an effective shield protecting cisplatin genomic lesions from repair.

Both DNA repair and protein synthesis are likely to be more critical for proliferating cells, such as those of tumors, than for quiescent cells, such as those of normal differentiated tissue (Mauck and Green (1973), 70 *Proc. Natl. Acad. Sci. U.S.A.* 2819–2822; Fraval and Roberts (1979), 39 *Cancer Res.* 1793–1797). The numbers of intracellular hUBF molecules, and of cisplatin genomic lesions formed in a typical round of chemotherapy, have been calculated. Both are in the range of about $5 \times 10^4$/cell (Bell et al. (1988), 241 *Science* 1192–1197; Reed et al. (1993), 53 *Cancer Res.* 3694–3699). Biologically significant and synergistic assaults on the viability of selected cells should therefore follow from the cisplatin-hUBF interactions predicted by both the hijacking and shielding models for cisplatin genotoxicity.

Still other classes of proteins for which second agents 9 of the present invention can be designed comprise nucleic acid processing proteins, e.g., ribonucleic acid (RNA) processing proteins, including proteins involved in splicing RNA gene transcripts to produce messenger RNA (mRNA). In addition, second agents can be designed that bind to other cellular macromolecules, e.g., RNA transcripts or portions thereof of genes that are actively expressed in selected cells but not in nonselected cells.

Cell-Component Binding Compounds Useful as Second Agent 9

Turning now to the structural features of second agent 9, it has been disclosed above that the second agent can be a ligand or an analog or derivative thereof, that is bound by the above-discussed protein preferentially associated with selected cells. Such ligands include estrogens, progesterones, androgens, glucocorticoids and other soluble hormones, toxins, clinically useful analogs and metabolites thereof, both of intracellular and extracellular origin, whether presently known or novel. Heterobifuntional ligand-genotoxic agent compounds have been prepared and subjected to preliminary studies that support extension of the cisplatin-based lesion shielding concept according to the first model described above. In one such compound, the ligand biotin was linked, through the use of standard techniques, to a genotoxic first agent. The particular first agent selected was the photoactivatable drug trimethylpsoralen (TMP), but it should be understood that any of the first agents disclosed herein could have been used. Psoralen compounds intercalate into double-stranded DNA at d(TpA) dinucleotides and form mono- and diadducts therewith upon exposure to near-UV irradiation (Cimino et al. (1985), 54 *Ann. Rev. Biochem.* 1151–1193). Biotin binds with extraordinarily high affinity to the proteins avidin and strepatavidin ($K_{d(app)}$ $10^{-15}$M, Green (1975), 25 *Adv. Protein Chem.* 85–133) and thus is widely used in research and clinical assays, such as enzyme-linked immunosorbent assays (ELISA), that capitalize on specific protein interactions to detect or quantitate a protein of interest. In this study, the biotin-TMP compound was mixed with duplex DNA comprising an additional, defined genomic lesion (deoxyuridine, the deamination product of cytosine) located in the immediate vicinity (within three base pairs) of the TMP lesion site. As described more fully in the Examples, the biotin-TMP compound effectively bound concurrently to duplex DNA and streptavidin, although both binding affinities were lower in the heterobifunctional compound than in the unconjugated precursors of the first and second agents. Quantitative gel shift assays revealed a $K_d$ of ~1.5 nM between streptavidin and the immobilized biotin. This $K_d$ value differs significantly from that of free biotin for streptavidin or avidin (the $K_d$ for free biotin with streptavidin or avidin is about $10^{-6}$ nM). Assuming that the biotin domain in the TMP-biotin conjugate behaved similarly to free biotin, the significant increase of the $K_d$ value (in other words, the decrease in binding affinity between biotin and streptavidin) was probably caused by the covalent binding of TMP-biotin conjugates to DNA. This effect likely can be minimized by further optimizing the linkage technique and nature of the linker employed. Techniques such as those described herein can be applied or adapted through no more than routine experimentation to accomplish this goal. As described, an optimal distance between a second agent ligand and the DNA helix should allow tight binding between the ligand and the cell component and yet adequately shield the DNA region vicinal to the adduct site (i.e., the genomic lesion). Streptavidin, when bound to damaged DNA at genomic lesion sites, shielded adjacent deoxyuridine lesions from repair by the appropriate DNA repair enzyme, uracil gylcosylase. These results are presented below in the Examples. The size of the shielded region, at least 20 adjacent nucleosides, was comparable to that of the DNA patch typically released by DNA excision repair enzymes.

Other heterobifunctional ligand-genotoxic agent compounds, in this case estradiol-chorambucil conjugates, have been prepared. These programmed genotoxic compounds are shown herein to mediate adherence of intracellular estrogen receptors (ER) to genomic lesions inflicted by chorambucil and to produce selective cytotoxicity. Again, it should be understood that, through appropriate standard techniques, the estrogen ligand could have been linked to any of the genotoxic first agents disclosed herein. Guidance is presented herein for confirming that estrogen receptors also can be used to shield genomic lesions effectively from repair by the cellular enzymatic DNA repair machinery, or to enhance uptake of the genotoxic compound by estrogen receptor positive cells, thereby contributing to the demise of selected cells that express estrogen receptors. According to the principles of the present invention, heterobifunctional compounds programmed to recruit the estrogen receptor to become a shield for genomic lesions comprise genotoxic first agent, an optional linker, and a second agent that affixes the receptor protein to the site of a lesion in cellular DNA caused by the genotoxic agent. Preferably, the genotoxic first agent is itself bifunctional and thus offers the capability of forming intra- or interstrand crosslinks in cellular DNA. Linking groups of varying length and molecular composition allow the practitioner to optimize the present compounds for concurrent binding of estrogen receptors and DNA. For example, the molecular composition of the linker can be adjusted so as to enhance solubility of the compounds under physiological conditions, or to enhance cell membrane permeability thereof. The length of the linker similarly can be adjusted to accommodate accessibility of the ligand second agent to the hydrophobic ligand binding pocket of the estrogen receptor while the genotoxic first agent is bound to cellular DNA.

There is precedent indicating that estrogen ligands that are affixed to large carrier molecules or to a solid support such as agarose, can still attract and bind the estrogen receptor from solution. The estrogen precursor estradiol has been linked at either the 7α or 17α position to agarose, creating a means to isolate the estrogen receptor from cell extracts by affinity chromatography (Sica et al. (1973), 248 *J. Biol. Chem.* 6543–6558; Bucort et al. (1978), 253 *J. Biol. Chem.* 8221–8228; Redeuilh et al. (1980), 106 *Eur. J. Biochem.* 481–493). DNA and agarose both have polysaccharide character. Unlike agarose, however, DNA monomer units of deoxyribose are linked by charged phosphodiester groups and are also bonded to heterocyclic purines or pyrimidines containing both nitrogen and oxygen atoms. Hydrogen atoms bonded to nitrogens and oxygens form hydrogen bonds within the helical DNA molecule, and can also form such bonds with proteins and other diffusible molecules. Such associations could assist in the formation of a lesion-shielding complex between the cell component, the heterobifunctional compound and cellular DNA, by analogy to interactions between cellular DNA and nuclear proteins that determine DNA structure and regulate gene expression. It is also possible, however, that hydrogen bonding could adversely affect the ability of the estrogen ligand to bind its receptor. Optimization of a linker disposed between the estrogen ligand and the genotoxic agent should, however, project the ligand sufficiently away from the DNA molecule, facilitating a high affinity interaction with the bound shielding protein.

Because appropriate precursors are readily available, the preparation of 17α linked derivatives of estradiol are the simplest from a synthetic chemical viewpoint. For example, starting with estrone (3-hydroxy-1,3,5[10]-estriene-17-one), substitution of a short amino alcohol at the 17α position of estradiol can be achieved using the Grignard reaction. Alternatively, 17α-ethynylestradiol can be used as a starting point for attachment of a short alkyl amine. The reported synthetic routes to 7α estradiol derivatives are more complex, but should still be within the abilities of those skilled in the art. Charpentier et al. (1988), 52 *Steroids* 609–621, synthesized 7α-carboxymethyl-9(11)-ene derivatives of estrone and estradiol starting with adrenosterone, in which a carboxymethyl group was first introduced at the 7α position and then the A ring was aromatized. In another published synthesis of 7α derivatives, Bucort et al. (1978), 253 *J. Biol. Chem.* 8221–8228 described the conjugate addition of a Grignard reagent to a canrenoate methylester, to ultimately produce a 7α carboxylic acid derivative of estradiol.

From the examples presented below, one of skill can readily adapt the methods used to demonstrate function of the streptavidin-attracting heterobifunctional compound suitably for demonstrating the biochemical and in vitro functionality of heterobifunctional compounds that comprise a ligand decoy for the estrogen receptor. Additional guidance is provided in the prospective examples further set forth below, particularly for assessing the ability of the ligand decoy to form interstrand crosslinks in DNA; assessing whether an appropriate lesion shielding complex is formed between damaged DNA and the estrogen receptor; and assessing the present ligand-decoy compound for selective killing in vitro of cells that express the estrogen receptor. Similar techniques can be applied or adapted with no more than routine experimentation to demonstrate functional properties of heterobifunctional compounds programmed to attract other ligand-responsive transcription factors. For example, the foregoing techniques can be adapted routinely to demonstrate function of heterobifunctional compounds that bind other steroid receptor proteins, such as androgen receptors, glucocorticoid receptors, progesterone receptors, and the like. Indeed, such studies are appropriate for evaluating the functionality of other heterobifunctional compounds, such as compounds designed to attract oncogene products, tumor suppressor gene products, cyclins, and the like and affix these cell components to the sites of genomic lesions. Electrophoretic mobility shift and DNase I protection analysis are suitable techniques generally for demonstrating whether a particular heterobifunctional compound forms genotoxic lesions, whether a chosen cell component is bound by a suitably programmed heterobifunctional compound, and whether the resulting complex is effective for shielding genomic lesions from the action of enzymes that act on cellular DNA.

Figure 9:
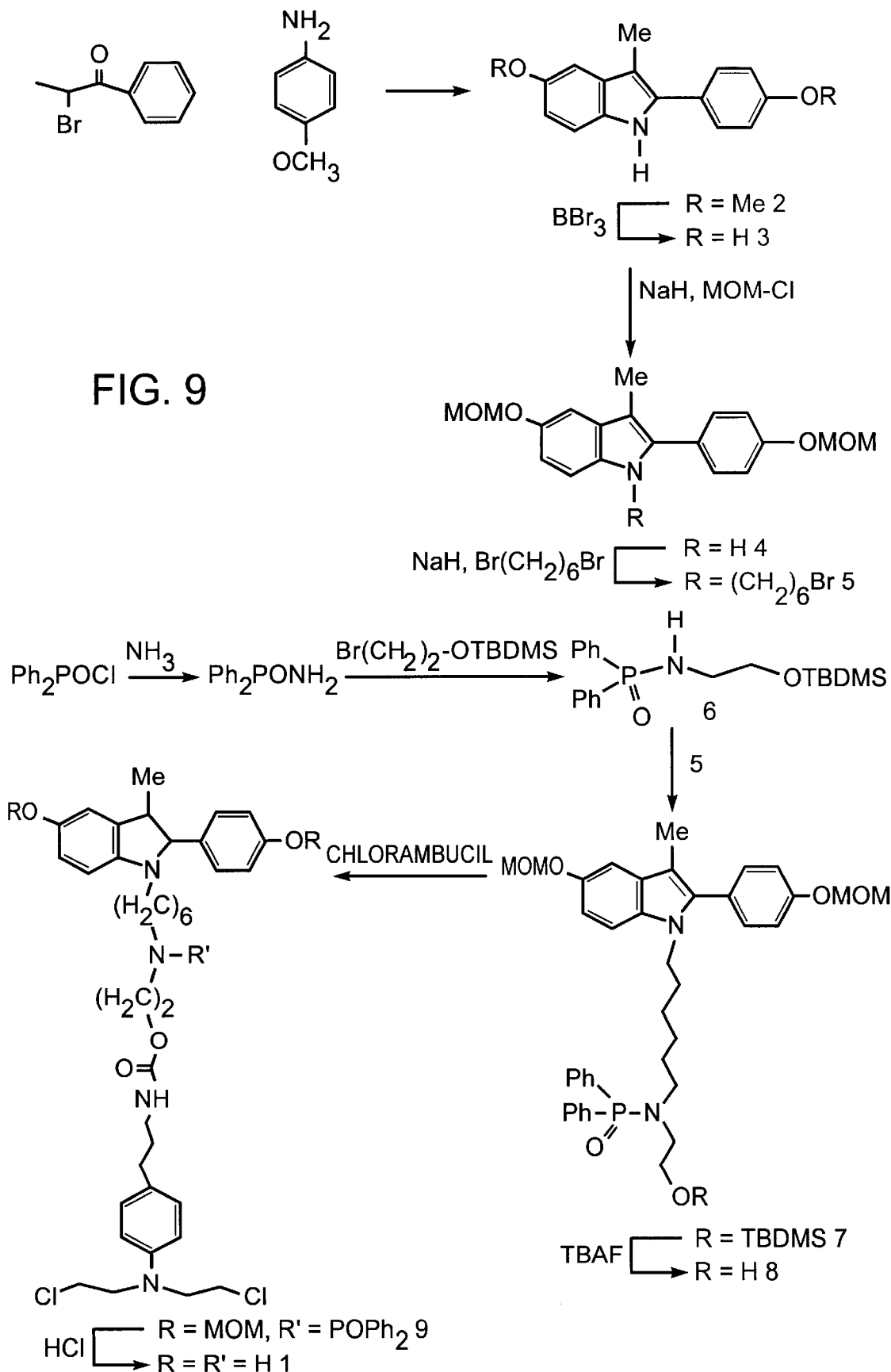
FIG. 9 presents a flow chart summarizing a chemical synthesis scheme for preparing a preferred heterobifunctional compound of the invention, demonstrated herein to be toxic selectively to cells that express estrogen receptor.

Still other heterobifunctional ligand-genotoxic agent compounds that specifically recognize estrogen receptor (ER) now have been prepared. A flowchart illustrating the preparation of a heterobifunctional 2-phenylindole-chlorambucil compound, 1-[6-(N-2-ethoxy-(O-(3-(4-(N,N-bis(2-chloroethyl)-aminophenyl)propylamine)carbamoyl)amine)hexyl]-5-O-hydroxy-2-(4-hydroxyphenyl)indole (1) is shown in FIG. 9 and discussed in Example 12. Heterobifunctional ER-ligand decoy compound 1 is presently a preferred embodiment of the invention, and has been demonstrated to bind to mammalian ER both when in solution and when affixed to double-stranded DNA (Example 13). Further, preferred compound 1 has been demonstrated to be cytotoxic selectively to mammalian cells that express ER (Example 14). This selective toxicity depends upon the chlorambucil first agent portion of compound 1, and is not due to antiestrogenic activity (Example 15). Thus, ER-ligand decoy compounds of the present invention do not kill ER-expressing cells selectively in the same manner as the therapeutic antiestrogen, tamoxifen. These results illustrate practice of the invention with a heterobifunctional compound programmed to affix a ligand-responsive transcription factor (ER) to genomic lesion sites.

As is apparent from the preliminary studies carried out with hUBF, second agent 9 can, in other embodiments, be a nucleic acid that mimics an endogenous genomic binding site of a transcription factor or other protein to be sequestered at genomic lesion sites. Nucleic acid second agents can be single stranded, double stranded, linear, branched, circular or a combination of these configurations. Either RNA or DNA can be used. Through intrastrand base pairing, linear or circular nucleic acid second agents can adopt stable hairpin or dumbell configurations (Chu and Orgel (1992), 20 Nucl. Acids Res. 5857–5858). Certain second agents (transcription factor decoys) can resemble either the sequence or the structure of the recognized transcription factor's endogenous binding site. That is, the nucleotide sequence of the decoy can comprise the sequence of the endogenous site, or a sequence sufficiently homologous thereto to confer protein-binding activity on the decoy. For example, the decoy sequence can be a conservative variant of the endogenous sequence, such as a sequence that binds, under stringent hybridization conditions, to the endogenous sequence. Preferably, the decoy sequence is more than 50% identical to the endogenous sequence. More preferably, it is more than 70% identical, and even more preferably, it is more than 90% identical. It is well known that the binding avidity of many nucleic acid binding proteins that recognize specific nucleotide sequences can be enhanced by nucleic acid regions adjacent to the actual binding site. These flanking regions can be disposed 3' or 5' to the specific, recognized sequence. As the nucleic acid binding protein need not interact directly or strongly with nucleotides in the flanking region, greater sequence variability can be tolerated at such locations than in the binding site itself. Thus, decoys can be constructed that comprise a core, conserved binding sequence flanked by adjacent regions that modulate, e.g., enhance, binding preference of the protein to the decoy relative to the endogenous site. Similar principles can be applied to the construction of nucleic acid decoys that mimic nucleic acid structures rather than sequences. Structural features recognized by the protein can be produced by folding, looping, kinking, adoption of higher ordered structures (e.g., cruciforms) or of nonclassical helix configurations (e.g., ZDNA) by the nucleic acid decoy. Optionally, these structural features can be stabilized by non-nucleic acid components of the decoy, such as crosslinking agents. Still further variation can be introduced, and favorable properties (e.g., stability under in vivo conditions) emphasized, by the use of nucleotide analogs or derivatives such as phosphorothioate analogs, or $O^6$- and/or $O^4$-methylguanine derivatives, in the decoy sequence.

An important class of nucleic acid second agents 9 includes those known in the art as "aptamers". Aptamers are the products of directed, also known as in vitro, molecular evolution. The term "aptamer" was originally coined by Ellington and Szostak to describe the RNA products of directed molecular evolution, a process in which a nucleic acid molecule that binds with high affinity to a desired ligand is isolated from large library of random DNA sequences (Ellington and Szostak (1990), 346 Nature 818–822). The process involves performing several tandem iterations of affinity separation, e.g., using a solid support to which the desired ligand is bound, followed by polymerase chain reaction (PCR) to amplify ligand-eluted nucleic acids. Each round of affinity separation thus enriches the nucleic acid population for molecules that successfully bind the desired ligand. In this manner, Ellington and Szostak "educated" an initially random pool of RNAs to yield aptamers that specifically bound organic dye molecules such as Cibacron Blue (Id at FIG. 2). Certain of the aptamers obtained could discriminate between Cibacron Blue and other dyes of similar structure, demonstrating specificity of the technique. Aptamers can even be engineered to distinguish between stereoisomers that differ only by optical rotation at a single chiral center (Famulok and Szostak (1992), 114 J. Am. Chem. Soc. 3990–3991). Originally, it was thought that RNA aptamers would be more suitable for ligand recognition, in view of established knowledge of naturally occurring RNAs with higher ordered three-dimensional structures (e.g., rRNA or transfer RNA, tRNA). However, single-stranded DNA molecules produced by asymmetric PCR amplification were also shown to be effective (Ellington and Szostak (1992), 355 Nature 850–852). It should be noted that aptamers can be prepared from nucleotide analogs, such as phosphorothioate nucleotides, which can offer increased aptamer stability under physiological conditions. Standard techniques are available for linking nucleic acids, such as transcription factor decoys and aptamers, to other chemical moieties, such as genotoxic drugs, without substantial loss of protein-recognition capability and genotoxicity.

The principles of directed molecular evolution encompass the production of aptamers that bind with high affinity to proteins, such as DNA binding proteins, including transcription factors (Tuerk and Gold (1990), 249 Science 505–510; Famulok and Szostak (1992), 31 Angew. Chem. Intl. Ed. Engl. 979–988, the teachings of which are herein incorporated by reference). Recently, an aptamer has been reported that binds with high affinity to the extracellular protein thrombin (Bock et al. (1992), 355 Nature 564–566), and can impair thrombin catalyzed blood clot formation. High affinity aptamers can be generated even against proteins for which there is little or no structural or ligand-recognition information available (Famulok and Szostak (1992), 31 Angew. Chem. Intl. Ed. Engl. 979–988; see discussion concerning the HIV Rev protein). Thus, aptamer second agents can be generated, through available techniques, that bind to virtually any desired selected-cell associated protein, whether or not the protein has a known natural ligand or endogenous genomic binding site. This flexibility offers great promise in the design of programmable genotoxic drugs useful in selectively destroying neoplastic or virally infected cells, such as cells infected with the human immunodeficiency virus (HIV) or tumorigenic adenoma and papilloma viruses. The aptamer-recognized protein can be a member of any of the general classes discussed herein: transcription factors, ligand-responsive transcription factors, oncogene products, tumor suppressor gene products, cell cycle regulatory proteins, nucleic acid processing proteins, nuclear structural proteins, and the like. A preferred aptamer binds to the nuclear phosphoprotein p53. A particularly preferred aptamer binds to a region of tumor-associated mutant p53 that is cryptic in wildtype p53, such as the PAb240 epitope (Gannon et al. (1990) 9 EMBO J. 1595–1602; Steven and Lane (1992), 255 J. Mol. Biol. 577–583). As described more fully in the examples, a population of aptamers that bind selectively to the PAb240 epitope has been prepared. Heterobifunctional compounds comprising an aptamer amplified from this pool and thus programmed to bind mutant p53 can be assessed for biomolecular and in vitro function through appropriate routine adaptation of the techniques and guidelines set forth below in the actual and prospective examples.

Yet another general class of second agents 9 includes peptide ligands selected from so-called epitope libraries. Libraries of random peptides of defmed average length are available, as are techniques for preparing additional such libraries. Such libraries have been used for determining the precise epitope recognized by an antibody of interest (Geysen et al. (1984), 81 Proc. Natl. Acad. Sci. USA 3998–4002; Fodor et al. (1991), 251 *Science* 767–773, the teachings of each of which are incorporated herein by reference). At least one "living library" has been constructed, from filamentous bacteriophage expressing random peptide epitopes cloned into a viral coat protein (Scott and Smith (1990), 249 *Science* 386–390, the teachings of which are incorporated herein by reference). This technology offers the advantages that phage displaying a peptide with favorable binding characteristics can be affinity purified against a desired protein component of selected cells (e.g., a transcription factor, cyclin, intracellular receptor, or tumor suppressor gene product), propagated in vivo using a bacterial host, and subjected to techniques such as site-directed mutagenesis to improve further the binding affinity for the desired protein. Through appropriate genetic engineering techniques, a peptide optimized for binding in this manner can be introduced into a high-expression host cell (e.g., a bacterial host such as *E. coli*), optionally produced as a cleavable fusion protein, and isolated in high yield. In this manner, large amounts of a peptide second agent can be prepared and linked, through standard techniques, to a genotoxic first agent to produce the heterobifunctional compound disclosed herein. Appropriate techniques for linking peptide second agents to genotoxic first agents without incurring substantial loss of protein-recognition capability or genotoxicity are known and available.

Still another general class of second agents 9 include organic and inorganic compounds isolated from libraries of synthetic organic and inorganic compounds prepared by combinatorial synthesis (Needels et al. (1993), 90 *P.N.A.S. USA* 10700–10704; Ohlmeyer et al. (1993), 90 *P.N.A.S. USA* 10922–10926). Combinatorial chemistry involves the simultaneous production of large sets of related molecules which are then screened for a desired trait. Early in its development, combinatorial chemistry was used to generate libraries of variants of benzodiazepines which can target a wide variety of receptors and enzymes, as described in Ellman et al., U.S. Pat. No. 5,288,514, the disclosure of which is incorporated by reference herein. More recent developments include the generation and screening of a library of about 500 mercaptoacyl prolines to identify a new treatment for hypertension and heart disease. Gallop, et al. (1995), 114 *J. Am. Chem. Soc.* 7029 (1995). For the purposes of this invention, a combinatorial library would be created and then assayed for its binding affinity to a protein preferentially associated with selected cells. The techniques of combinatorial chemistry are well known in the art, and kits for performing combinatorial chemistry are commercially available. For example, Novabiochem publishes a catalog of components for generating combinatorial chemistry libraries. (Novabiochem, *The Combinatorial Chemistry Catalog including Solid Phase Organic Chemistry Handbook*, March 1998). Another vendor of reagents for combinatorial chemistry technology is Irori of La Jolla, Calif.

Linkage Between First and Second Agents

In the heterobifunctional compounds disclosed herein, the above-described first and second agents are linked together, preferably covalently. In many embodiments, the first and second agents are linked through covalent linker 7. In other embodiments, linkage of the first and second agents is accomplished by noncovalent association. In such embodiments, the first and second agents optionally become linked to form compound 3 intracellularly. Linkage thus can occur after either the first agent has bound to cellular DNA, or the second agent has become complexed with the cell component. One example of a noncovalent linker comprises complimentary oligonucleotide strands (e.g., oligo(dG)/oligo(dC)) covalently attached, respectively, to the first and second agents.

In most embodiments, however, the first and second agents are linked directly by a covalent bond or indirectly through covalent bonds to an organic linker. This organic linker comprises a linear, branched or cyclic, aliphatic, aromatic or mixed aliphatic and aromatic organic compound comprising preferably up to about 20 carbon atoms, optionally in association with other atoms, such as oxygen, nitrogen or sulfur, that occur naturally in biological molecules. The organic linker can be, for example, a peptide, oligosaccharide, oligonucleotide, carbamate or urea derivative, such as an oligocarbamate peptide analog. Additional examples of linkers include polymers assembled from linkable monomers independently selected from ethyleneglycols, alkyldiamines and the like such as polyethylene glycol, ureas, or spermine/spermidine. The linker serves to space apart the binding moieties of the first and second agents such that the heterobifunctional compound disclosed herein can sterically accommodate concurrent binding to cellular DNA and the cell component. Yet, the linker does not separate the first and second agents so far as to obviate shielding of the genomic lesion by the cell component that is bound to the second agent. In certain embodiments, the organic linker comprises up to about 12 carbon atoms. In other embodiments, it comprises up to about 8 carbon atoms. Yet in still other embodiments, such as where the second agent must access a deep cleft or pocket in a recognized cell component protein, the linker can comprise up to about 30 carbon atoms. Whether covalent linkage of the first and second agents is direct or indirect (through the optional linker), the linkage is stable under physiological conditions, particularly intracellular conditions. That is, the linkage is resistant to cleavage by hydrolysis or other biochemical processes, including enzymatic processes. For this reason, linkers comprising amide or ester bonds are not presently preferred. Conversely, linkers comprising carbamate or urea moieties are preferred herein due to their stability and hydrophilicity characteristics. For example, oligocarbamate peptide analogs comprised of aminocarbamate monomers linked through a carbamate backbone have been reported to be stable for at least 150 minutes in the presence of trypsin or pepsin (Cho et al. (1993), 261 *Science* 1303–1305).

Linkage of the first agent to the second agent, either directly or through the optional organic linker, can be accomplished by applying routine chemical or biochemical techniques, or modifications thereof that will be readily apparent to those of skill in the art. The particular linkage reactions carried out will be determined by the types of first and second agents to be joined to produce a desired heterobifunctional compound. It will be recognized by those of skill in the art that the optional linker provides an opportunity to improve the hydrophilicity or cell membrane permeability qualities of the present compounds, by including moieties that confer these properties within the organic linker.

Uses for Heterobifunctional Programmable Genotoxic Compounds

The heterobifunctional programmable genotoxic compounds disclosed herein are useful in a method for destroying selected cells in a heterogeneous cell population. Broadly, the method comprises the steps of contacting the heterogenous cell population with a heterobifunctional compound as disclosed above, and incubating (maintaining contact of) the cell population with the compound for a period of time sufficient for the compound to internalize within cells, bind to cellular DNA and bind to a cell component preferentially associated with selected cells so as to produce a steric shield that protects genomic lesions from repair. As mentioned previously, the heterogenous cell population can comprise cells of a unicellular or multicellular organism, and can comprise cells maintained in culture, cells withdrawn from a multicellular organism, or cells present in the tissues or organs of a multicellular organism. That is, the method can be practiced in vitro, ex vivo (using a sample, such as a biopsy, withdrawn from a multicellular organism such as a mammal, e.g., a human), or in vivo, by local or systemic administration to a multicellular organism. The recognized cell component can be one naturally associated with the cell, or one intentionally introduced into the cell, e.g., by genetic engineering techniques. The present method therefore offers the prospect of broadening the range of biological selection methods available, e.g., for the production of recombinant proteins or for the isolation of cells with improved or desirable characteristics.

Extensive discussion has been devoted herein to programmable genotoxic compounds that are appropriate for co-opting cell components that phenotypically distinguish, for example, dividing cells such as transformed (malignant or neoplastic) cells from normal cells, virally infected cells from uninfected cells, and cells of a pathogenic organism from cells of a host organism. It should be understood that the method disclosed herein can be practiced to achieve the selective killing of cells that are phenotypically distinguishable from other cells of a heterogenous cell population on any of these grounds. In particular, it should be understood that the method can be used to achieve selective killing of neoplastic (transformed) cells of colorectal, reproductive tract, hepatic, lymphoid, mammary, myeloid, neurologic or respiratory tract origin. Cells that are of reproductive tract origin can be more specifically, of ovarian, uterine, endometrial, cervical, vaginal, prostate, or testicular origin. Cells that are of mammary origin can be more specifically, of breast origin. As is apparent from the disclosure herein, selective killing of such cells can be accomplished through the use of second agents that recognize intracellular proteins associated with malignant transformation. Thus, for example, heterobifunctional compounds can be programmed or designed to selectively destroy malignant cells that express an oncogene product (e.g., erbB, abl or myc) a mutant tumor suppressor gene product (e.g., mutant p53) or an aberrant cyclin or cyclin-dependent kinase. Appropriate heterobifunctional compounds could comprise a genotoxic agent linked to a ligand, an aptamer, a binding polypeptide or a small organic molecule, e.g., produced by combinatorial synthesis, that binds the target macromolecule. Alternatively, compounds can be programmed to selectively destroy cells whose survival or proliferation are dependent on the expression of certain genes by incorporating a second agent that is a transcription factor decoy. Malignant cells whose proliferation is driven by an aberrantly expressed ligand-responsive transcription factor, such as an estrogen receptor, androgen receptor or progesterone receptor, can be selectively destroyed by compounds incorporating ligand mimics as second agents. Such ligand mimics include androgens, estrogens, progesterones, glucocorticoids and receptor binding analogs and derivatives thereof (e.g., the clinically relevant estrogen analog, tamoxifen). For example, estrogen or estrogen analog-containing heterobifunctional compounds can be used to achieve selective killing of breast or ovarian cancer cells, progesterone compounds can be used similarly to kill uterine or endometrial cancer cells, and androgen compounds can be used to kill prostate cancer cells.

Presently preferred estrogen analog-containing compounds include 2-phenylindole compounds and analogs thereof, including 1-[6-(N-2-ethoxy-(O-(3-(4-(N,N-bis(2-chloroethyl)aminophenyl)propylarnine)carbamoyl)amine)hexyl]-5-O-hydroxy-2-(4-hydroxyphenyl)indole (1). Such compounds are anticipated herein to destroy selectively malignant estrogen receptor positive cells of breast or reproductive tract origin, especially cells of ovarian origin. Similarly, it is anticipated that androgen and androgen analog-containing compounds prepared by application of the principles of the present invention will destroy selectively malignant, androgen receptor positive cells of reproductive tract origin, especially cells of prostate origin.

Heterobifunctional compounds of the present invention also can be designed to destroy selectively cells of an infectious organism, either in vitro or in vivo, that are present in a heterogenous cell population comprising cells of a host or infected organism, and cells of an infectious organism such as a bacterium, a fungus, a virus or a parasite. Thus, compounds disclosed herein are expected to be particularly useful in maintaining the health and integrity of cultured cells (e.g., mammalian cells) in vitro, as well as in the treatment of infectious diseases in vivo caused by pathogenic organisms including those with acquired resistance to currently available antibiotic, antifungal or antiparasitic drugs. Infectious diseases for which the availability of programmable genotoxic compounds are urgently needed accordingly include, but are not limited to, septic wound infections, hospital-acquired infections, tuberculosis, malaria and amoebic dysentery. Other examples, particularly of parasitic diseases, for which programmable genotoxic compounds offer the potential to expand the range of available genotoxic agents, include schistosomiasis, filiariasis, Chagas disease, leishmaniasis, sleeping sickness, toxoplasmosis, pneumocystosis, giardiasis, trichomoniasis, croptosporidiosis, and the like. *Harrison's Principles of Internal Medicine,* Part 5 Infectious Diseases, Ch. 156–172. Certain of these diseases are relatively common among cosmopolitan communities, while others present severe threats to the populace of developing nations.

Alternatively, the present compounds can be used in vitro to enrich a heterogenous cell population for cells having a desirable characteristic, or cells lacking an undesired characteristic. Thus, the present compounds offer new alternatives to current methods for, e.g., isolating a hybridoma cell producing a desired antibody from a heterogenous cell population comprising primary antibody producing cells and an immortalized fusion partner cell line. Alternatively, the present compounds expand the range of genetic selection agents useful for separating a desired cell transfected with heterologous nucleic acids from a cell population comprising unsuccessful transfectants.

Those of skill in the art will readily understand and appreciate that the incubation period needed to achieve selective cell killing will vary widely, depending on the circumstances under which the invention is practiced. In many instances, the time period needed to achieve selective killing of cultured cells or suspensions of unicellular organisms or of cells withdrawn from a multicellular organism will be less than the time needed to achieve selective killing of cells in vivo in a multicellular organism. For in vivo use to destroy selected cells in the tissues of a multicellular organism (e.g., a mammal) the protocols in which the drugs are used will vary depending on the location of cells to be destroyed, replicative rate of the cells, level of repair proficiency of the cells, dose of heterobifunctional compound administered, route of administration (generally either systemic or local, and either enteral or parenteral), and pharmacokinetic profiles of clearance and tissue uptake of the compound. Variables affecting the dose thus include, but are not limited to, the nature (e.g., species or tissue type), quantity and accessibility (i.e., body compartment location) of selected cells to be destroyed, and the nature, genotoxicity, and affinity of the compound for the recognized cell component. The present compound can be combined with a pharmaceutically acceptable carrier or excipient for formulation as a liquid, suspension, solid, salve, ointment or the like, suitable for oral, nasal, intravenous, intraperitoneal, topical, subdermal, intramuscular, or other routes of administration. The present compound can be administered in a single dose (e.g., a bolus injection), a series of doses of equivalent, escalating, decreasing or intermittently varied quantity, or infused over a period of time (e.g., by intravenous drip or infusion), or by release from a slow-release delivery vehicle. The appropriate dose of the present compound will of course be dictated by the precise circumstances under which the invention is practiced, but will generally be in the range of 0.01 ng to 10 g per kg body weight, preferably in the range of 1 ng to 0.1 g per kg, and more preferably in the range of 100 ng to 10 mg per kg.

If desired, the degree of selective cell killing achieved can be ascertained through standard, widely available techniques, such as visual or microscopic inspection, biochemical, chromogenic or immunologic methods for detecting products of selected cell lysis, and the like. Such techniques can be used to establish both the dose and time period effective to accomplish objectives of the present invention under particular circumstances. Once effective doses and time periods are established, it may be no longer necessary to monitor the progress of selective cell killing.

Practice of the invention will be still more fully understood from the following examples, which are presented herein for illustration only and should not be construed as limiting the invention in any way.

EXAMPLE 1

Western and Southwestern Blotting Studies with hUBF

Probe Preparation. The DNA probe used for southwestern blotting was a 422 base pair (bp) AvaI restriction fragment excised from M13mp19 replicative form DNA. Platinated probes were prepared by treating the AvaI-digested DNA with cisplatin or trans-DDP, and the formal bound drug/nucleotide ratios ($r_b$) were determined by using atomic absorption spectroscopy as described in Donahue et al. (1990), 29 Biochemistry 5872–5880.

Western and Southwestern Blotting Technique. HeLa whole cell extracts (WCE) were prepared by the sonication procedure of Samson et al. (1986), 83 Proc. Natl. Acad. Sci. U.S.A. 5607–5610. The 97 kDa hUBF species was synthesized by in vitro transcription and translation from the plasmid pTbGUBF1 as reported in Jantzen et al. (1992), 6 Genes & Dev. 1950–1963. In vitro translated hUBF was quantitated by the incorporation of $^{35}$S-methionine. Protein samples (75 mg WCE or 8 ng hUBF) were resolved on 5–15% gradient SDS polyacrylamide gels and transferred to nitrocellulose membranes. Parallel blots of HeLa whole cell extracts (WCE) and in vitro translated hUBF (hUBF) were probed with various $^{32}$P labeled DNA fragments (southwestern analysis, panels A–C of FIG. 2) or antiserum against hUBF (Anti-NOR-90) (panel D of FIG. 2). For southwestern analysis, the air dried membranes were processed as reported in Toney et al. (1989), 86 Proc. Natl. Acad. Sci. U.S.A. 8328–8332. In the probing step, the labeled DNA was present at about $5 \times 10^4$ cpm/ml and the nonspecific competitor poly(dI-dC).poly(dI-dC) at 5 mg/ml. The blot shown in Panel A was probed with the cisplatin (cis-Pt-422) modified probe, that shown in Panel C with the trans-diamminedichloroplatinum(II) (trans-Pt-422) modified probe, and that shown in Panel B with unmodified (Un-422) probe. HeLa proteins recognizing cis-Pt-422 are listed by molecular weight to the left of Panel A. The rb values for probes modified by cisplatin and trans-DDP were 0.043 and 0.052, respectively. During autoradiography, a 0.254 mm thick copper sheet was used to block $^{35}$S emissions selectively from the in vitro translated hUBF. For western analysis (Panel D), the filter was probed with a 1/250 dilution of antiserum to human NOR-90 (hUBF) obtained as a gift from E. K. L. Chan (Chan et al. (1991), 174 J. Exp. Med. 1239–1244). Antibody binding was visualized through standard techniques, using a chemiluminescent detection system commercially available from BioRad. The positions of both HeLa and in vitro translated hUBF are shown. A 120 kDa species of unknown identity was also visualized in the WCE with Anti-NOR-90.

Figures 2A, 2B, 2C, 2D:
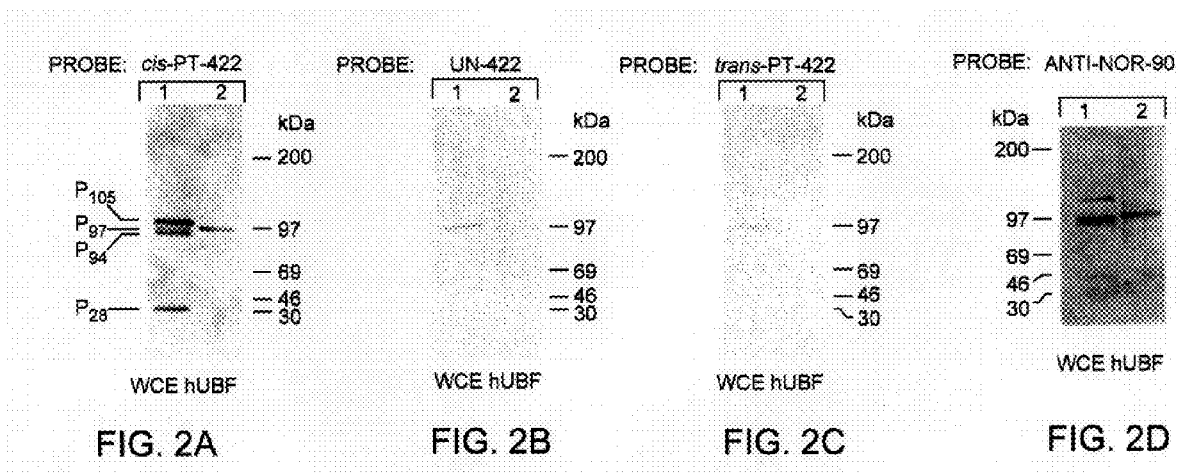
FIG. 2, Panels A–D, presents autoradiograph results of Southwestern (A, B and C) and Western Blot (D) studies of the binding of an HMG-box transcription factor, hUBF (human UBF), to a structural decoy comprising a cisplatin 1,2-dinucleotide intrastrand DNA adduct. (WCE=whole cell extract; hUBF obtained from in vitro translation; Anti-NOR-90=antiserum against hUBF.)

Results. Protein blots of human HeLa cell extracts (FIG. 2A) probed with cisplatin modified DNA (southwestern analysis) revealed species of $M_{r(app)}$ 97, 94 and 28 kDa. Unmodified DNA or DNA modified with the clinically ineffective trans-DDP compound was not bound by these proteins (Panels B and C), although a 105 kDa nonspecific DNA binding protein was detected with each of the three DNA probes. The 28 kDa species has recently been identified as the abundant chromatin protein HMG1 (Pil and Lippard (1992), 256 Science 234–237; Hughes et al. (1992), J. Biol. Chem. 13520–13527). The precise functions of HMG1 remain unclear although it has been proposed to play roles in the maintenance of chromosome structure and the alteration of DNA topology, and may therefore be important for transcription and DNA replication (Bustin et al. (1990), 1049 Biochem. Biophys. Acta 231–243). Since the HMG box is a unifying feature of many cisplatin lesion recognition proteins, it was postulated that the 97 and 94 kDa proteins possess this DNA binding domain. The RNA polymerase I transcription factor hUBF contains several regions of homology to HMG1 (Jantzen et al. (1990), 344 Nature 830–836) and exists as both 97 and 94 KDa species owing to an alternative splicing event (Chan et al. (1991), 174 J. Exp. Med. 1239–1244). Western blot analysis with hUBF antiserum demonstrated that the hUBF doublet resembles the bands detected by southwestern analysis (compare FIG. 2, Panels A and D). From these observations, it was postulated that hUBF binds to cisplatin DNA lesions. This postulate was confirmed by southwestern blot analysis of in vitro translated hUBF (FIG. 2A, lane 2).

EXAMPLE 2

DNase I Footprinting Studies of the [hUBF-Cisplatin] Complex

Probe Preparation. A 100 bp DNA fragment containing a single, centrally located 1,2 intrastrand cis-$[Pt(NH3)2]^{2+}$ d(GpG) crosslink (G^G-100) and the analogous unmodified fragment (Un-100) were used as both competitor DNAs and probes in hUBF footprinting experiments. These DNA fragments were kindly provided by P. Pil and S. J. Lippard (Pil and Lippard (1992), 256 Science 234–237). The adduct-containing strand of G^G-100 and the analogous unmodified strand of Un-100 were 5' end-labeled with $\gamma$ $^{32}$P-ATP (>6,000 Ci/mmole), using polynucleotide kinase according to standard procedures. The 5' end of the unadducted strand was removed with AvaI to generate the 90 bp footprinting probes. These were purified by passage through Sephadex G-25 Quickspin™ columns (Boehringer Mannheim).

DNase I Footprinting Technique. Homogeneous HeLa hUBF was used to generate DNase I footprints on both rRNA promoter (described below) and platinated DNA probes. Footprinting was performed essentially as described in Bell et al. (1988), 241 *Science* 1192–1197. hUBF was added to footprinting reactions containing the appropriate labeled DNA probe $10^3$–$10^4$ cpm, 0.7–50 pM, depending on the experiment) and binding buffer (25 mM Tris-HCl pH (7.9), 14 mM MgCl$_2$, 0.5 mM dithiothreitol, 10% glycerol, 50 mM KCl, 0.05% Nonidet-P40, 2.5 mM CaCl$_2$) in a total volume of 50 ml. The binding reactions were incubated for 10 min. at 30° C. and then digested with DNase I (Worthington DPFF grade) for 1 min. at 25° C. The DNase I reactions were terminated by adding a solution of 20 mM EDTA, 1% SDS, 0.2 M NaCl, and 50 mg/ml yeast total RNA. Samples were phenol/chloroform extracted, ethanol precipitated, and electrophoresed according to standard procedures on denaturing wedged (0.4–1.5 mm) sequencing gels (6% or 12% for promoter footprints or G^G-100 footprints, respectively) at 70W. Gels were fixed, dried and exposed with an intensifying screen to preflashed X-ray film at 80° C., and analyzed by using a Molecular Dynamics PhosphorImager™ imaging machine.

Figure 3A:
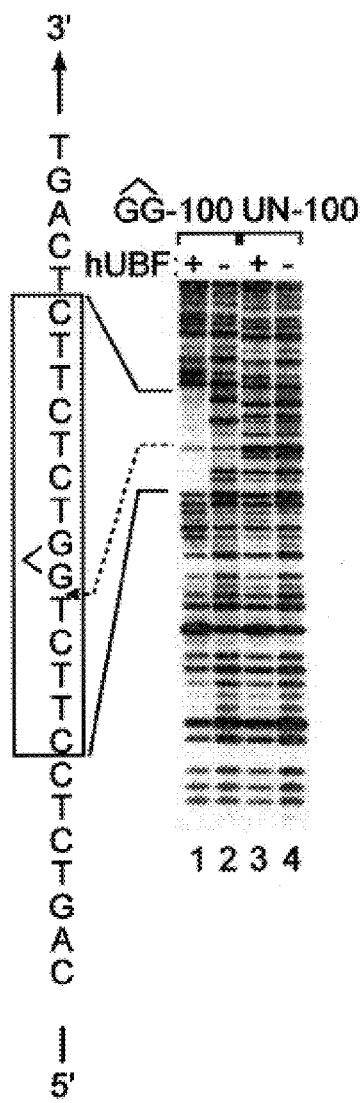
FIG. 3, Panels A and B, presents autoradiograph results of DNase I footprinting studies showing that hUBF protects a region of the decoy symmetrically spanning the cisplatin adduct site (SEQ ID NO:5).
Figure 3B:
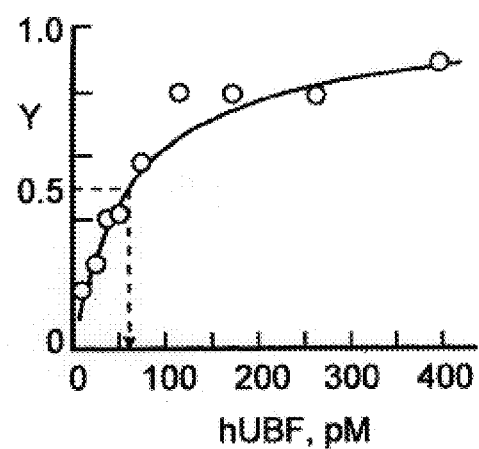

Results. As shown in FIG. 3, Panel A, 400 pm hUBF was sufficient to protect the area of the probe immediately adjacent to the defined G^G adduct from DNase I cleavage (compare lanes 1 & 2). A distinct protection pattern was observed in the 14 bp region encompassing the adduct, providing direct evidence that hUBF recognizes the structural distortion induced by G^G. The relevant sequence is shown to the left, and the protected residues are displayed within the box. The broken line indicates a residue immediately 5' to G^G that remained DNase I-sensitive. The established structural features of the G^G adduct include helix bending (34°) toward the major groove (Bellon and Lippard (1990), 35 *Biophys. Chem.* 179–188) and unwinding (−13°) (Bellon et al. (1991), 30 *Biochemistry* 8026–8035). No such protection is afforded the analogous unmodified 100-mer (lane 3), which gave the same cleavage pattern both in the presence and in the absence of hUBF (lanes 3 & 4). Cleavage patterns of G^G-100 and Un-100 near the cisplatin adduct should be directly comparable (lanes 2 & 4). Panel B shows the PhorphorImager semi-quantitative profile of hUBF binding to G^G-100. Y is the fractional saturation of G^G-100 and was estimated by monitoring the intensity of three bands in the protected region at each hUBF concentration. The data fit the equation $K_d$=[hUBF][G^G-100]/[hUBF-G^G-100] when $K_d$=60 pM. The protein concentration giving half-maximal binding ($K_{d\ (app)}$ is indicated by the broken line. The labeled probe was present at 20 pM ($10^4$ cpm). These results indicate that [hUBF-cisplatin] complex formation is exceptionally favorable, in energetic terms. From the shape of the semi-quantitative binding profile, it is also apparent that binding is non-cooperative.

EXAMPLE 3

DNase I Footprint Studies of the [hUBF-DNA Promoter] Complex

Probe Preparation. For footprinting studies, the EcoRI-BstEII restriction fragment of pSBr208 containing the −208 to +78 region of the human rRNA gene was either 5' or 3' end-labeled on the noncoding strand. pSBr208 was digested with EcoRI and the 5' phosphate was removed with calf intestinal phosphatase. EcoRI-digested pSBr208 was 5' end-labeled with γ$^{32}$P-ATP (>6,000 Ci/mmole) and subsequently digested with BstEII. The 286 bp footprinting probes were purified on 5% polyacrylamide gels and electroeluted. In cases where higher specific activity footprinting probes were required, the noncoding strand was 3' end-labeled by using the Klenow enzyme in the presence of [α-$^{32}$P]-dATP, [(α-$^{32}$P]-dCTP, and [α-$^{32}$P]-dGTP (>6,000 Ci/mmole).

The DNase I footprinting technique described in the preceding example was followed in the present promoter-binding studies.

Figure 4A:
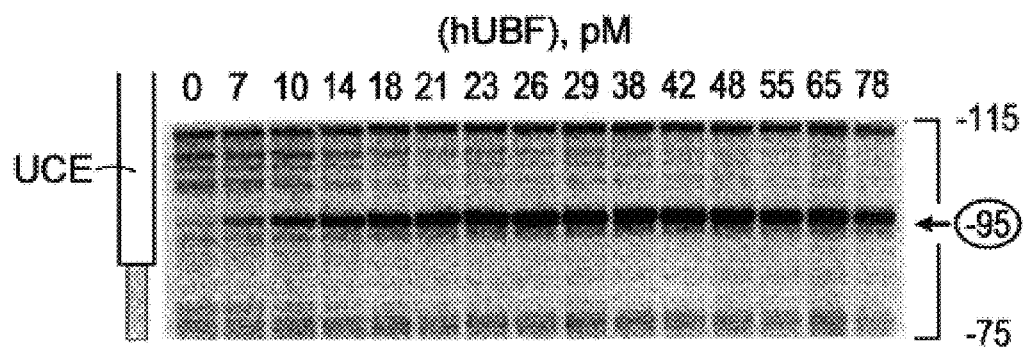
FIG. 4, top and bottom panels, presents autoradiograph results of studies establishing the affinity of hUBF for its endogenous genomic binding site.
Figure 4B:
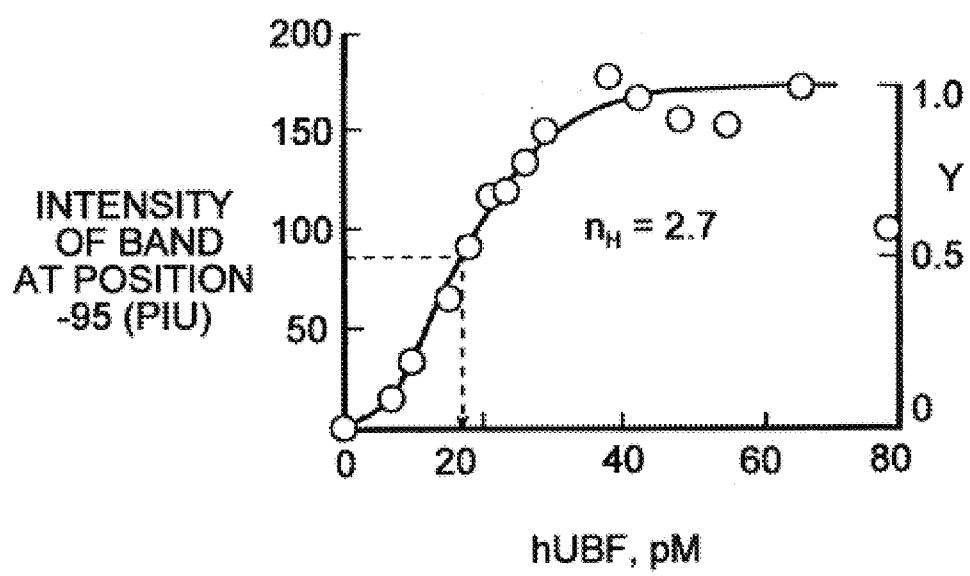

Results. The biological significance of cisplatin adduct recognition by hUBF ultimately depends on the affinity of the interaction. The interaction of hUBF with rDNA accordingly provides a useful benchmark value for a biologically relevant affinity. The upper panel of FIG. 4 shows the rDNA binding profile at hUBF concentrations ranging from 7–78 pM. The formation of [hUBF-promoter] complexes resulted in DNase I hypersensitivity at positions −20 and −95 in the CORE and UCE elements, respectively. In addition, the 40 bp region that symmetrically flanks −95 became refractory to cleavage (Bell et al. (1988), 241 *Science* 1192–1197). The degree of promoter occupancy was most easily visualized by the increased DNase I sensitivity of the −95 position in the upstream control element (UCE). The 3' labeled probe used to generate the results shown in FIG. 4 was present at 0.7 pM ($10^3$ cpm). Bands thus appear as doublets due to incomplete labeling.

hUBF binding was next quantitated by measuring the intensity of the enhanced cleavage at −95. In the bottom panel, intensity is reported to the left in arbitrary PhosphorImager units (PIU), and, to the right, is expressed as the apparent fractional saturation (Y). The protein concentration giving half-maximal binding ($K_{d(app)}$, 18 pM) is indicated by the broken line. Thus, hUBF binds tightly to its endogenous site(s) in the rDNA promoter. It should be noted that the affinities of hUBF for promoter sequences and for the cisplatin decoy are comparable, differing by only three-fold. This suggests that cisplatin adducts can be effective decoys for hUBF in the cellular milieu. It should further be noted that the UCE footprint qualitatively resembles that observed for G^G-100. In both complexes, a protected region symmetrically flanks a nuclease sensitive site. The shape of the hUBF-promoter binding profile reveals that the fraction of bound promoter (Y) increases sharply over a narrow range of hUBF concentrations, indicating that binding is cooperative. A Hill plot of these data yielded a best fit line (r=0.997) with a Hill constant ($n_H$) of 2.7, indicating positive cooperativity. Cooperativity has also been reported for Xenopus UBF binding to enhancer repeats (Putnam and Pikaard (1992), 12 *Mol. Cell Biol.* 4970–4980). An important consequence of cooperativity in the context of the transcription factor hijacking model is that a small decrease in the pool of free nuclear hUBF can strongly decrease promoter occupancy.

EXAMPLE 4

Competitive Inhibition of [hUBF-rDNA Promoter] Complexing by Cisplatin Decoys

From the comparable values of the hUBF affinity constants for cisplatin adducts and the rDNA promoter, it seemed likely that cisplatin adducts should be effective competitive inhibitors of [hUBF-promoter] complex formation. Accordingly, a competition study was carried out, using the probe preparation and DNase I footprinting techniques discussed in the preceding examples.

Competitive Technique. Purified HeLa UBF was added to all samples, except the negative control (shown in lane 1 of FIG. 5), to a final concentration of 160 pM. This level of hUBF is safely above that producing an apparent fractional saturation (Y) of 1 in the positive control (lane 2). The 5' labeled probe was present at 46 pM ($10^4$ cpm). Un-100 (lanes 3–6) and G^G-100 (lanes 7–12) were added as unlabeled competitors to the final concentrations (nM) listed.

The competitive effect was estimated by measuring Y of the promoter probe. Y values are shown at the bottom. Lanes 1 and 2 were used as standards to calculate Y in lanes 3–12.

Results. FIG. 5 shows that G^G-100 efficiently antagonized hUBF-promoter interactions. The reduced intensity of bands at positions −21 and −95 in the CORE and UCE elements, and the reappearance of bands between positions −75 and −115 illustrate this effect (lanes 7–12). At a saturating concentration of hUBF, the formation of promoter complexes was completely inhibited by a platinum adduct concentration of $5 \times 10^{-9}$ M (lane 11), which is well below the adduct levels in cancer patient DNA ($10^4$–$10^5$/cell, or $10^{-7}$–$10^{-6}$ M)(Reed et al. (1993), 53 *Cancer Res.* 3694–3699). The corresponding unmodified competitor DNA (Un-100) was a 10–30 fold weaker competitor of hUBF than G^G-100 (lanes 3–6). Since Un-100 contains up to 100 overlapping nonspecific binding sites compared to the one specific binding site in G^G-100, the preference of hUBF for a platinated versus an unplatinated site may be as high as $1-3 \times 10^3$ fold. These results directly support the view that cisplatin decoys effectively hijack hUBF, sequestering this transcription factor away from its endogenous genomic binding site and leaving the rDNA promoter unoccupied. From these results, disarray of the cellular protein synthesis machinery can be predicted.

EXAMPLE 5

Demonstration that a Heterobifunctional Compound can Mediate Binding of a Chosen Protein to a Genomic Lesion Site TMP-biotin lesion conjugate. A 17-mer oligonucleotide, referred to as U-17, was synthesized by standard phosphoramidite chemistry. U-17 comprised a single, centrally-located 5'-TA-3' site, along with a uracil deoxynucleotide located three bases away from the TA site on the 3' side. The oligomer was purified on a 20% denaturing (7 M urea) polyacrylamide gel (acrylamide/bis, 19:1) and electroeluted by using an Amicon centrilutor. Urea was removed from the oligomer by several distilled water washes in Amicon Centricon 3™ microconcentrators. Purified U-17 was 5'-end labeled with [γ-$^{32}$P] ATP (6000 Ci/mmole, New England Nuclear) by using T4 polynucleotide kinase (New England Biolabs) according to standard techniques. Unincorporated label was removed by centrifugation through a pre-packed G-25 column (Boehringer-Mannheim). Labeled U-17 was then annealed to its unlabeled complementary strand. TMP-biotin conjugate (dissolved in 50% (v/v) acetonitrile) was then added to the duplex oligmer solution with the molar ratio of TMP-biotin to base pair at about 1000:1. After being incubated at room temperature for 10 min, the mixture was placed on a chilled surface and subjected to near UV irradiation with a 15-W General Electric lamp (maximum output at 365 nm). The final irradiation dose was about 85 kJ/m$^2$. The resulting irradiated mixture, now comprising TMP-biotin lesioned U-17, was separated on a 20% denaturing polyacrylamide gel. A gel slice containing monoadducted TMP-biotin U-17 strand was cut out, and the lesioned DNA was purified by electroelution as described above. Finally, the lesioned U-17 strand was annealed to its cognate unlabeled complementary strand to form the double-stranded lesioned probe.

Gel Mobility Shift Assay. The binding of streptavidin to U-17 monoadducted with the TMP-biotin conjugate was measured by incubating the probe with streptavidin (Pierce) in 10 μl of binding buffer [25 mM Tris-HCl (pH 7.4), 100 mM NaCl and 1.5 MgCl$_2$] at room temperature for 10 min, and electrophoresing the mixture on a 5% nondenaturing polyacrylamide gel (acrylamide/bis, 29:1) at 4° C. A constant amount of the lesioned U-17 (3200 cpm, ~0.1 nM) was used in each incubation, with the concentration of streptavidin varied from 0 to 50 nM. Free d-biotin (0.4 mM) was added into the incubation(s) where indicated. After electrophoresis, the gel was dried and exposed to x-ray film with an intensifying screen. The dried gel was also exposed to a PhorphorImager screen and the data were analyzed with IMAGEQUANT software (Molecular Dynamics, Sunnyvale, Calif.).

Results. Streptavidin retarded the electrophoretic mobility of U-17 fragments monoadducted with the TMP-biotin conjugate (FIG. 6, Panel A). The retardation was caused by the binding of streptavidin to the biotin inserted into the DNA because free biotin reversed the retardation, presumably by competing with the immobilized biotin for streptavidin (lane 8 in Panel A). Quantitation of the data by IMAGEQUANT software of Molecular Dynamics gave rise to a binding curve (Panel B). The streptavidin concentration for the half-maximum binding ($C_{1/2}$) was about 1.5 nM, suggesting that the $K_d$ between streptavidin and the immobilized biotin was also about 1.5 nM. Streptavidin showed little binding activity to either U-17 oligomer or U-17 monoadducted with just a psoralen derivative (data not shown). It should be pointed out that the $K_d$ value differs quite significantly from that of free biotin with streptavidin or avidin. As discussed previously, the observed increase of this $K_d$ value was possibly attributable to steric effects exerted on the streptavidin-biotin binding by the adduction of TMP-biotin conjugates to DNA.

EXAMPLE 6

Demonstration that Lesion-Bound Streptavidin Hinders Access by a DNA Repair Enzyme Uracil Glycosylase Protection Assay. Double-stranded, TMP-biotin modified U-17 obtained as described earlier was used as the probe in this assay. The probe (4000 cpm, ~0.15 nM for each reaction) was incubated first in 12 μl of glycosylase buffer [30 mM Tris×HCl (pH 7.4), 50 mM KCl and 5 mM MgCl$_2$] at room temperature for 10 min in the presence of streptavidin (36 ng, ~50 nM) where indicated. In some incubations, 0.4 mM free d-biotin was added. After the incubation, 3 μl (0.15 units) of uracil glycosylase (Boehringer-Mannheim) was added, and the mixtures were then incubated at 37° C. for 5 min to 40 min. At the end of each incubation, 85 μl freshly prepared 1.25 M piperidine (Fisher) was added, and the samples were subsequently heated at 90° C. for 1 hr. Since an apurinic site in a DNA molecule is labile to alkali cleavage, Lindahl and Andersson (1972), 11 *Biochemistry* 3618–3623, piperidine treatment as stated above would have resulted in DNA strand breaks if any apurinic sites were generated from the uracil glycosylase treatment. The samples were vacuum centrifuged to remove the piperidine and washed by resuspension in distilled water and followed by vacuum centrifugation again. Washed samples were finally resuspended in denaturing loading buffer [80% (v/v) recrystallized formamide, 0.1% (w/v) xylene cyanol and 0.1% (w/v) bromphenol blue], analyzed on a 20% denaturing polyacrylamide gel. The gel was exposed (without being dried) to an x-ray film with an intensifying screen at −80° C.

Figure 7:
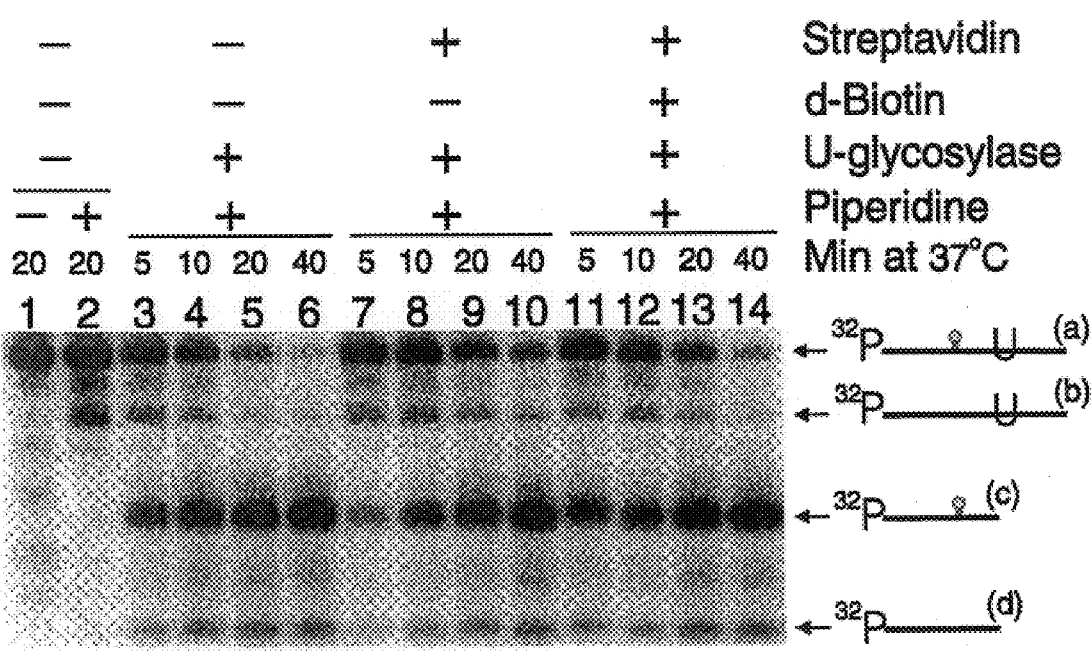
FIG. 7 presents autoradiograph results demonstrating inhibition of uracil gylcosylase by lesion-bound streptavidin. Bands (a) represent the full-length and intact probe used in each reaction. Bands (c) represent the products of uracil glycosylase treatments and the subsequent piperidine cleavages. Bands (b) and bands (d) are the breakdown products of bands (a) and bands (c) respectively due to the alkali liability of the adducts.

Results. As indicated in FIG. 7, streptavidin, when complexed with the TMP-biotin DNA adducts, inhibited the removal of a nearby uracil base by the uracil glycosylase (compare lanes 3–6 with lanes 7–10). The inhibition was substantially reversed when free biotin was added (lanes 11–14). The TMP-biotin DNA adducts were stable even after being heated at 90° C. for 1 hr (lane 1). A small fraction of the TMP-biotin adducts was removed when the probe was subjected to piperidine treatment [band (b) in lane 2; bands (b) and bands (d) in lanes 3–14].

EXAMPLE 7
Demonstration that Lesion-Bound Streptavidin Acts as a Steric Shield DNase I Protection Assay (Also Called DNase I Footprinting). Again, $^{32}$P end-labeled double-stranded U-17 modified with the TMP-biotin was used in this assay. Briefly, the lesioned DNA (5000 cpm, ~0.15 nM) was first incubated with various amounts of streptavidin (0–50 nM) at room temperature for 10 min in 10 μl of binding buffer [25 mM TrisxHCl (pH 7.4), 100 mM NaCl and 1.5 MM MgCl$_2$]. Where indicated, 0.4 mM free d-biotin was included in one of the incubations. At the end of each incubation, 2 μl of 2.5 mg/ml freshly diluted DNase I (Worthington Enzymes, Freehold, N.J.; final concentration, 0.4 mg/ml) was added, and the digestion was carried out at room temperature for 2 min before being quenched by the addition of 50 μl of stop solution [20 mM EDTA (pH 8.0), 1% SDS and 50 ug/ml yeast total RNA]. The samples were then precipitated by ethanol. After being washed once with 80% ethanol, the DNA pellets were air dried and then resuspended in denaturing loading buffer. Finally, the resuspensions were loaded onto a 20% denaturing polyacrylamide gel. The gel was dried, and exposed to an x-ray film with an intensifying screen at –80° C.

Figure 8:
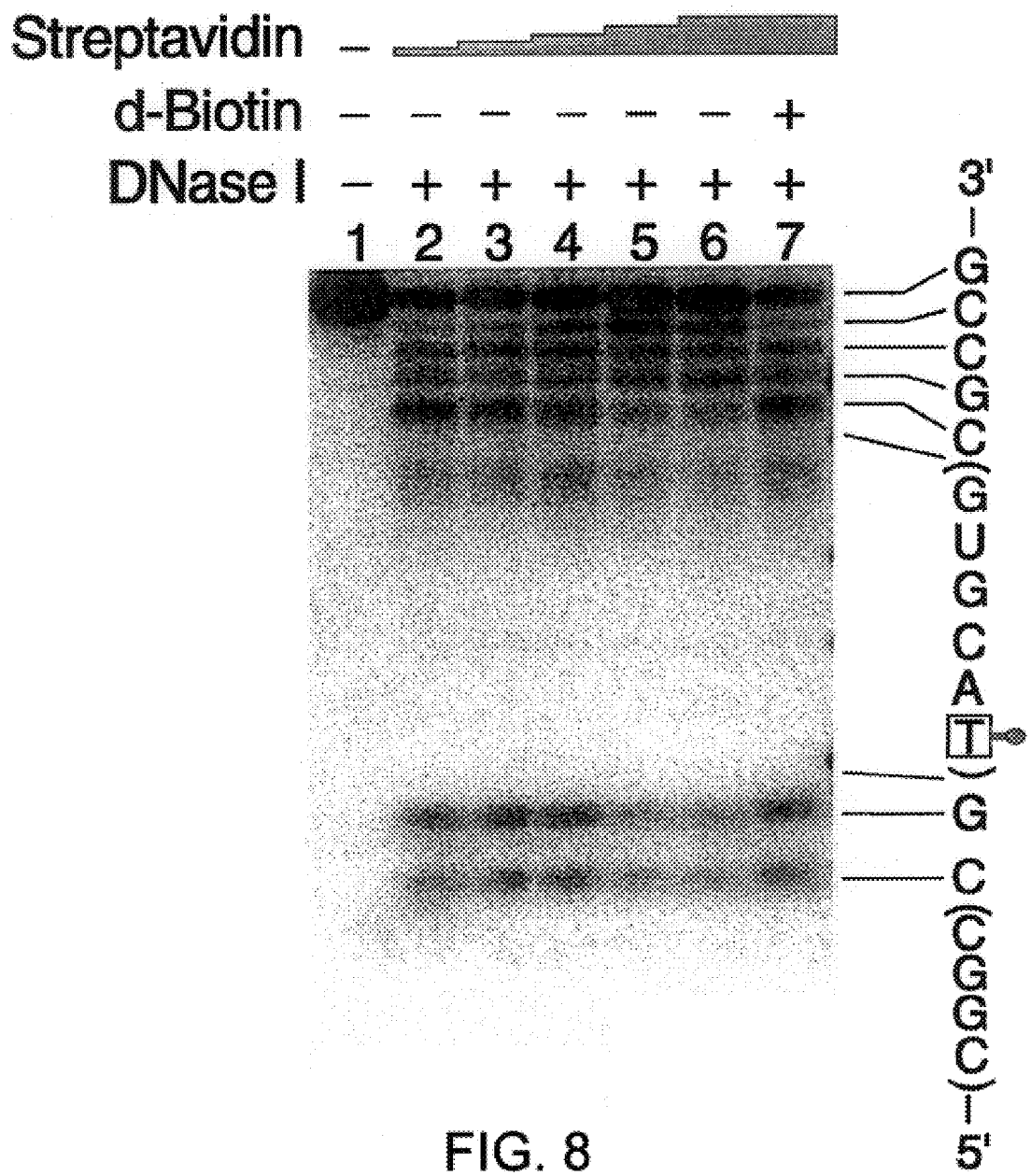
FIG. 8 presents autoradiograph results of a DNase I protection assay. 5000 cpm (~1.5 fmoles, ~0.15 nM) of the $^{32}$P end-labeled, TMP-biotin lesioned probe was used in each lane. 0 nM, 0.4 nM, 2 nM, 10 nM, 50 nM and 50 nM of stretavidin were used in lanes 2 to 7 respectively. In lane 7, 0.4 nM of free d-biotin was also included in the incubation. Where indicated, 5 μg of DNase I (final concentration, 0.4 mg/ml) was used in each digestion. The boxed thymidine base shown at right marks the position of the TMP-biotin monoadduct (SEQ ID NO:4).

Results. As shown in FIG. 8, when streptavidin was added, the modified U-17 became resistant to DNase I cleavage. Enhanced C$^{16}$ and G$^{17}$ bands indicated that streptavidin protected these fragments (full-length or one base less) from being further cleaved by DNase I. Since the lesioned DNA probe was 5' end-labeled, and fragments shorter than 5-mer could not be recovered by the ethanol precipitation used in the experimental procedures, only two bases (C$^5$ and G$^6$) on the 5' side of the modified thymidine were observed to be covered by streptavidin. On the 3' side, however, the covered region was more extensive. As discussed above, the protected region extended at least to the full-length of the probe, which was ten nucleotides away from the modified base. It is reasonable to expect that a similar length on the 3' side of the probe is also protected by streptavidin. These observations suggested that streptavidin, a protein of about 50 kD, covered at least twenty nucleotides flanking the thymidine where a TMP-biotin was monoadducted. DNA excision repair enzymes in mammalian cells, which are able to repair a variety of DNA damages (Friedberg (1985), *DNA Repair*) repair a DNA lesion first by recognizing it and then excising a "patch" or DNA fragment of 27- to 29-nucleotides flanking the lesion site on the damaged strand (Huang et al. (1992), 89 *P.N.A.S. USA* 3664–3668; Svovoda et al. (1993), 268 *J. Biol. Chem.* 1931–1936). It was noted that, even in the absence of streptavidin, a small region of 4–5 nucleotides on the 3' side of the modified thymidine resisted DNase I cleavage. It is possible that this effect was due to the presence of the TMP-biotin lesion itself. A similar effect would not be observed had the experiment been conducted with an appropriate repair enzyme instead of DNase.

PROSPECTIVE EXAMPLE 8
Guidelines for Demonstrating that a Heterobifunctional Compound forms Genomic Lesions The ability of a given programmed genotoxic compound, such as the nitrogen-mustard-steroid decoy estrogen-chlorambucil, to damage DNA can be assessed by determining the ability of the compound to form interstrand crosslinks between opposing strands of a duplex DNA molecule. Formation of such crosslinks is known to correlate strongly with the clinical efficacy of bifunctional mustards including chloramubicil and melphalen (Ross et al. (1978), 38 *Cancer Res.* 1502–1506; Zwelling et al. (1981), 41 *Cancer Res.* 640–649). The assay is both simple and rapid. It is based on the separation of DNA strands under denaturing conditions of heat and chaotropic compounds (e.g., urea), or organic solvents (e.g., N,N-dimethylforamide). When crosslinked, denatured DNA strands are unable to separate and consequently migrate more slowly than uncrosslinked separated strands during electrophoresis in polyacrylamide gels. After incubating the chosen compound with a short DNA duplex molecule labeled with $^{32}$P, the percentage of crosslinked DNA molecules can be determined following separation by gel electrophoresis according to standard methods. Conditions for crosslinking and gel analysis of both short DNA fragments (Rink et al. (1993), 115 *J. Amer. Chem. Soc.* 2551–2557) and longer DNA fragments (Hartley et al. (1 991), 193 *Anal. Biochem.* 131–134; Holley et al. (1 992), 52 *Cancer Res.* 4190–4195) have been described in detail. These methods can be adapted to assess the crosslinking of DNA fragments ranging in size from, e.g., duplex 17-mer oligonucleotides such as U-17, to the 166, 235, 540, 1423, and 3199 base pair fragments obtained from Dde I restriction endonuclease digest of the widely available pGEM plasmid.

Crosslinking capacity of a particular programmed heterobifunctional compound should be compared to that of the parent genotoxic agent (e.g., chlorambucil). The compound under investigation preferably has the ability to produce interstrand crosslinks in DNA in vitro that are comparable to those of the parent compound under similar conditions. If this is not the case, the reactivity of synthetic intermediates can be examined to determine what modification(s) to the parent genotoxic agent's structure is responsible for its reduced crosslinking activity. With this knowledge in hand, the structure of an optional linker or other component can be modified, if necessary, to restore reactivity of the genotoxic agent portion of the heterobifunctional compound to a desired level.

PROSPECTIVE EXAMPLE 9
Guidelines for Demonstrating that a Heterobifunctional Compound Binds to a Chosen Cell Component Tight association between the programmed genotoxic ligand compound estrogen-chlorambucil and the estrogen receptor protein is relevant to the compound's intended function. The strength of association of the ligand decoy receptor complex should be measured for both the "free" form of the compound, and the form that is covalently bound to DNA forming a genomic lesion. Knowledge of the interaction of the free form of the compound with the receptor can indicate whether the position of chemical attachment of the steroid ligand to the optional linker has preserved capacity to interact with the receptor protein. Comparison of the strengths of association of the free and DNA-bound forms of the compound should indicate whether or not the DNA molecule sterically impedes the formation of lesion-shielding complexes.

One of several routine and widely used assays can be employed for measuring the ability of the free compound to displace a natural steroid ligand from the estrogen receptor. Typically, radiolabeled estradiol is first bound to the receptor protein in a cell extract prepared from estrogen responsive tissue such as uterus. Calf uterus is most commonly used for this purpose. Increasing concentrations of the compound under investigation are then added. The amount of estradiol remaining tightly associated with the protein as a function of the increasing concentration of the other chemical provides a measure of the relative affinities of the natural and synthetic ligands for the receptor.

Where the compound under investigation has first been covalently attached to DNA, its association with the receptor protein can be investigated by gel electrophoresis using a routine adaption of mobility shift techniques described fully in Carthew et al. (1985), 43 *Cell* 439–448. DNA-receptor complexes can thus be electrophoretically resolved from lesioned, uncomplexed DNA through application or routine adaptation of this technique. Furthermore, the strength of the association can be measured by addition of competing ligands for the receptor as described in the previous examples. Increasing amounts of estradiol, for example, would compete with the DNA bound ligand for the receptor protein and thereby restrict formation of the DNA-receptor complex. The effectiveness of estradiol in preventing the formation of the DNA-receptor complex should provide a useful measure of the relative strength of association of the heterobifunctional ligand compounds with the receptor.

From the results of biomolecular studies such as those described above, it should be possible to predict the effectiveness of compounds under investigation for blocking repair of lesions in living cells.

PROSPECTIVE EXAMPLE 10
Guidelines for Demonstrating Efficacy of Ligand Decoy Compounds Specificity of heterobifunctional compounds, such as the estrogen-chlorambucil decoy, for killing tumor cells that express the estrogen receptor can be tested readily in available cell culture models for breast cancer. Results derived from these models will form appropriate grounds for reasonably predicting genotoxic effectiveness of candidate programmed heterobifunctional compounds for use in vivo. That is, effectiveness of the compounds in the present cell culture models will provide an early indication of genotoxic potential in multicellular organisms, such as mammals, including humans. For present purposes, breast cancer cell lines should be chosen for screening protocols because this form of cancer currently is the principle target for genotoxic uses of estrogen receptor decoys. Several human breast cancer cell lines are widely available and have been characterized as to their estrogen receptor status. The MCF-7 and MDA-MB-231 cell lines are two such examples. Estrogen receptor status plays a key role in determining the responses of these cell lines to estrogens and genotoxic antiestrogens such as tamoxifen. Estrogens stimulate the growth of the estrogen receptor positive cell line MCF-7, while having no effect on the growth rate of MDG-MB-231, which lacks the receptor. Likewise, antiestrogens such as tamoxifen inhibit the growth of MCF-7 cells, but have no effect on the growth of MDA-MB-231 cells. These two cell lines therefore allow a determination of whether compounds such as the estrogen-chlorambucil decoy are more effective than chlorambucil itself in killing cells that contain the target receptor. Thus, cell lines with high levels of estrogen receptor protein should be much more sensitive to the heterobifunctional decoy.

Cell sensitivity can be assessed using a growth inhibition assay. Equal concentrations of chlorambucil and the chlorambucil-estrogen conjugate can be added to cell cultures, and the rate of cell proliferation determined by counting the number of cells in replica cultures up to seven days post treatment. The increase in cell numbers in both treated and untreated control cultures can be compared to assess potential antitumor effects. Favorable results should be confirmed by repeating the test using a phenotypically different pair of receptor-bearing and receptor independent cell lines. Drugs that demonstrate a 2–4 fold or greater ability to inhibit the growth of estrogen receptor positive cells, as compared to receptor negative cells, should be selected for further testing in appropriate mammals.

EXAMPLE 11
In vitro Genetic Selection of a Pool of Aptamers that Bind Selectively to Mutant P53

Two 10-mer peptides (EP240-Cys: $NH_2$-Thr-Phe-Arg-His-Ser-Val-Val-Val-Pro-Cys-COOH (SEQ ID NO:1) and EP240S-Cys: $NH_2$-Thr-Phe-Val-His-Val-Ser-Arg-Val-Pro-Cys-COOH (SEQ ID NO:2)) were synthesized by standard techniques and coupled to a Thiol-Sepharose supporting matrix through the cysteine residues in the peptides. Peptide EP240-Cys comprises the five residue epitope recognized by PAb 240, shown underlined, and thus was used as the selection target peptide. Peptide EP240S-Cys, in which the epitope sequence is scrambled, was used to eliminate aptamers that bound non-sequence-specifically to the target peptide. The C-terminal cysteine residues, which do not exist in the native protein sequence, were attached to both peptides to facilitate immobilization onto thiol-derivitized agarose beads, and elution of the peptides along with the bound aptamer candidates under reducing conditions (e.g., 20 mM DTT). A pool of 100-Mer oligonucleotides containing a central 64-mer totally randomized sequence flanked by 18-mer PCR primer regions at each end was synthesized by standard techniques. About 90 pmoles of the oligonucleotides, representing no fewer than $10^{13}$ different molecules, were amplified by about 100-fold by PCR, using a 5' end-biotinylated primer for one of the two flanking regions. The unbiotinylated DNA strand was thereafter isolated by binding the double-stranded PCR products to a streptavidin column and eluting the column with 0.15 N NaOH. The amplified pool of single stranded candidate aptamers (about 900 pmoles) was first applied to a pre-selection column containing the scrambled EP240S-Cys peptides. This step was designed to eliminate nonspecific binding. The DNA flowthrough from the pre-column was directly loaded onto the selection column containing EP240-Cys epitope peptides. After extensive washing with binding buffer, the selection column was eluted with binding buffer containing 20 mM DTT. The eluted DNA was subjected to PCR amplification. Rounds of selection and amplification were repeated to generate a pool rich in candidate aptamers having the desired binding property. Nine rounds of selections were completed. Preliminary results indicated that a population of aptamers has been selected that bind preferentially to the selection column EP240-Cys and not to the pre-selection column EP-240S-Cys. Individual aptamers isolated from this pool can be subjected to assessment of their binding characteristics for mutant p53, and can be further developed as heterobifunctional compounds programmed to selectively destroy cells that express a recognized p53 mutant.

EXAMPLE 12
Preparation of a Heterobifunctional Genotoxic Compound Programmed to Attract the Estrogen Receptor to Genomic Lesion Sites 12.1 Overview of the Synthesis of a 2-Phenylindole-Nitrogen Mustard Compound of the Present Invention A ligand decoy compound designed to attract the estrogen receptor has been prepared according to the principles disclosed herein. This compound, which presently is preferred for achieving the selective killing of transformed human cells that express estrogen receptor, comprises a nitrogen mustard (chlorambucil) first agent linked through a protease resistant, hydrophilic organic linker to a 2-phenylindole second agent. The second agent ligand has been shown to bind effectively to mammalian estrogen receptor, even when the heterobifunctional compound is adducted to double-stranded DNA. The synthesis route employed for the preparation of this preferred compound, referred to herein as 2-phenylindole-C6NC2, is outlined in FIG. 9, in which like reference numerals identify the intermediate and product compounds referred to herein.

The first step involves alkylation of p-methoxyanisole with p-methoxy-2-bromopropiophenone (von Angerer et al. (1984), 27 *J. Med. Chem.* 1349.) Sequential treatment of 2 with BBr3 and MOM-Cl furnished the corresponding phenylindole 4. Alkylation of 4 with 1,6-dibromohexane afforded the bromide 5. Treatment of 5 with 1-diphenylphosphinamide-2-TBDMS-ethanolamine (6) produced 7, which underwent deprotection upon exposure to TBAF, generating the alcohol 8. Activation of the hydroxy group in the presence of p-nitrophenyl-carbonate followed by addition of 3-[4-[N,N-bis(2-chloroethyl)amino]-phenyl]-propylamine generated the carbamate 9. Acid hydrolysis of diphenylphosphinic and methoxymethyl groups afforded the desired heterobifunctional mustard-2-phenylindole compound 1. A more detailed discussion of the synthesis set forth in FIG. 9 follows.

12.2 Synthesis of 5-methoxy 2-(4-methoxyphenyl) indole (2)

A solution of p-methoxy-2-bromopropiophenone ((1 g, 4.11 mmol) was added to a solution of p-methoxyanisole in N,N dimethylaniline (1.7 g, 13.82 mmol)) and heated under reflux for 3 hours. The reaction mixture was cooled to room temperature, poured into 2N HCl, and extracted with EtOAc. The organic extract was washed with water and dried over $Na_2SO_4$. Removal of the solvent under reduced pressure and flash chromatography on $SiO_2$ using $CH_2Cl_2$ gave the desired intermediate compound 2.

12.3 Synthesis of 5-hydroxy 2-(4-hydroxyphenyl) indole (3)

Five g (18.7 mmol) of 5-methoxy 2-(4 methoxyphenyl) indole was dissolved in 30 mL $CH_2Cl_2$ under argon, cooled on dry ice/acetone and 70 mL 1 M $BBr_3$ were added with stirring. The solution was warmed to 0° C. for 30 min. It was then stirred at room temperature overnight. The reaction mixture was suspended in sat. $NaHCO_3$ solution and extracted with $CH_2Cl_2$ (2×). The organic extract was washed with brine and dried over $Na_2SO_4$. Removal of the solvent in vacuo and flash chromatography (5% MeOH in CH2Cl2) gave 3.33 g of 3.

12.4 Synthesis of 5-O-methylmethoxy-2-(4-O-methoxy-methylphenyl)indole (4)

Three g (12 mmol) of 5-hydroxy-2-(4-hydroxyphenyl) indole was dissolved in 50 mL dry THF under argon. After cooling the solution on dry ice/acetone, 1.92 g of MOM Cl and 0.58 g of NaH were added. The reaction mixture was cooled to room temperature, stirred for 1 hour and washed with water. The organic layer was dried over $Na_2SO_4$ and evaporated under reduced pressure. The product was isolated by flash chromatography which gave 2.5 g (60%) of 4.

12.5 Synthesis of 1-(6-bromohexyl)-5-O-methoxymethyl-2-(4-O-methoxymethylphenyl) indole (5)

Sodium hydride (0.25 g of a 50% dispersion in oil, 5.14 mmol) was suspended in 50 mL of dry DMF, and cooled to 0° C. under argon. 5-O-methoxy-methyl-2-(4-O-methoxymethylphenyl)indole (1.0 g, 3.0 mmol) was added slowly to the reaction mixture. The mixture was stirred for 1 hour at room temperature and then 1,6 dibromohexane (4.5 g, 18.44 mmol) in 30 mL DMF was added dropwise. After stirring for 2 hours, the reaction was quenched with water and extracted with ether. The organic phase was washed with water (3×) and dried ($Na_2SO_4$). The oily residue was purified by flash chromatography ($CH_2Cl_2$) affording 5: 1.1 g (75%).

12.6 Synthesis of 1-diphenylphosphinamide-2-O-TBDMS-ethanolamine (6)

Five g (21.2 mmol) of diphenylphosphinic chloride was dissolved in 20 mL of dry pyridine. $NH_3$ was bubbled through the stirred solution till saturation occurred. The solution was stoppered and allowed to stir at room temperature for 2 hours. The reaction mixture was concentrated under reduced pressure and the residue dissolved in $CH_2Cl_2$. The solution was extracted with sat. $NaHCO_3$ and brine. The organic layer was dried over $Na_2SO_4$ and concentrated to dryness under reduced pressure. The resulting compound (1.0 g) was suspended in a biphasic mixture of 15 mL of benzene and 15 mL of 50% NaOH containing 40 mg tetra-n-butylammonium bromide. To the refluxing suspension was added 1 g (4.2 mmol) of 1-bromo-2-TBDMS-ethanol dissolved in 5 mL benzene (1-bromo-2-TBDMS-ethanol was prepared from 5 g 1-bromoethanol, 10 g of t butyldimethylsilyl chloride and 9.5 g imidazole, which were dissolved in 12 mL DMF and stirred overnight at room temperature). After refluxing for 4 hours, the organic layer was removed, extracted with water (3×), and dried over $Na_2SO_4$. Benzene was removed under reduced pressure and 0.25 g of the product was isolated from the oily residue by flash chromatography (3% MeOH in $CH_2Cl_2$).

12.7 Synthesis of 1-[6-(N-diphenylphosphinamide-2-ethanolamine)hexyl]-5-O-methoxymethyl-2-(4-O-methoxy-methylphenyl)indole (8)

A mixture of bromide (6) (0.25 g, 0.5 mmol), 1-diphenylphosphinamide-2-O-TBDMS-ethanolamine (0.25 g, 0.7 mmol), NaH (24 mg, 1 mmol), and a catalytic amount of tetrabutylammonium bromide were refluxed in benzene for 3 hours. The reaction mixture was cooled, extracted with water (2×) and dried over $Na_2SO_4$. The solvent was removed under reduced pressure and the resulting clear oil was purified by flash chromatography giving 0.4 g (0.5 mmol) of 7. Desilylation of the product was carried out in 5 mL dry THF in the presence of 1 mmol of tetrabutylammonium fluoride (1.0 mmol) at room temperature for 2 hours. The solvent was removed under reduced pressure, and the residue was dissolved in $CH_2Cl_2$ and extracted with water. After drying over $Na_2SO_4$, 0.3 g (0.44 mmol) of the product (8) was obtained as a viscous liquid.

12.8 Synthesis of 1[6(N diphenylphosphinamide 2 ethoxy-(O-(3-(4-(N,N-bis(2-chloroethyl) aminophenyl)propylamine)carbamoyl)amine)-hexyl]-5 O-methoxymethyl-2 (4 O methoxymethylphenyl)indole (9)

The alcohol (8) (0.3 g, 0.44 mmol) in 5 mL of dry pyridine was slowly added to a stirred solution of p-nitrophenylchloroformate (0.25 g, 1.2 mmol) in 2 mL of $CH_2Cl_2$. After stirring at room temperature for 1 hour, the reaction was diluted with $CH_2Cl_2$ and washed with sat. $NaHCO_3$ (3×) and brine. The resulting oily residue was purified by flash chromatography (2% MeOH in $CH_2Cl_2$). This activated alcohol (0.4 g) was added to a solution of 3-[4-[N,N-bis(2-chloroethyl)amino]-phenyl]propylamine (0.25 g, 1.0 mmol) in THF containing TEA (0.18 mL, 1.3 mmol) and refluxed for 45 min. The reaction mixture was cooled and the solvent was removed under reduced pressure. The residue was dissolved in $CH_2Cl_2$ and extracted with $NaHCO_3$ (3×) and brine. After drying over $Na_2SO_4$ and concentration under reduced pressure, 0.35 g of the product was isolated by flash $SiO_2$ chromatography (4% MeOH in $CH_2Cl_2$) as a viscous liquid.

12.9 Synthesis of 1-[6-(N-2-ethoxy-(O-(3-(4-(N,N-bis(2-chloroethyl)-aminophenyl)propylamine) carbamoyl)amine)hexyl]-5-O-hydoxy-2-(4-hydroxyphenyl)indole (1)

To a solution of 0.35 g of 9 in 5 mL of MeOH was added concentrated HCl (0.3 mL). After stirring 4 hours at room temperature, the solvent was removed under reduced pressure and the resulting residue was dissolved in 2% MeOH in $CH_2Cl_2$ and washed with sat. $NaHCO_3$ (2×) and brine. Drying over $Na_2SO_4$ and purification by flash chromatography gave 200 mg of 1, the desired programmed heterobifunctional genotoxic compound.

EXAMPLE 13
Demonstration that the 2-phenylindole-C6NC2-mustard Ligand Decoy Compound 1 Binds Effectively to Estrogen Receptor (ER)

An in vitro competition assay utilizing calf uterine extracts as the source of estrogen receptor (ER) was used according to the guidelines set forth in Example 9 (above), to determine the relative affinity of 2-phenylindole-C6NC2-mustard (1) and related compounds for the mammalian ER. The receptor-protein assay was performed as described by Korenman (1969), 13 *Steroids* 163. Briefly, uterine cytosol was prepared by homogenizing calf uteri in 0.01 M Tris-HCL pH 8.0, 1 mM EDTA, 0.25 M sucrose and centrifuging the homogenate at 105,000 g for 1 hr. The resulting supernatant was stored in liquid $N_2$. Assays were performed by premixing a range of concentrations of the test compound with a fixed amount of tritium labeled estradiol ($[^3H]E_2$). Calf uterine cytosol was then added. After incubation overnight at 4° C., activated charcoal/dextran was added to remove unbound $[^3H]E_2$. Following centrifugation to remove the charcoal/dextran, levels of bound (i.e., non-competed) $[^3H]E_2$ were determined by liquid scintillation spectrometry. Low concentrations of test compound required to abolish $[^3H]E_2$ binding in this assay indicate a tight association between the test compound and the ER.

This competition assay was used to determine the binding affinities for the estrogen receptor of the 2-phenylindole-C6NC2-mustard and its congeners (comprising the first and second agents of 1, linked through organic linkers of varying length), as well as DNA lesions containing the 2-phenylindole second agent formed by reaction of these compounds with purified and isolated DNA. In the latter case, various levels of 2-phenylindole-C6NC2-mustard were used to modify plasmid DNA, and residual unbound test compound was removed from the modified DNA by ethanol precipitation and multiple ethanol/water washes. The purified plasmid DNA containing 2-phenylindole-C6NC2-mustard lesions then was combined with $[^3H]E_2$ and used in the competition assay as described above.

Figure 10:
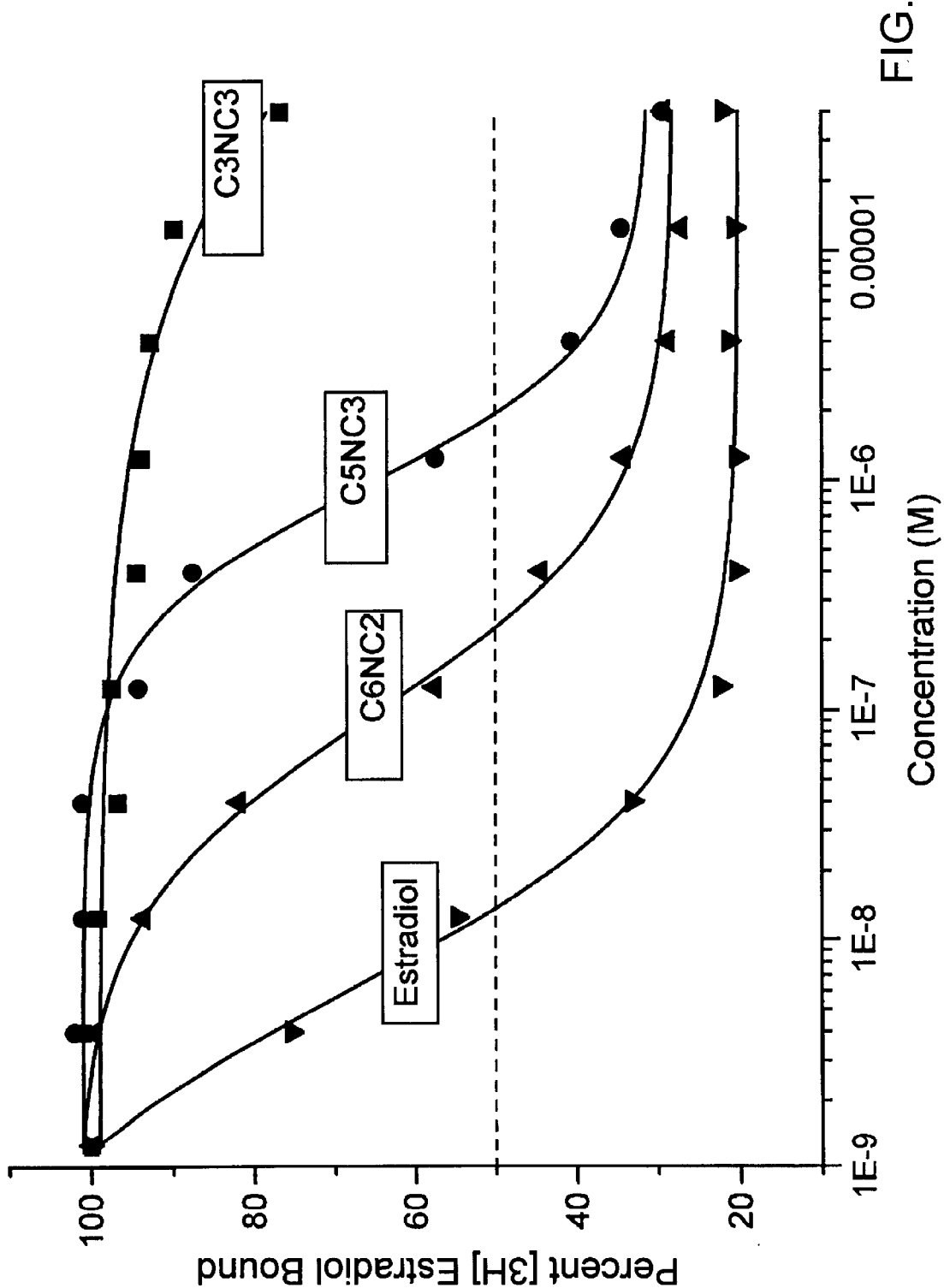
FIG. 10 presents a quantitative plot of results of competition studies establishing the relative affinities of heterobifunctional compounds comprising a 2-phenylindole second agent for the estrogen receptor (ER).

Results with the free 2-phenylindole compounds are shown in FIG. 10. The 2-phenylindole-C6NC2-mustard compound has the highest affinity for the ER. The affinity of this ligand decoy for the ER is within about 20 fold that of the natural ligand, estradiol (E2). The homologous 2-phenylindole-C5NC3-mustard compound has a lower affinity for the ER, about 200 times less than E2, while the homologous 2-phenylindole-C3NC3-mustard has little, if any, affinity for the ER. As noted previously, these compounds differ from the preferred 2phenylindole-C6NC2-mustard, compound 1 in FIG. 9, by the number of $CH_2$ groups disposed on either side the central NH group of the linker. These homologous compounds were prepared by routine modifications of the synthesis scheme discussed in Example 12.

Figure 11:
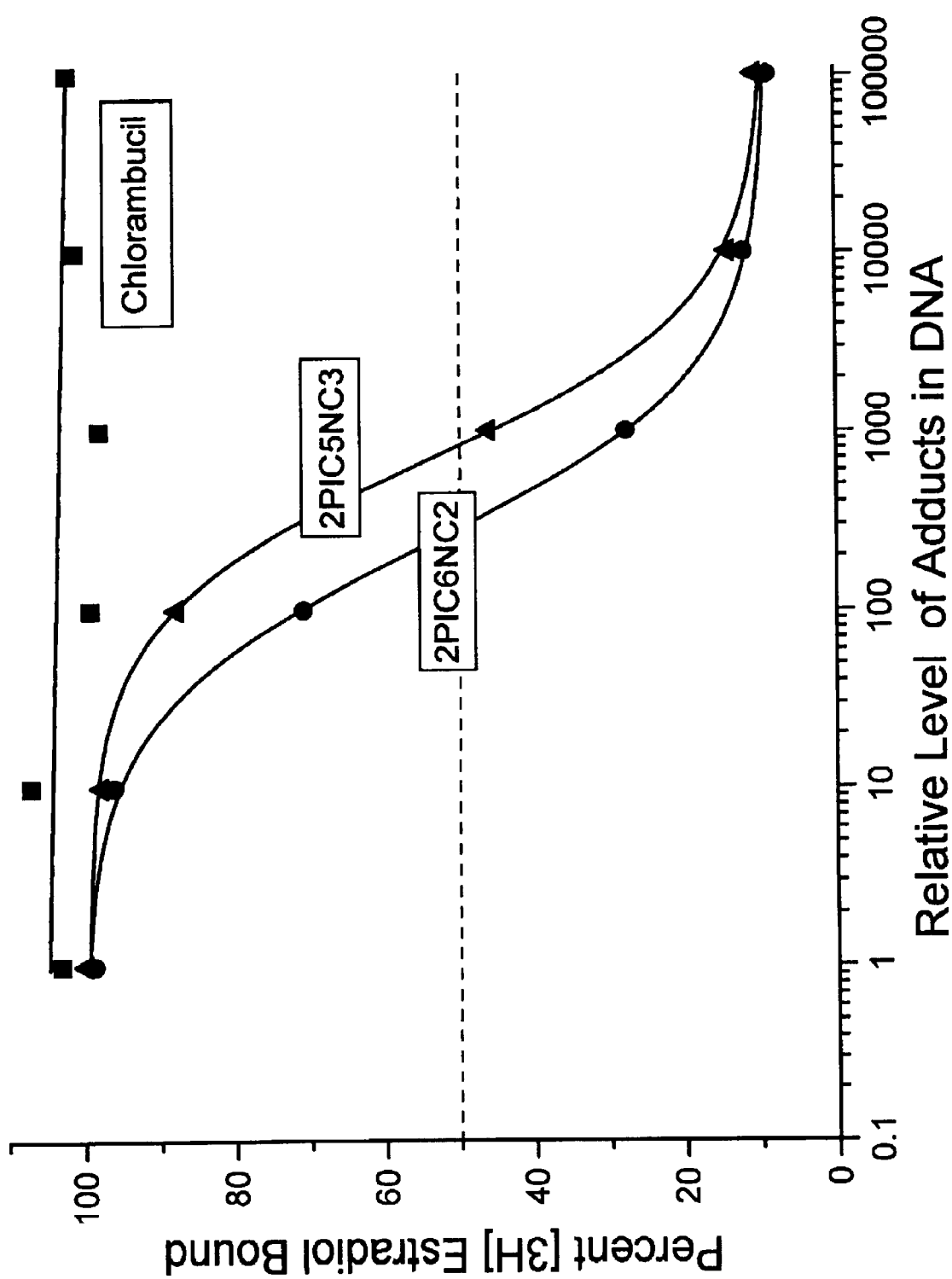
FIG. 11 presents a quantitative plot of results of competition studies establishing that ER affinity of two of the compounds assessed in FIG. 10 is retained when the compounds are adducted covalently to DNA.

FIG. 11 shows results of receptor competition assays using isolated DNAs lesioned with the preferred 2-phenylindole-C6NC2-mustard (1), 2-phenylindole-C5NC3-mustard, or the underivatized chorambucil mustard. These data show that DNA lesions formed by chlorambucil have no affinity for ER, while those formed by compounds of the present invention compete effectively with $E_2$ for ER. These results demonstrate that the 2-phenylindole first agent can attract ER to genomic lesions, providing reasonable basis for the expectation that compounds of the present invention, including particularly the preferred compound 1, can localize the sterically large ER at genomic lesions in vivo, thereby hindering access by cellular repair enzymes.

The results set forth in FIGS. 10 and 11 further demonstrate optimization of the optional linker disposed between the first and second agents of ligand decoy compounds programmed to attract the mammalian ER. Similar optimization studies can be carried out with other heterobifunctional compounds designed according to the principles disclosed herein to attract other cell components. It should be expected that the characteristics of the linker will vary depending in part on the particular cell component attracted by a chosen heterobifunctional genotoxic compound.

EXAMPLE 14
Demonstration that the 2-phenylindole-C6NC2-mustard Ligand Decoy Compound 1 is Toxic Selectively to Mammalian Cells Expressing Estrogen Receptor (ER)

The toxicities of the preferred 2-phenylindole-C6NC2-mustard and homologous ligand decoy compounds for selected cells distinguished phenotypically from nonselected cells by expression of ER were tested using the human breast tumor cell lines, MCF-7 and MDA-MB-231, according to the guidelines set forth in Example 10 (above). The MCF-7 cell line expresses the estrogen receptor protein, while no ER protein can be detected in the MDA-MB-231 cell line.

14.1 Cell culture conditions

Both cell lines were routinely cultured in Minimal Essential Medium (MEM) supplemented with 2 mM gluatamine, 1 mM sodium pyruvate and 10% fetal calf serum. To determine the toxicity of test compounds, cells were trypsinized and plated in 100 µl of media in 96-well microtiter plates at the following densities: MCF-7, 2000 cells/well; MDA-MB-231, 1000 cells/well. Cells were allowed to grow for 24 hours in the 96-well plates prior to treatment with the compounds.

14.2 Treatment of cells

All ligand decoy compounds were prepared as 10 mM stock solutions in dimethyl sulfoxide (DMSO). Compounds were initially diluted to 2 mM in DMSO. Subsequent dilutions were conducted in the appropriate tissue culture medium. The final concentration of DMSO under the testing conditions was 0.25%. In a control study, the mustard portion of the test compound was first inactivated by hydrolysis. This was carried out by heating the compound at 70° C. for 6 hrs. in a solution containing 50% DMSO and 50% 20 mM Hepes, pH 8.0. Hydrolysis of the mustard groups was verified by analysis by HPLC. The final concentration of DMSO in the media of cells treated with hydrolyzed compounds was 0.1%.

Each treatment condition was conducted in replicates of 8 wells. Treatment of the cells was carried out for either 4 hrs or 4 days, as indicated below. For the 4 hr treatment, media containing the test compound was aspirated from the wells and replaced with fresh media. For the 4 day treatment, cells remained in the original media containing the compound for the duration of the assay. On day 4, cell growth in treated and control cultures was determined using the methylene blue dye binding assay.

14.3 Methylene blue dye binding assay

A dye-binding assay as described by Finlay et al. (1984), 139 *Anal. Biochem.* 272 was used to assess the cytotoxic effects of 2-phenylindole-C6NC2-mustard and homologous ligand decoy compounds. For this assay, the media was aspirated from each of the wells, and replaced with 100 µl of 0.5% methylene blue in 50% ethanol. The dye solution remained on the cells for 30 min., after which the excess unbound dye was removed by several successive washes with water. The stained cells were allowed to air dry for 1–2 hours, then the bound dye was solubilized by adding 100 µl of 1% sarkosyl in phosphate buffered saline. The absorbance of the solubilized dye was read at 620 nm in a Ceres 9000 plate reader (Biotek).

Figure 12:
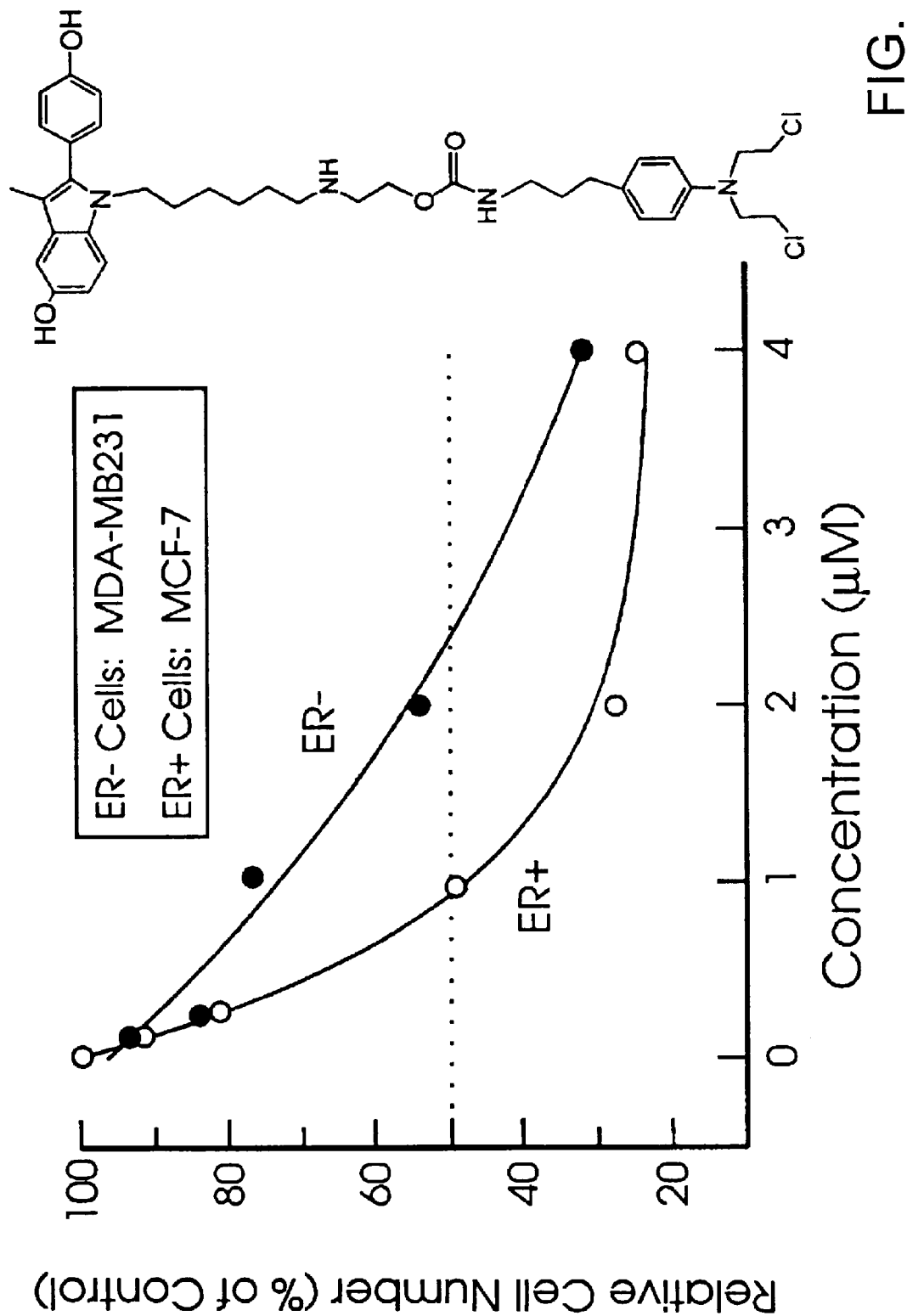
FIG. 12 presents a quantitative plot of results of cellular toxicity studies establishing that a preferred heterobifunctional ER decoy compound (1) of the present invention having the structure shown at the right of FIG. 12 (inset), is toxic selectively in human breast carcinoma cells expressing ER.

Results of a typical study are shown in FIG. 12, and establish that the $ED_{50}$ (the concentration that inhibits cell growth by 50%) of the preferred 2-phenylindole-C6NC2-mustard in MCF-7 ER positive breast cancer cells two- to three-fold lower than the $ED_{50}$ of the same compound in MDA-MB-231 ER negative breast cancer cells. This demonstrates that the presently preferred ligand decoy compound, prepared according to the principles of the present invention, is toxic selectively to breast cancer cells that are phenotypically distinguishable from nonselected cells by their expression of the ER.

EXAMPLE 15

Demonstration that Selective Toxicity of the 2-phenylindole-C6NC2-mustard Ligand Decoy Compound 1 is not Due to Antiestrogenic Activity The anticancer drug tamoxifen is toxic selectively to ER expressing breast cancer cells due to its antiestrogenic activity. A novel assay system accordingly was developed, using genetic engineering techniques, to distinguish among several possible mechanisms that could be responsible for the selective toxicity observed in FIGS. 12 and 13.

15.1 Construction of novel HeLa-derived cell lines

Isogenic cell lines, expressing functional estrogen receptor (ER) protein or a control therefor, were established to determine whether the selective toxicity of the preferred 2-phenylindole-C6NC2-mustard was attributable to an antiestrogenic activity or another mechanism of action, such as selective genotoxicity, e.g., according to the steric shielding model of FIG. 1. HeLa cells were stably transfected by the technique of lipofection (as described by Felgner et al. (1987), 85 *PNAS* 7413) with a eukaryotic expression vector containing the wild type ER gene (Tora et al. (1989), 8 *EMBO J.* 1981). The ER gene was in either the sense or antisense orientation under transcriptional control of the cytomegalovirus (CMV) promoter. Three days after lipofection, cells were replated at low density and selected for neomycin resistance in media containing 500 µg/ml G418 for 9 days. Resistant colonies were isolated and tested for the presence of functional ER protein by using a tritium-labeled estradiol ($[^3H]E_2$) binding assay as described by Olea-Serrano et al. (1985), 21 *Eur. J. Cancer Clin. Oncol.* 965. Briefly, cells were derived from single G418-resistant clones were seeded into separate wells of tissue culture plates and incubated for 3 days with estrogen free media to remove endogenous estrogens. $[^3H]E_2$ was added for 1 hr., after which the cells were washed with PBS several times to remove unbound $[^3H]E_2$. The remaining $[^3H]E_2$ was solubilized in ethanol and the amount of $^3H$ radioactivity associated with the cells was determined by liquid scintillation spectrometry.

Several clones with high levels of $[^3H]E_2$ binding activity were selected. The highest levels of binding, observed in clone HeLa 36, were comparable to level of $[^3H]E_2$ binding found in the ER-positive human breast cancer cell line, MCF-7. The ability to bind $[^3H]E_2$ established the capacity of these cells to express stably functional ER protein.

Similar analysis of control cells transfected with the CMV expression vector in which the ER gene was in the antisense orientation revealed no detectable $[^3H]E_2$ binding activity in G418 resistant cells. This established that the stable transfectants lacked functional ER protein. One such ER negative control clone used in the following toxicity studies was designated HeLa 7.

15.2 Selective toxicity of 2-phenylindole-C6NC2-mustard 1 in HeLa 36 Cells, Expressing ER but insensitive to antiestrogenic activity Stable HeLa transfornants expressing functional ER (HeLa 36) or control therefor (HeLa 7) were cultured in Dulbecco's Modified Eagles Medium (DMEM) supplemented with 2 mM glutamine, 1 mM sodium pyruvate and 10% fetal calf serum. All cells were grown in 75 cm² flasks and subcultured every third day by trypsinization.

Selective toxicity of the 2-phenylindole-C6NC2-mustard and homologous ligand decoy compounds in the HeLa ER transformants was assessed essentially as described above in Example 14, except that cells initially were seeded at 1500 cells/well for the HeLa 7 and 2000 cells/well for the HeLa 36 cell lines.

Figure 13:
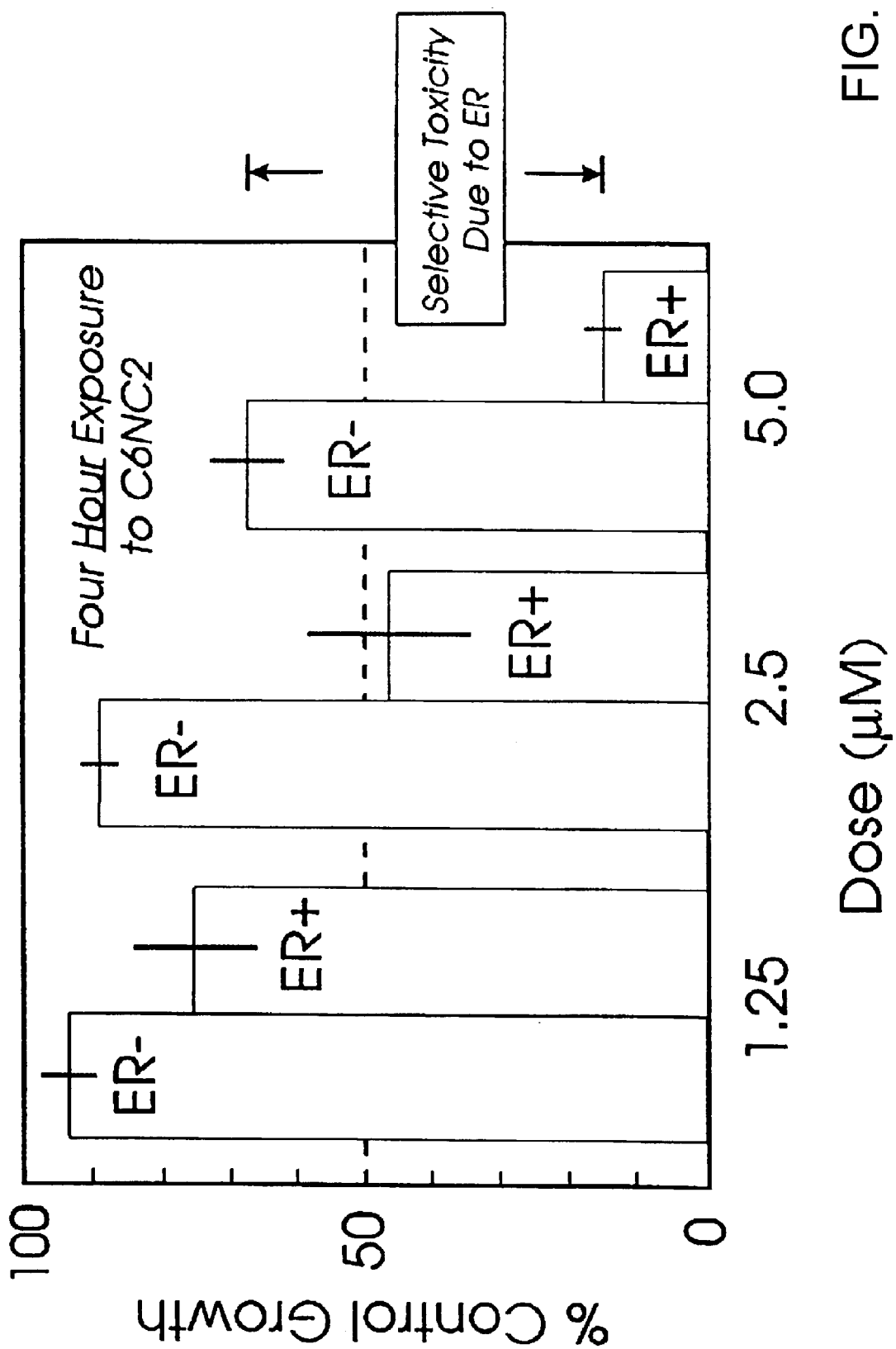
FIG. 13 presents a quantitative bar graph of results of 4 hour cellular toxicity studies establishing that a preferred ER ligand decoy compound (1) is toxic selectively to HeLa cell transformants expressing functional ER (ER+), and is relatively nontoxic to HeLa cells transformed with a control, antisense ER expression vector (ER–).
Figure 14:
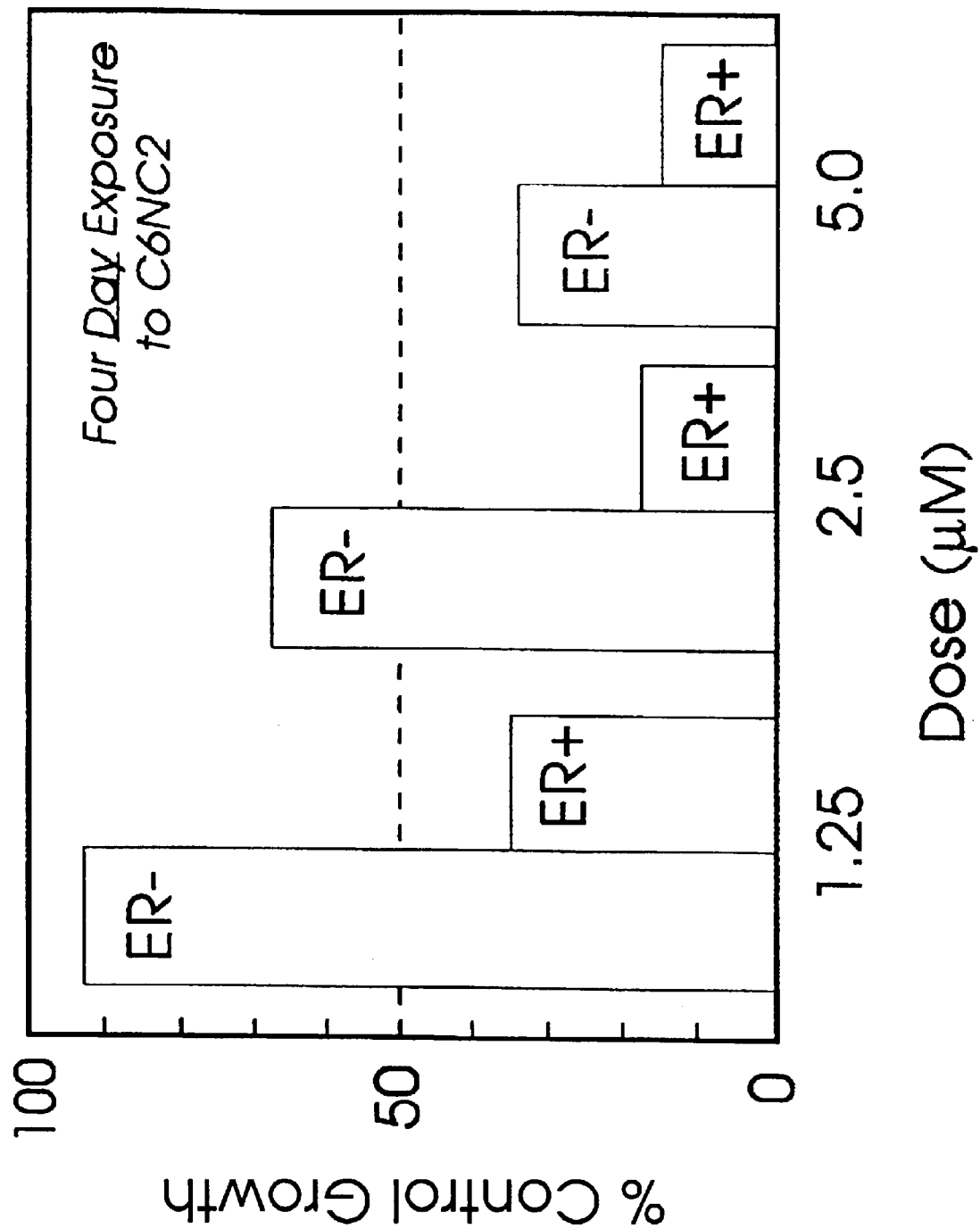
FIG. 14 presents a quantitative bar graph of results of 4 day cellular growth inhibition studies establishing that a preferred ER ligand decoy compound (1) is growth inhibitory to ER+ transformed HeLa cells, and is relatively nontoxic to ER transformed HeLa cells.

Cytotoxicity and growth inhibitory results for the preferred 2-phenylindole-C6NC2-mustard in HeLa 7 cells and HeLa 36 cells are shown in FIGS. 13 and 14, respectively. FIG. 13 sets forth results establishing that a 4 hr. exposure to a 5 µM dose of the preferred heterobifunctional ligand decoy compound produces a four- to five-fold greater cytotoxicity in HeLa 36 cells than in HeLa 7 cells, which lack functional ER. A similar exposure period to a 2.5 µM dose of the same compound produced approximately a two-fold differential in toxicity between these cell HeLa cell lines. FIG. 14 sets forth results demonstrating that a longer (4 day) exposure to the presently preferred ligand decoy compound consistently produced a selectively toxic and growth inhibitory effect in HeLa 36 cells, expressing the recognized ER cell component, relative to the control HeLa 7 cells, lacking the recognized cell component.

Figure 15:
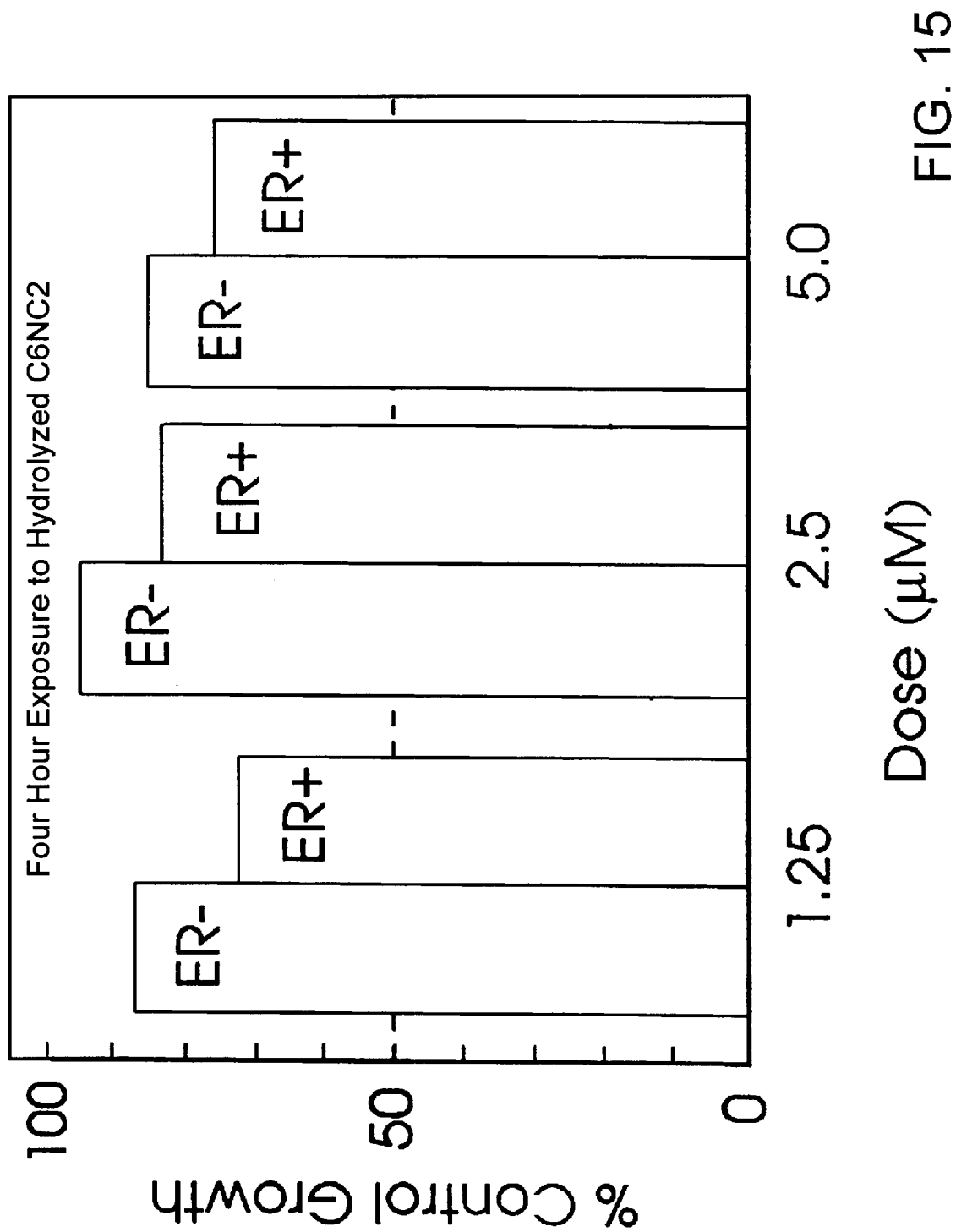
FIG. 15 presents a quantitative bar graph of results of control toxicity studies establishing that the selective toxicity results set forth in FIG. 13 depend upon the genotoxicity of the first agent (e.g., chlorambucil), rather than on a possible antiestrogenic activity of the second agent (2-phenylindole).

A control study, results of which are set forth in FIG. 15, established that the above-observed selective cytotoxicity is dependent on the structural integrity of the genotoxic first agent (chlorambucil) of the presently preferred compound. No significant cytotoxic effect was observed in either HeLa 7 or HeLa 36 cells following 4 hr. exposures to up to 5 µM doses of a chemically hydrolyzed preparation of 2-phenylindole-C6NC2-mustard. These results establish that the observed selective cytotoxicity of a preferred ligand decoy compound (1) is not due to antiestrogenic activity.

EXAMPLE 16

Synthesis of Heterobifunctional Genotoxin with Estradiol as a Second Agent

Another exemplary improved compound has been prepared which employs estradiol as the second agent 9. This compound, referred to herein as 7α-estradiol-C6NC2-mustard, includes an estradiol moiety linked at the 7α position through a protease resistant, hydrophilic, organic linker to an aromatic nitrogen mustard.

The 7α-estradiol-C6NC2-mustard was synthesized, and its selective cytotoxicity confirmed in target cells that express an estrogen receptor. The 7α-estradiol-C6NC2-mustard is an analog of a 2-phenylindole-linked nitrogen mustard disclosed in co-pending U.S. patent application Ser. No. 08/434,664, filed May 4, 1995, which is now allowed, the teachings of which are herein incorporated by reference. The improved estradiol-linked mustard described herein has a greater affinity for the estrogen receptor and shows greater specificity in its cytotoxic effects toward cells that express the estrogen receptor. These results corroborate earlier teachings regarding the design, construction and testing of compounds within the amended generic claims.

For example, estradiols with substituents at 17α, and 11β positions have been prepared and evaluated as diagnostic reagents for imaging receptor positive tumors. Pomper et al. (1990), 33 *J. Med. Chem.*, 3143–3155; Salman, et al. (1991), 56 *Steroids* 375; Napolitano et al. (1995), 38 *J. Med. Chem.* 429–434. Small lipophilic groups at the 11β position of estrogens have been shown to increase affinities for the receptor up to 30-fold as compared with estradiol. Bindal et al. (1987) 28 *J. Steroid Biochem.* 361–370.

Figure 16:
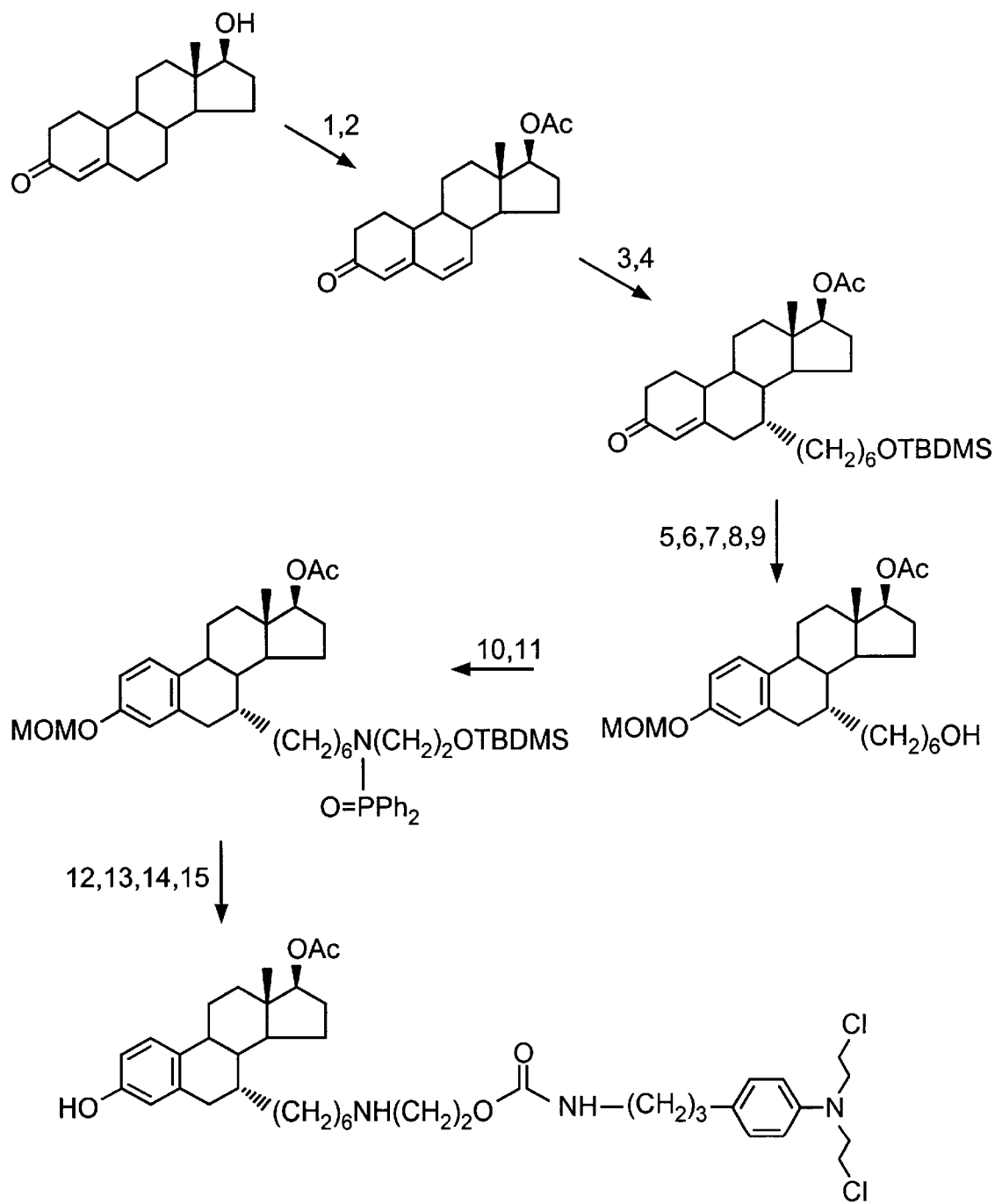
FIG. 16 presents a flow chart summarizing a chemical synthesis scheme for preparing another preferred heterobifunctional compound 10 of the the invention, demonstrated herein to be toxic selectively to cells that express estrogen receptor.

FIG. 16 illustrates the steps used to synthesize the 7α-estradiol-C6NC2-mustard. The bers in FIG. 16 refer to specific reagents or separation steps. The key to the bers in FIG. 16 is as follows:

| Ref. No. | Reagant or Separation Step |
|---|---|
| 1 | AcCl/Ac$_2$O/DMAP/pyridine |
| 2 | NBS/Li$_2$CO$_3$/LiBr/DMF |
| 3 | MgBr(CH$_2$)$_6$OTBDMS/CuI/THF |
| 4 | Separation of α and β isomers by flash chromatography |
| 5 | Bu$_4$N$^+$F$^-$/THF |
| 6 | Ac$_2$O/DMAP/pyridine |
| 7 | CuBr$_2$/LiBr/CH$_3$CN |
| 8 | (i-Pr)$_2$NEt/CH$_3$OCH$_2$Br |
| 9 | K$_2$CO$_3$/aq. CH$_3$OH |
| 10 | CH$_3$SO$_2$Cl/LiBr/DMF |
| 11 | Ph$_2$P(O)NH(CH$_2$)$_2$OTBDMS/NaH/DMF |
| 12 | Bu$_4$N$^+$F$^-$/THF |
| 13 | p-ClCO$_2$C$_6$H$_4$NO$_2$/(i-Pr)$_2$NEt/CH$_2$Cl$_2$ |
| 14 | p-((ClCH$_2$CH$_2$)$_2$N)C$_6$H$_4$(CH$_2$)$_3$NH$_2$/(i-Pr)$_2$NEt/THF |
| 15 | HCl/CH$_3$OH |

Ref. No. Reagant or Separation Step
1 AcCl/Ac$_2$O/DMAP/pyridine
2 NBS/Li$_2$CO$_3$/LiBr/DMF
3 MgBr(CH$_2$)$_6$OTBDMS/CuI/THF
4 Separation of α and β isomers by flash chromatography
5 Bu$_4$N$^+$F$^-$/THF
6 Ac$_2$O/DMAP/pyridine
7 CuBr$_2$/LiBr/CH$_3$CN
8 (i-Pr)$_2$NEt/CH$_3$OCH$_2$Br
9 K$_2$CO$_3$/aq. CH$_3$OH
10 CH$_3$SO$_2$Cl/LiBr/DMF
11 Ph$_2$P(O)NH(CH$_2$)$_2$OTBDMS/NaH/DMF
12 Bu$_4$N$^+$F$^-$/THF
13 p-ClCO$_2$C$_6$H$_4$NO$_2$/(i-Pr)$_2$NEt/CH$_2$Cl$_2$
14 p-((ClCH$_2$CH$_2$)$_2$N)C$_6$H$_4$(CH$_2$)$_3$NH$_2$/(i-Pr)$_2$NEt/THF
15 HCl/CH$_3$OH

16.1 Preparation of 19-nortestosteroneacetate-3-enolacetate

A solution of 19-nortestosterone in acetic anhydride (Ac$_2$O), pyridine, and acetyl chloride (AcCl) was heated at reflux under an argon atmosphere for 2.5 hr, then concentrated to near dryness. The residue was dissolved in methylene chloride (CH$_2$Cl$_2$) and washed with water and brine, The organic phase was dried over sodium sulfate (Na$_2$SO$_4$) and the solvent removed under reduced pressure. The product was isolated by flash chromatography on SiO$_2$ gel using CH$_2$Cl$_2$.

16.2 Preparation of estra-4,6-dien-3-one-17β-acetate

Three grams (3 g) of 19-nortestosteroneacetate-3-enolacetate was suspended in 10 mL of N,N-dimethylformamide (DMF), then 200 μL of water was added and the suspension cooled to 0° C. under an argon atmosphere. Over 45 min, 1.56 g of N bromosuccinimide (NBS) was added in small portions. Following the last addition, the solution was warmed to room temperature and 1.47 g of lithium carbonate (Li$_2$CO$_3$) and 0.75 g of lithium bromide (LiBr) were added. After heating at 95° C. for 3 hr, 200 mL of water and 10 mL of acetic acid (HOAc) were added. The resulting suspension was extracted with CH$_2$Cl$_2$, the organic phase washed with brine, dried over Na$_2$SO$_4$ and the solvent removed under reduced pressure. The product (2.15 g) was isolated by flash chromatography on SiO$_2$ gel using CH$_2$Cl$_2$ containing 0.75% methanol (CH$_3$OH).

16.3 Preparation of 7α-(t-butyldimethylsilyloxyhexyl)-estra-4-ene-3-one-17β-acetate The appropriate Grignard reagent, i.e., t-butyldimethylsilyloxyhexyl magnesium bromide (TBDMSO(CH$_2$)$_6$MgBr), was formed by the addition of 10 g of 6-bromohexyl t-butyldimethylsilyl ether to 0.9 g of magnesium turnings in 10 mL of tetrahydrofuran (THF). The suspension was heated at reflux for 20–30 min. After cooling to −35° C., 2.65 g of copper iodide (CuI) was added and the suspension kept at −35° C. for 45 min. A solution of 3 g of estra-4,6-dien-3-one-17b-acetate in 8 mL of THF was added slowly over 1 hr and the temperature maintained at −35° C. for an additional 2.5 hr. Three milliliters (3 mL) of HOAc was then added and the resulting suspension warmed to room temperature. Subsequent to addition of the suspension to water and extraction with ether, the organic phase was washed with brine, dried over Na$_2$SO$_4$, and the solvent removed under reduced pressure. The desired 7α-product (1.0 g) was purified and separated from its 7β-isomer by flash chromatography on SiO$_2$ gel using hexanes containing 20% ethyl acetate (EtOAc).

16.4 Preparation of 7α-(acetyloxyhexyl)-17β-hydroxy-estra-4-ene-3-one

One gram of 7α-(t-butyldimethylsilylhexyl)-estra-4-ene-3-one-17-acetate was dissolved in 10 mL of THF, then 5 mL of a 1M solution of tetrabutylammonium fluoride (Bu$_4$N$^+$ F—) in THF was added. After 1 hr, the solvent was removed under reduced pressure and the residue dissolved in CH$_2$Cl$_2$. The organic phase was washed with a saturated bicarbonate solution and brine, dried over Na$_2$SO$_4$ and the solvent removed under reduced pressure. The free hydroxyl group of the resulting compound was acetylated with acetic anhydride in pyridine in the presence of a catalytic amount of 4-N,N-dimethylaminopyridine (DMAP). After removal of the solvents under reduced pressure, the product was isolated by flash chromatography on SiO$_2$ gel using hexanes containing 15% EtOAc.

16.5 Synthesis of 7α-(acetyloxyhexyl)-17β-hydroxy-estra-1,3,5(10)-trien-3-ol One gram (1 g) of 7α-(acetyloxyhexyl)-17β-hydroxy-estra-4-ene-3-one was added to a suspension of 190 mg of LiBr and 1 g of copper bromide ($CuBr_2$) in 10 mL of acetonitrile ($CH_3CN$). The suspension was heated at reflux for 30 min, cooled, and 20 mL of a saturated bicarbonate solution was added. The mixture was extracted twice with EtOAc and the combined organic extracts washed with water, dried over $Na_2SO_4$ and the solvent removed under reduced pressure. The product (200 mg) was isolated by flash chromatography on $SiO_2$ gel using toluene containing 10% EtOAc.

16.6 Synthesis of 7α-(6-bromohexyl)-17β-hydroxy-3-O-methoxymethyl-estra-1,3,5(10)-triene Two hundred milligrams (200 mg) of 7α-(acetyloxyhexyl)-17β-hydroxy-estra-1,3,5-trien-3-ol was dissolved in diisopropylethylamine ((i-Pr)$_2$NEt), 0.2 mL of bromomethyl methyl ether ($CH_3OCH_2Br$) was added and the reaction stirred for 2 hr at room temperature. Thirty milliliters (30 mL) of $CH_2CH_2$ was added and the solution washed with water and brine. Following removal of the solvents under reduced pressure, the product was dissolved in 3 mL of $CH_3OH$ and treated with 0.3 mL of a 1M aqueous potassium carbonate ($K_2CO_3$) solution. After 1 hr, the solution was added to 50 mL of water. The organics were extracted with EtOAc, washed with water and dried over $Na_2SO_4$. Removal of the EtOAc produced 100 mg of crude 7α-(6-hydroxyhexyl)-17β-hydroxy-3-O-methoxymethyl-estra-1,3,5(10)-triene which was dissolved in 5 mL of THF containing 0.1 mL of (i-Pr)$_2$NEt. The THF solution was cooled to 0° C. and 0.02 mL of methanesulfonyl chloride ($CH_3SO_2Cl$) was added. After 3 hr, 50 mL water was added and the product isolated by extraction with EtOAc. Removal of solvent produced 100 mg of an intermediate which was treated with 200 mg of LiBr in DMF at 60° C. for 1 hr. The organics were isolated by extraction with ether which was washed with water, dried over $Na_2SO_4$ and the solvent removed under reduced pressure to yield the product (110 mg).

16.7 Synthesis of 1-t-butyldimethylsilyloxy-2-diphenylphosphinamide ethane

Nine grams (9 g) of potassium phthalimide was suspended in 100 mL of DMF to which 10 g of 1-bromo-2-t-butyldimethylsilyloxyethane ($BrCH_2CH_2OTBDMS$) was added and the mixture heated at 75° C. overnight. The mixture was added to 300 mL of a 5% sodium hydroxide (NaOH) solution and extracted with 300 mL of ether. The ether phase was washed twice with water, dried over $Na_2SO_4$ and the solvent removed under reduced pressure. The resulting solid was dissolved in 100 mL of $CH_3OH$, then 3 mL of hydrazine ($H_2NNH_2$) was added. After 5 hr, 300 mL ether was added and the organic phase separated from the white precipitate by filtration. Removal of the solvent under reduced pressure yielded 11 g of O-(t-butyldimethylsilyl) ethanolamine. Five grams (5 g) of O (t butyldimethylsilyl) ethanolamine was dissolved in 40 mL of THF and 8 mL of (i-Pr)$_2$NEt. Five milliliters (5 mL) of diphenylphosphinic chloride ($Ph_2P(O)Cl$) was slowly added which produced a white precipitate. After 2 hr, the THF was removed under reduced pressure and the residue dissolved in 200 mL of $CH_2Cl_2$. The $CH_2Cl_2$ solution was washed with a saturated bicarbonate solution and brine. Removal of $CH_2Cl_2$ under reduced pressure followed by flash chromatography on $SiO_2$ gel using $CH_2Cl_2$ produced the product (9 g).

16.8 Synthesis of 7α-((N-diphenylphosphino)-hydroxyethylaminohexyl)-17β-hydroxy-3-O-methoxymethyl-estra-1,3,5(10)-triene One hundred fifteen milligrams (115 mg) of 1-t-butyldimethylsilyloxy-2-diphenylphosphinamide ethane ($Ph_2P(O)NHCH_2CH_2OTBDMS$) was dissolved in 1 mL of DMF and cooled in an ice bath. Twenty five milligrams (25 mg) of sodium hydride (NaH) was added. After 40 min, 2 mL of a DMF solution containing 250 mg of 7α-(6-bromohexyl)-17β-hydroxy-3-O-methoxymethyl-estra-1,3,5 (10)-triene was added and the solution warmed to room temperature. After 3 hr, the mixture was added to 50 mL of water and the organics extracted with EtOAc, washed with water and dried over $Na_2SO_4$. After removal of the solvent under reduced pressure, the product was dissolved in 2 mL of THF and treated for 1 hr with 0.5 mL of a 1M solution of $Bu_4N^+F^-$ in THF. Removal of the solvent and flash chromatography on $SiO_2$ gel using 3% $CH_3OH$ in $CH_2Cl_2$ yielded the product (100 mg).

16.9 Synthesis of 7α-{N-(diphenylphosphino)-[2-(N-((N,N-bis-2-chloroethylaminophenyl)propyl)-carbamoyloxy)ethyl]aminohexyl}-17β-hydroxy-3-O-methoxymethyl-estra-1,3,5(10)-triene One hundred milligrams (100 mg) 7α-((N-diphenylphosphino)-hydroxyethylaminohexyl)-17β-hydroxy-3-O-methoxymethyl-estra-1,3,5(10)-triene was dissolved in 2 mL of $CH_2Cl_2$ and 0.1 mL of (i-Pr)$_2$NEt. Sixty milligrams (60 mg) of p-nitrophenylchloroformate (P-ClCO$_2$C$_6$H$_4$NO$_2$) was added to the solution and after 2 hr, the reaction was diluted with 30 mL of $CH_2Cl_2$, washed four times with a saturated bicarbonate solution and once with brine. Removal of the solvent under reduced pressure yielded a yellow oil to which was added a THF solution containing 100 mg of 3-(4-(N,N-bis-2-chloroethyl)amino) phenyl)propylamine (p ((ClCH$_2$CH$_2$)$_2$N)C$_6$H$_4$(CH$_2$)$_2$NH$_2$) and 0.1 mL of (iPr)$_2$NEt. This solution was heated and maintained at 85° C. for 2 hr. The solvent was removed and the residue dissolved in EtOAc, which was washed with a saturated bicarbonate solution and brine. The product (50 mg) was isolated by flash chromatography on $SiO_2$ gel using 2% $CH_3OH$ in $CH_2Cl_2$.

16.10 Synthesis of 7α-{N-[2-(N-((N,N-bis-2-Chloroethylaminophenyl)propyl)-carbamoyloxy) ethyl]aminohexyl}-3,17β-dihydroxyestra-1,3,5(10)-triene Removal of the methoxymethyl and diphenylphosphinamido groups was accomplished by dissolving 50 mg of 7α-{N-(diphenylphosphino)-[2-(N-((N,N-bis-2-Chloroethylaminophenyl)propyl)-carbamoyloxy)ethyl] aminohexyl}-17β-hydroxy-3-O-methoxymethyl-estra-1,3,5 (10)-triene in 1 mL of CH3OH and adding 0.025 mL of concentrated hydrochloric acid (HCl). After 3 hr, solid sodium bicarbonate ($NaHCO_3$) was added along with 25 mL of water. The product was extracted with EtOAc which was washed with water and brine. Following removal of the solvent, the product (20 mg) was isolated by flash chromatography on $SiO_2$ gel using a $CH_2Cl_2$ solution containing 2% $CH_3OH$ and 2% triethylamine ($Et_3N$).

EXAMPLE 17

Figure 17:
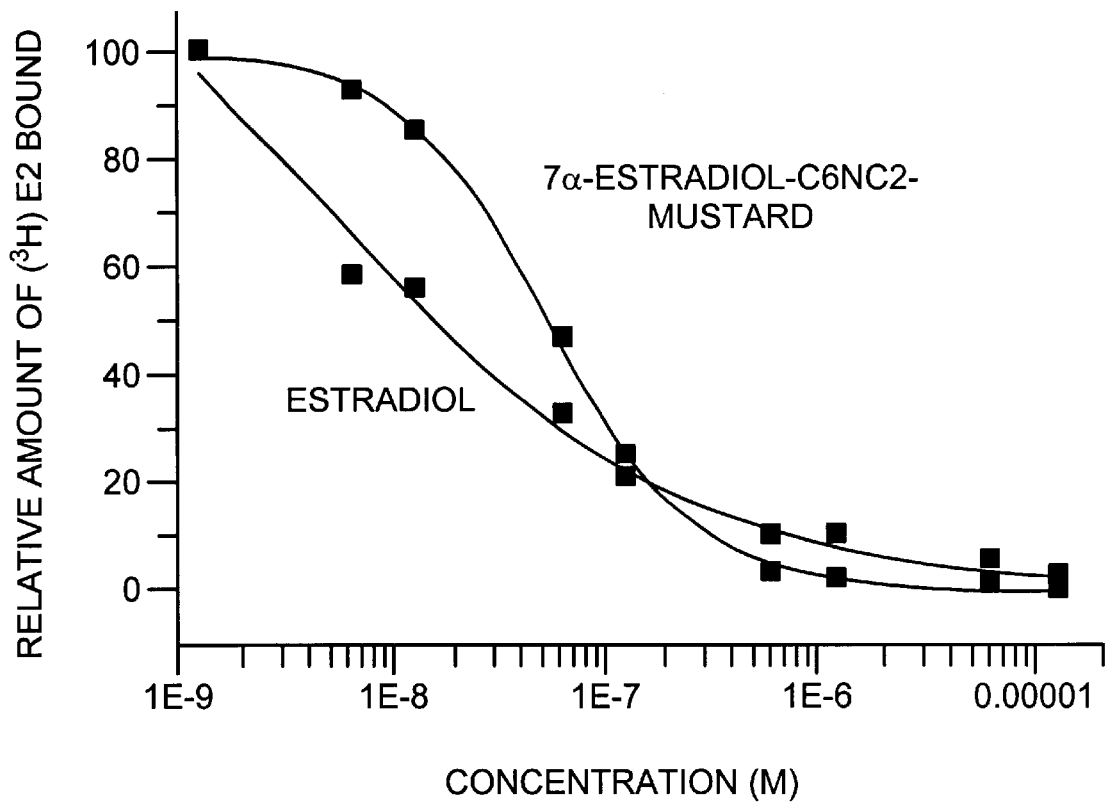
FIG. 17 presents a scatterplot of results of competition studies establishing the relative affinity of preferred heterobifunctional compound 10 for estrogen receptor.

Demonstration that the 7α-estradiol-C6NC2-mustard Compound has High Affinity for the Estrogen Receptor A receptor binding assay was carried out essentially as described in Example 13. Calf uterine extract was used as a source of estrogen receptor in these studies, results of which are set forth in FIG. 17. The 7α-estradiol-C6NC2 compound competitively displaced radiolabelled estradiol from the estrogen receptor.

EXAMPLE 18

Figure 18:
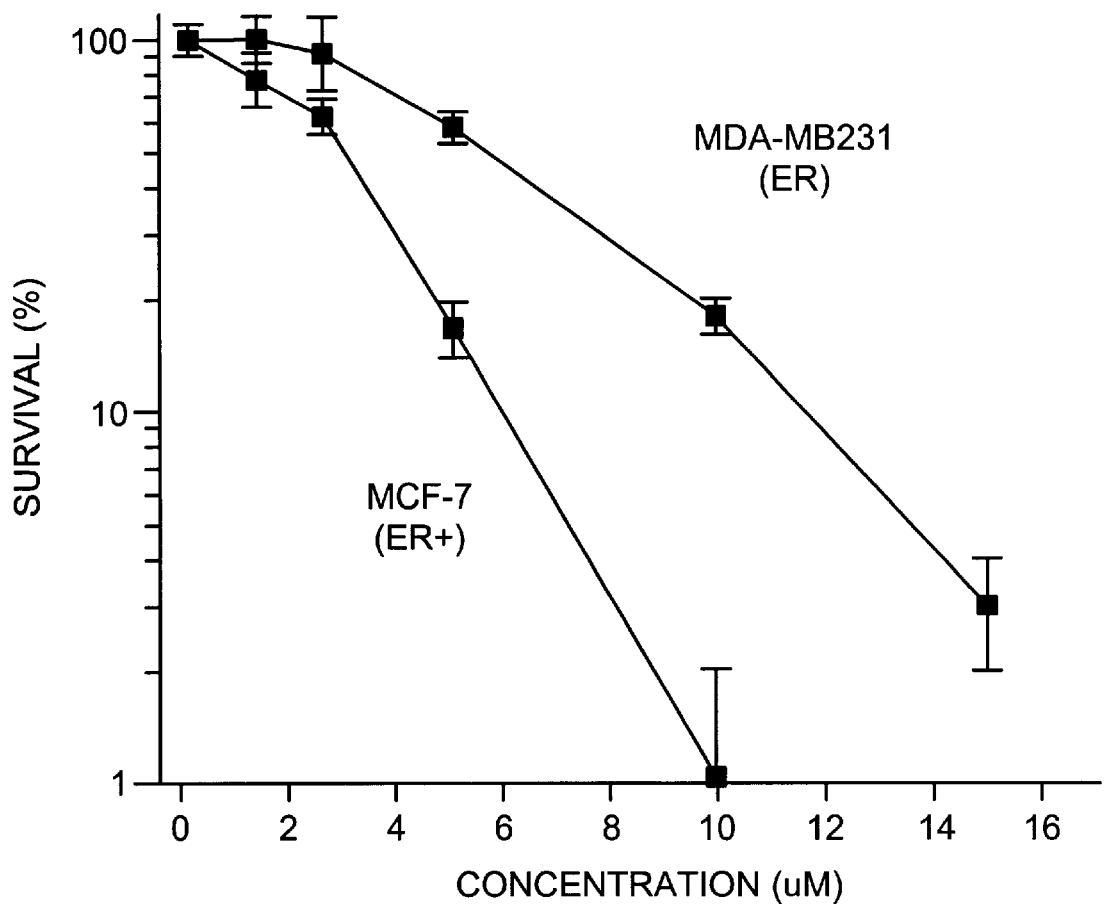
FIG. 18 is a scatterplot of results of clonogenic survival assays in which estrogen receptor positive (MCF-7) and estrogen receptor negative (MDA-MB231) breast cancer cell lines were exposed to the indicated concentrations of 7α-estradiol-C$_6$NC$_2$-mustard compound 10 for 2 hours.

Demonstration of Selective Toxicity of 7α-estradiol-C6NC2-mustard Compound to Mammalian Cells that Express the Estrogen Receptor Cells lines, culture conditions, and protocols used to assess the selective toxicity of 7α-estradiol-C6NC2-mustard were essentially described in Example 14. FIG. 18 shows the results of clonogenic survival assays in which estrogen receptor positive (MCF-7) and estrogen receptor negative (MDA-MB231) breast cancer cell lines were exposed to the indicated concentrations of 7α-estradiol-C6NC2-mustard for 2 hr. FIG. 18 demonstrates that the 7α-estradiol-C6NC2-mustard has greater cytotoxic potency in the MCF-7 cell line, which expresses high levels of estrogen receptor, than in the MDA-MB231 cell line, which does not substantially express this receptor.

EXAMPLE 19
Synthesis of a Heterobifunctional Genotoxin with a Second Agent that Mediates Binding of the Androgen Receptor A ligand decoy compound designed to attract the androgen receptor can be prepared according to the principles disclosed herein. Such a compound is preferred for achieving the selective killing of transformed human cells that express androgen receptor. In one embodiment, an androgen-chlorambucil decoy would comprise a nitrogen mustard (chlorambucil) first agent linked through a protease resistant, hydrophilic organic linker to an androgen, androgen-analog, androgen-agonist or androgen-antagonist second agent. In a further embodiment, the compound would comprise (N,N-bis-2-chloroethylaminophenyl)propylamine as its genotoxic first agent.

In another embodiment, the compound would comprise 19-nor-17β-hydroxyandrost-4-ene-3-one-7α-hexanol ("7α-19NT-C6(OH)") as a second agent.

In another embodiment, the compound would comprise a derivative of a 1,2-dihydropyridono[5,6-g]quinolone as a second agent.

In another embodiment, the compound would comprise a derivative of the antiprogestin RU486 as a second agent. In a further embodiment, the compound would comprise 17β-hydroxy-17-(1-propynyl)estra-4,9-dien-3-one as a second agent. In yet a further embodiment, the compound would comprise a 17β-hydroxy-17-(1-propynyl)estra-4,9-dien-3-one second agent linked at the 11β position to a first agent through a protease resistant, hydrophilic organic linker.

Sources of guidance for the synthesis of second agents designed to attract the androgen receptor include Hackenberg et al. (1996) 32A *Euro. J. Cancer* 696–701, which discusses the androgen-like and anti-androgen-like effects of antiprogestins, and Hamann et al. (1998) *J. Med. Chem.* 623–639, which discusses a series of androgen receptor antagonists. The teachings of these papers are herein incorporated by reference.

The methods of synthesis of these compounds would be similar to those used in Examples 12 and 16, and would employ techniques well known to one of ordinary skill in the art.

EXAMPLE 20
Use of a Heterobifunctional Genotoxin with a Second Agent that Mediates Binding the the Androgen Receptor Specificity of an androgen receptor decoy for killing tumor cells that express the androgen receptor can be tested readily in available cell culture models for prostate cancer. A heterobifunctional genotoxin with an androgen-analog second agent can be demonstrated to selectively target cells expressing the androgen receptor in a method analogous to Examples 10, 14 and 18.

Similar techniques can be applied or adapted with no more than routine experimentation, to demonstrate functional properties of heterobifunctional compounds programmed to attract the androgen receptor. Electrophoretic mobility shift and DNase I protection analysis are suitable techniques generally for demonstrating whether a particular heterobifunctional compound forms genotoxic lesions, whether a chosen cell component is bound by a suitably programmed heterobifunctional compound, and whether the resulting complex is effective for shielding genomic lesions from the action of enzymes that act on cellular DNA.

Cell sensitivity can be assessed using a growth inhibition assay. Equal concentrations of chlorambucil and the androgen-chlorambucil decoy can be added to cell cultures, and the rate of cell proliferation determined by counting the number of cells in replica cultures up to seven days post treatment. The increase in cell numbers in both treated and untreated control cultures can be compared to assess potential antitumor effects. Favorable results should be confirmed by repeating the test using a phenotypically different pair of receptor-bearing and receptor independent cell lines. Androgen receptor-bearing cell lines include, but are not limited to, LNCaP.FGC, PC-3, and DU 145, all available from the American Type Culture Collection (Rockville, Md.). Drugs that demonstrate a 2–4 fold or greater ability to inhibit the growth of androgen receptor positive cells, as compared to receptor negative cells, should be selected for further testing in appropriate mammals.

Equivalents

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A cell membrane per meant heterobifunctional compound effective in destroying selected cells in a heterogenous cell population, comprising
   i) a first agent that mediates binding of said compound to cellular DNA to form a genomic lesion, wherein said first agent is selected from the group consisting of alkylating agents and heavy metal coordination compounds;
   ii) a second agent that mediates binding of a steroid receptor protein to said compound, wherein said protein is preferentially present in selected cells of the population; and,
   iii) a hydrophilic linker stable under intracellular conditions, wherein said linker covalently connects said first agent to said second agent such that said heterobifunctional compound can concurrently bind said cellular DNA and said cell component to shield said genomic lesion.

2. A pharmaceutical composition comprising a cell membrane per meant heterobifunctional compound dispersed in a physically acceptable carrier, said compound being effective in destroying selected cells in a heterogenous cell population and comprising
   i) a first agent that mediates binding of said compound to cellular DNA to form a genomic lesion, wherein said first agent is selected from the group consisting of alkylating agents and heavy metal coordination compounds;
   ii) a second agent that mediates binding of a steroid receptor protein to said compound, wherein said protein is preferentially present in selected cells of the population; and,
   iii) a hydrophilic linker stable under intracellular conditions, wherein said linker covalently connects said first agent to said second agent such that said heterobifunctional compound can concurrently bind said cellular DNA and said cell component to shield said genomic lesion.

3. The compound 7α-{N-(2-(N-((N,N-bis-2-chloroethylaminophenyl)propyl)-carbamoyloxy)ethyl)aminohexyl}-3,17β-dihydroxyestra-1,3,5(10)-triene.

4. The compound of claim 1, wherein said first agent is mitoguazone or a mitoguazone analog or derivative covalently connected to said second agent by said hydrophilic linker.

5. A compound of claim 1, wherein said first agent is procarbazine or a procarbozine analog or derivative covalently connected to said second agent by said hydrophilic linker.

6. A compound of claim 1, wherein said linker is an organic linker.

7. A compound of claim 6, wherein said organic linker comprises up to about 20 carbon atoms.

8. A compound of claim 7 wherein said organic linker comprises up to about 10 carbon atoms.

9. A compound of claim 8 wherein said organic linker comprises up to about 5 carbon atoms.

10. A compound of claim 1 wherein said selected cells are dividing cells.

11. A compound of claim 10 wherein said dividing cells are transformed cells.

12. A compound of claim 1, wherein said second agent is a ligand that binds to said steroid receptor protein.

13. A compound of claim 1 wherein said steroid receptor protein is selected from a group consisting of: a glucocorticoid receptor, an androgen receptor, an estrogen receptor and a progesterone receptor.

14. A compound of claim 13 wherein said steroid receptor protein is an estrogen receptor and said second agent is a 2-phenylindole moiety.

15. A compound of claim 1, wherein said second agent is an androgen or an androgen analog, derivative, precursor or metabolite covalently connected to said first agent by said hydrophilic linker.

16. A pharmaceutical composition comprising:
(a) the compound of claim 1, dispensed in
(b) a pharmaceutically acceptable carrier.

17. A method of killing cells comprising the step of administering the cell membrane per meant heterobifunctional genotoxic compound of claim 1 to said cells.

18. The method of claim 17 wherein said cells are tumorigenic.

19. The method of claim 17 wherein said cells are of reproductive tract origin.

20. The method of claim 17 wherein said cells are of prostate origin.

21. The method of claim 17 wherein said cells are of testicular origin.

22. The method of claim 17 wherein said cells are of breast origin.

23. The method of claim 17 wherein said cells are of ovarian origin.

24. The method of claim 17 wherein said cell permeant heterobifunctional genotoxin is provided in a pharmaceutically acceptable carrier.

25. The compound of claim 1, wherein said first agent is an alkylating agent.

26. The compound of claim 25, wherein said alkylating agent is a chloroethylnitrosourea or nitrogen mustard.

27. The compound of claim 26, wherein said chloroethylnitrosourea is selected from the group consisting of: carmustine, chlorozotocin, lomustine, nimustine, ranimustine, streptozotocin, and a chloroethylnitrosourea analog or derivative thereof covalently connected to said second agent by said hydrophilic linker.

28. The compound of claim 26, wherein said nitrogen mustard is selected from the group consisting of: chlorambucil, cyclophosphamide, ifosfamide, melphalan, mechloroethamine, and a nitrogen mustard analog or derivative thereof covalently connected to said second agent by said hydrophilic linker.

29. The compound of claim 1, wherein said first agent is a heavy metal coordination compound.

30. The compound of claim 29, wherein said heavy metal coordination compound is selected from the group consisting of: carboplatin, cisplatin, transplatin, and a heavy metal coordination compound analog or derivative thereof covalently connected to said second agent by said hydrophilic linker.

31. The compound of claim 25, wherein said alkylating agent is an alkylsulfonate selected from the group consisting of: busulfan, hepsulfan, and an alkylsulfonate analog or derivative thereof covalently connected to said second agent by said hydrophilic linker.

32. The compound of claim 25, wherein said alkylating agent is selected from the group consisting of: hexamethylmelamine, triethylenemelamine, and an alkylating agent analog or derivative thereof covalently connected to said second agent by said hydrophilic linker.

33. The compound of claim 25, wherein said alkylating agent is an aziridine selected from the group consisting of: triethylenephosphoramide, triethylenethiophosphoramide, and an aziridine analog or derivative thereof covalently connected to said second agent by said hydrophilic linker.

34. The compound of claim 25, wherein said alkylating agent is a synthetically or naturally sourced antibiotic.

35. The compound of claim 34, wherein said antibiotic is an antineoplastic antibiotic.

36. The compound of claim 35, wherein said antineoplastic antibiotic is selected from the group consisting of: mitomycin A, mitomycin B, mitomycin C, and an antineoplastic antibiotic analog or derivative thereof covalently connected to said second agent by said hydrophilic linker.

* * * * *